US008715680B2

(12) United States Patent
Ball et al.

(10) Patent No.: US 8,715,680 B2
(45) Date of Patent: May 6, 2014

(54) HLA PEPTIDE THERAPY

(75) Inventors: Simon Ball, Birmingham (GB);
Bernard Maillere, Gif sur Yvette (FR)

(73) Assignee: The University of Birmingham, Birmingham (GB)

( * ) Notice: Subject to any disclaimer, the term of this patent is extended or adjusted under 35 U.S.C. 154(b) by 599 days.

(21) Appl. No.: 12/299,801

(22) PCT Filed: May 9, 2007

(86) PCT No.: PCT/GB2007/001690
§ 371 (c)(1),
(2), (4) Date: Mar. 10, 2010

(87) PCT Pub. No.: WO2007/129093
PCT Pub. Date: Nov. 15, 2007

(65) Prior Publication Data
US 2010/0215619 A1      Aug. 26, 2010

(30) Foreign Application Priority Data

May 9, 2006   (GB) .................................. 0609121.9

(51) Int. Cl.
*A61K 39/00* (2006.01)
*A61K 38/00* (2006.01)
*A61K 38/04* (2006.01)
*A61K 38/16* (2006.01)
*C07H 21/04* (2006.01)

(52) U.S. Cl.
USPC .......... 424/185.1; 530/324; 530/325; 530/326

(58) Field of Classification Search
None
See application file for complete search history.

(56) References Cited

U.S. PATENT DOCUMENTS 7,135,302 B1   11/2006   Itescu

FOREIGN PATENT DOCUMENTS

| EP | 1642905 B1 | 4/2006 |
|---|---|---|
| WO | WO 93/08817 A1 * | 5/1993 |
| WO | WO-93/17699 A1 | 9/1993 |
| WO | WO-94/04171 A1 | 3/1994 |
| WO | WO-95/05189 A1 | 2/1995 |
| WO | WO-95/34321 A1 | 12/1995 |
| WO | WO-97/32605 A1 | 9/1997 |
| WO | WO-03/016905 A2 | 2/2003 |
| WO | WO-2005/038030 A1 | 4/2005 |

OTHER PUBLICATIONS

Meyerson et al (J. Immunol. 1996, 156: 574-584).*
Onlinelibrary. onlinelibrary.wiley.com, May 15, 2012, pp. 1-3.*
MiMi Biology, world wide web at en.mimi.hu/biology/identity.html, 2013.*
Mallios (Bioinformatics, 1999, 15(6): 432-439).*
Brusic et al (Bioinformatics, 1998, 14(2): 121-130).*
Papassavas, A.C., "HLA Peptide-mediated Strategies for Modulation of Cellular and Humoral Immune Response in Transplantation," *Current Pharmacogenomics*, vol. 1:17-36 (2003).
International Search Report for Application No. PCT/GB2007/001690, dated Oct. 26, 2007.
Written Opinion for Application No. PCT/GB2007/001690, dated Oct. 26, 2007.
International Preliminary Report on Patentability for Application No. PCT/GB2007/001690, dated Nov. 20, 2008.
Fangmann, Josef et al., "T cell recognition of donor major histocompatibility complex class I peptides during allograft rejection," *Eur. J. Immunol.*, vol. 22:1525-1530 (1992).
Freese, Anja et al., "HLA-B7 β-pleated sheet-derived synthetic peptides are immunodominant T-cell epitopes regulating alloresponses," *Blood*, vol. 99:3286-3292 (2002).
Hanvesakul, R. et al., "Indirect Recognition of T-Cell Epitopes Derived from the α 3 and Transmembrane Domain of HLA-A2," *American Journal of Transplantation*, vol. 7:1148-1157 (2007).
Heeger, Peter S. et al., "Pretransplant Frequency of Donor-Specific IFN-γ-Producing Lymphocytes Is a Manifestation of Immunologic Memory and Correlates with the Risk of Posttransplant Rejection Episodes," *The Journal of Immunology*, vol. 163:2267-2275 (1999).
Iacomini, John et al., "Measuring T Cell Alloreactivity to Predict Kidney Transplant Outcomes: Are We There Yet?" *J. Am. Soc. Nephrol.*, vol. 17:328-330 (2006).
Lakkis, Fadi G. et al., "Memory T Cells: A Hurdle to Immunologic Tolerance," *J. Am. Soc. Nephrol.*, vol. 14:2402-2410 (2003).
Nakajima, Jun et al., "Cytotoxic Lymphocytes Directed Against Donor HLA Class I Antigens on Airway Epithelial Cells are Present in Bronchoalveolar Lavage Fluid from Lung Transplant Recipients During Acute Rejection," *J. Thorac. Cardiovasc. Surg.*, vol. 117:565-571 (1999).
Reinsmoen, N.L., "Cellular methods used to evaluate the immune response in transplantation," *Tissue Antigens*, vol. 59:241-250 (2002).
Sitaru, Ana Gabriela et al., "Hierarchical Immunogenicity of Donor MHC Class I Peptides in Allotransplantation," *Human Immunology*, vol. 63:871-879 (2002).
SivaSai, Krovvidi S.R. et al., "Indirect Recognition of Donor HLA Class I Peptides in Lung Transplant Recipients with Bronchiolitis Obliterans Syndrome," Transplantation, vol. 67(8):1094-1098 (1999).
Stegmann, Sandra et al., "Synthetic HLA-A2 Derived Peptides are Recognized and Presented in Renal Graft Recipients," Human Immunology, vol. 61:1363-1369 (2000).
White, Janice et al., "Soluble Class I MHC with 2-Micoglobulin Covalently Linked Peptides: Specific Binding to a T Cell Hybridoma," The Journal of Immunology, vol. 162:2671-2676 (1999).

* cited by examiner

*Primary Examiner* — Gerald R Ewoldt
*Assistant Examiner* — Marianne Dibrino
(74) *Attorney, Agent, or Firm* — Nelson Mullins Riley & Scarborough LLP; Jane E. Remillard, Esq.; Jeanne M. DiGiorgio

(57) ABSTRACT

The invention provides polypeptides derived from a major histocompatibility complex (MHC) class I human leukocyte antigen (HLA), such as HLA-A2, and derivatives or analogues thereof. The polypeptides, derivatives and analogues can be used to treat or prevent allosensitisation, such as the treatment or prevention of allograft rejection.

5 Claims, 21 Drawing Sheets

Fig. 3

| Peptides | name | MW |
|---|---|---|
| p1 | A2 3-17 | 1827.1 |
| p2 | A2 5-19 | 1789 |
| p3 | A2 10-24 | 1628.8 |
| p4 | A2 20-34 | 1726 |
| p5 | A2 23-37 | 1743.9 |
| p6 | A2 25-39 | 1761.9 |
| p7 | A2 31-45 | 1757.9 |
| p8 | A2 34-48 | 1763.9 |
| p9 | A2 42-57 | 1910.1 |
| p10 | A2 49-63 | 1804.9 |
| p11 | A2 57-71 | 1802 |
| p12 | A2 65-79 | 1731 |
| p13 | A2 74-88 | 1778 |
| p14 | A2 76-90 | 1684.8 |
| p15 | A2 79-93 | 1638.7 |
| p16 | A2 82-96 | 1695.8 |
| p17 | A2 93-107 | 1752.9 |
| p18 | A2 95-110 | 1931.2 |
| p19 | A2 101-115 | 1838 |
| p20 | A2 105-119 | 1976.1 |
| p21 | A2 107-121 | 1959.2 |
| p22 | A2 111-125 | 1819 |
| p23 | A2 114-128 | 1813 |
| p24 | A2 116-130 | 1776 |
| p25 | A2 121-135 | 1808.1 |
| p26 | A2 124-138 | 1719 |
| p27 | A2 128-142 | 1664.8 |
| p28 | A2 131-145 | 1673.9 |
| p29 | A2 136-150 | 1657.9 |
| p30 | A2 145-159 | 1808 |

Fig. 3 (Cont.)

| Peptide | Region | ID |
|---------|--------|------|
| p31 | A2 150-164 | 1660 |
| p32 | A2 154-168 | 1809 |
| p33 | A2 157-171 | 1914 |
| p34 | A2 163-177 | 1895 |
| p35 | A2 165-179 | 1905 |
| p36 | A2 169-183 | 1878 |
| p37 | A2 177-191 | 1765 |
| p38 | A2 187-201 | 1686 |
| p39 | A2 192-206 | 1708 |
| p40 | A2 202-216 | 1770 |
| p41 | A2 206-220 | 1839 |
| p42 | A2 211-225 | 1762 |
| p43 | A2 215-229 | 1821 |
| p44 | A2 228-242 | 1621 |
| p45 | A2 239-253 | 1574 |
| p46 | A2 241-256 | 1829 |
| p47 | A2 245-259 | 1607 |
| p48 | A2 254-269 | 1921 |
| p49 | A2 264-278 | 1709 |
| p50 | A2 268-282 | 1752 |
| p51 | A2 270-284 | 1737 |
| p52 | A2 280-294 | 1522 |
| p53 | A2 282-296 | 1452 |

Fig. 4

| peptides | DR1 | DR3 | DR4 | DR7 | DR11 | DR13 | DR15 | DRB3 | DRB4 | DRB5 |
|---|---|---|---|---|---|---|---|---|---|---|
| p1 | 2.7 | 25.8 | 0.9 | 6.5 | 0.1 | 2.4 | 11.5 | >6202 | 12.1 | 0.5 |
| p2 | 1.8 | 10.4 | 0.9 | 7.6 | 0.1 | 2.6 | 26.4 | >6202 | >3686 | 0.6 |
| p3 | 529.2 | >330 | 273.9 | 1234.4 | 70.5 | >766 | 386.7 | >6202 | >3686 | >12910 |
| p4 | 788.8 | 38.1 | >4524 | 131.2 | 275.2 | >766 | 16.3 | 12.2 | 2263.3 | 97.3 |
| p5 | 3570.7 | 1.2 | 1333.3 | 523.7 | 637.7 | >766 | 67.2 | 3.7 | >3686 | 103.1 |
| p6 | 29250 | 2.2 | 4194.4 | 534.5 | 126.5 | >766 | 36.7 | 15.2 | 5294.1 | 1186.7 |
| p7 | 100 | 0.6 | 17.7 | 132.8 | 276.7 | >766 | 4.6 | 28.3 | 96.5 | 200 |
| p8 | 14720 | 5.1 | 169.6 | 828.1 | 2930.2 | >766 | >1786 | 166.4 | >3686 | 461.9 |
| p9 | 11402 | >330 | >4524 | 14907 | 700 | 539.9 | >1786 | >6202 | >3686 | 8660.3 |
| p10 | 13663 | 158.1 | >4524 | 14142 | 2919.4 | >766 | 1059.1 | 3797.8 | >3686 | 9486.8 |
| p11 | 4041.5 | >330 | 2721.7 | 11212 | 28.9 | >766 | >1786 | >6202 | >3686 | 3146.4 |
| p12 | 22804 | >330 | 4303.3 | 82.2 | >5456 | 2.5 | >1786 | >6202 | 227.5 | 1030.8 |
| p13 | 115.5 | >330 | 202 | 6546.5 | 557.7 | >766 | 2 | >6202 | 3321.1 | 1596.9 |
| p14 | 170.7 | >330 | 380.1 | >18036 | 107.2 | >766 | 1 | >6202 | >3686 | 1414.2 |
| p15 | 372.4 | >330 | 96.9 | 500 | 128.5 | >766 | 0.7 | >6202 | >3686 | 79.1 |
| p16 | 13.8 | >330 | 24.7 | 22 | 219.6 | >766 | >1786 | >6202 | >3686 | 22.6 |
| p17 | 28.9 | 17.6 | 106.1 | 293.9 | 325.7 | >766 | 39 | 32.8 | 0.7 | 1602.8 |
| p18 | 72.1 | >330 | 92.2 | 736.8 | 124.7 | >766 | 65.3 | 1.9 | 0.9 | 191.9 |
| p19 | 10 | 5.5 | 27.2 | 57.6 | 2 | 769.2 | 13.5 | >6202 | 1137.6 | 4.3 |
| p20 | 0.9 | 94 | 1.4 | 6.9 | 0.1 | 6.5 | 0.4 | 82.9 | 1002.9 | 0.5 |

Fig. 4 (Cont. I)

| peptides | DR1 | DR3 | DR4 | DR7 | DR11 | DR13 | DR15 | DRB3 | DRB4 | DRB5 |
|---|---|---|---|---|---|---|---|---|---|---|
| p21 | 0.6 | 62.3 | 4.6 | 534.5 | 0.9 | 3.1 | 0.3 | 237.4 | 278.7 | 2.2 |
| p22 | 7746 | 31 | 3509.2 | 5957.5 | 121 | >766 | >1786 | 79.7 | >3686 | 5164 |
| p23 | 331.7 | 162.7 | 760.1 | 6733 | 47.3 | >766 | >1786 | 142.1 | >3686 | 193.6 |
| p24 | 28.5 | >330 | 193.6 | 755.9 | 12.8 | >766 | >1786 | >6202 | >3686 | 469 |
| p25 | 10.3 | 6 | 16.2 | 500 | 2.9 | 17.9 | 2.8 | 5304.2 | 1355.8 | 6.8 |
| p26 | 123.3 | 16.8 | 195.6 | 139.4 | 317 | 422.1 | 10.6 | >6202 | >3686 | 183.8 |
| p27 | >103574 | >330 | >4524 | >18036 | >5456 | >766 | 14.7 | >6202 | >3686 | 242.2 |
| p28 | 54.8 | >330 | 76.5 | 2288.7 | 725.5 | >766 | >1786 | 2511.5 | >3686 | 129.1 |
| p29 | 42164 | >330 | >4524 | >18036 | >5456 | 25.3 | >1786 | >6202 | >3686 | 4.2 |
| p30 | 24 | 52.5 | 5.9 | 67.9 | 26.2 | >766 | 21.2 | >6202 | >3686 | 104.1 |
| p31 | 513.8 | >330 | >4524 | >18036 | 167.6 | 52.7 | 0.6 | >6202 | >5346 | >12703 |
| p32 | 51.4 | 5.8 | 74.5 | 26.5 | 28.5 | >766 | 6.2 | >6202 | >5346 | 141.4 |
| p33 | 20.3 | 110.9 | 458.3 | 107.7 | 60.3 | 120.7 | 107.4 | >6202 | 626.2 | 1154.7 |
| p34 | >91287 | >330 | >4524 | >18036 | 16.9 | 32.7 | 459.5 | >6202 | >5346 | 7261.8 |
| p35 | 488.2 | >330 | >4524 | >18036 | 17.4 | 52.7 | 5.5 | >6202 | >5346 | >12703 |
| p36 | 575 | >330 | 1204.9 | >18036 | 51 | 104.6 | 2017 | >6202 | >5346 | 606.2 |
| p37 | 2108.2 | >330 | 2582 | 557.8 | >5694 | >766 | >2287 | >6202 | >5346 | 3446 |
| p38 | 84327 | >330 | >4524 | 9561.8 | >5456 | >766 | >2287 | >6202 | >5346 | >12703 |
| p39 | 11.3 | >330 | 64.2 | 8837.2 | 1690.9 | 38.4 | 3.2 | >6202 | 0.1 | 6495.2 |
| p40 | 21.4 | 19.1 | 100 | 7.6 | 3396.8 | >766 | 0.6 | 50.4 | 346.4 | 512.3 |
| p41 | 40.8 | >330 | 45.8 | >18036 | 162.2 | >766 | >2287 | >6202 | >5346 | >12703 |
| p42 | 1095.4 | >330 | >4524 | >18036 | 415 | >766 | 1020.5 | 290.9 | 351.5 | 3750 |
| p43 | >91287 | 309.8 | >4524 | >18036 | >5456 | >766 | >2287 | 254.2 | >5346 | >12703 |
| p44 | 3651.5 | >330 | 3027.7 | 385.4 | 605 | >766 | >2287 | >6202 | >5346 | >12703 |

Fig. 4 (Cont. II)

| peptides | DR1 | DR3 | DR4 | DR7 | DR11 | DR13 | DR15 | DRB3 | DRB4 | DRB5 |
|---|---|---|---|---|---|---|---|---|---|---|
| p45 | 2.4 | >330 | 4.9 | 4.5 | 23.5 | >766 | 10.7 | >6202 | >5346 | 5.8 |
| p46 | 178 | 26.8 | 16.3 | 118.3 | 43.3 | >766 | >2287 | >6202 | >5346 | 223.6 |
| p47 | 1825.7 | 3.6 | >4524 | 7521.4 | 4646.6 | 48.9 | >2287 | >6202 | >5346 | 197.5 |
| p48 | 1566.3 | >330 | 2472.1 | 5255.4 | 47.9 | >766 | >2287 | >6202 | >5346 | 2561.7 |
| p49 | 406.2 | >330 | 24.9 | 12649 | 142.6 | >766 | 1176.7 | >6202 | 1500.3 | 605.5 |
| p50 | 374.2 | >330 | 5.8 | 16.5 | 788.7 | >766 | 127.1 | 2842 | 264.6 | 458.3 |
| p50 | 374.2 | >330 | 5.8 | 16.5 | 788.7 | >766 | 127.1 | 2842 | 264.6 | 458.3 |
| p51 | 429 | >330 | 24.9 | 12.2 | >5456 | >766 | 55.2 | >6202 | 1150.4 | 3622.8 |
| p52 | 15.5 | >330 | >4524 | 35.9 | >5456 | >766 | >2287 | >6202 | >5346 | >12703 |
| p53 | 21.6 | 0.4 | >4524 | 30.2 | >5456 | 10.5 | 15.4 | >6202 | >5346 | 12703 |

Fig. 5
Peptides 39
Sequences: 192-206
H A V S D H E A T L R C W A L
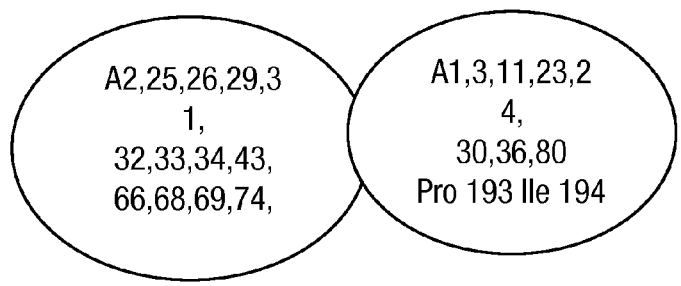
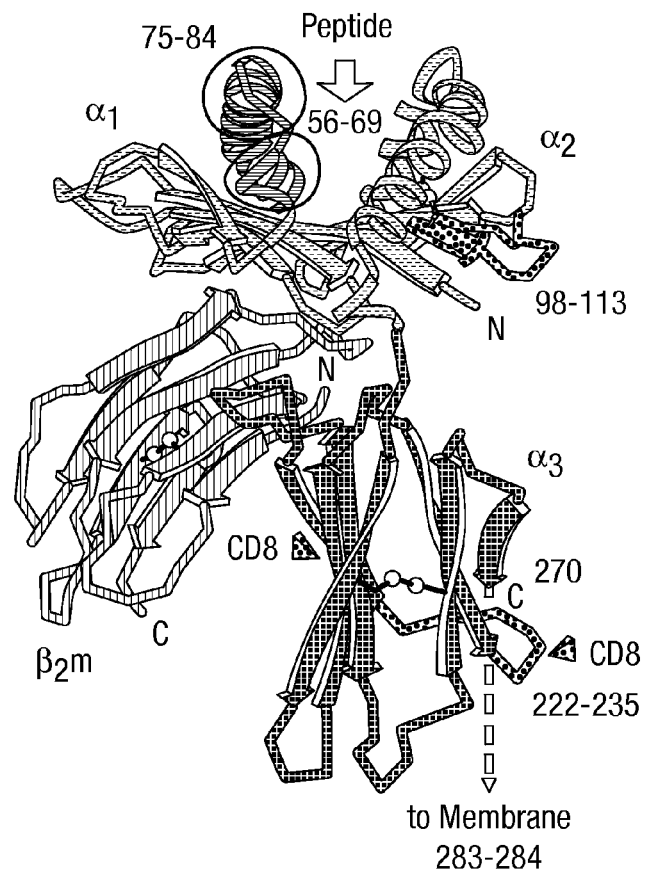

Fig. 9

| Allele | | DR1 | DR3 | DR4 | DR7 | DR11 IC50 | DR13 | DR15 | DRB3 | DRB4 | DRB5 |
|---|---|---|---|---|---|---|---|---|---|---|---|
| Peptide | Sequence | | | | | | | | | | |
| p1*| | 3-17 | 3 | 7348 | 13 | 38 | 2 | 365 | 509 | >100000 | 193 | 4 |
| p2* | 5-19 | 2 | 2837 | 18 | 45 | 3 | 399 | 1166 | >100000 | >100000 | 4 |
| p3 | 10-24 | 648 | >100000 | 5477 | 6928 | 1020 | >100000 | 18708 | >100000 | >100000 | >100000 |
| p4 | 20-34 | 748 | 12000 | >100000 | 850 | 5477 | >100000 | 1342 | 196 | 45717 | 755 |
| p5 | 23-37 | 2766 | 316 | 30984 | 3098 | 9220 | >100000 | 2966 | 59 | >100000 | 798 |
| p6 | 25-39 | 27749 | 600 | 97468 | 3162 | 2797 | >100000 | 1775 | 245 | 90000 | 9192 |
| p7* | 31-45 | 122 | 164 | 354 | 786 | 4000 | >100000 | 374 | 456 | 2182 | 1549 |
| p8* | 34-48 | 13964 | 1396 | 3391 | 4648 | 58310 | >100000 | >100000 | 2683 | >100000 | 3578 |
| p9 | 42-57 | 10817 | >100000 | >100000 | 83666 | 15474 | 60000 | 33166 | >100000 | >100000 | 67082 |
| p10 | 49-63 | 12961 | 49749 | >100000 | 79373 | 58095 | >100000 | 51235 | 75000 | >100000 | 73485 |
| p11 | 57-71 | 4950 | >100000 | 63246 | 62929 | 418 | >100000 | >100000 | >100000 | >100000 | 24372 |
| p12 | 65-79 | 21633 | >100000 | 100000 | 486 | >100000 | 385 | >100000 | >100000 | >100000 | 7984 |
| p13* | 74-88 | 89 | >100000 | 4040 | 36742 | 8062 | >100000 | 88 | >100000 | 2966 | 12369 |
| p14* | 76-90 | 209 | >100000 | 8832 | >100000 | 1549 | >100000 | 82 | 529 | 67082 | 10954 |
| p15* | 79-93 | 456 | >100000 | 1817 | 2958 | 1857 | >100000 | 33 | 30 | >100000 | 612 |
| p16* | 82-96 | 17 | >100000 | 494 | 130 | 3175 | >100000 | >100000 | >100000 | >100000 | 175 |
| p17* | 93-107 | 35 | 5612 | 2121 | 1587 | 6481 | >100000 | 2828 | 529 | 15 | 12021 |
| p18* | 95-110 | 88 | >100000 | 1844 | 4775 | 1803 | >100000 | 5612 | 30 | 19 | 1487 |
| p19 | 101-115 | 9 | 1500 | 543 | 341 | 29 | 100000 | 598 | >100000 | 51381 | 33 |
| p20 | 105-119 | 1 | 29563 | 27 | 53 | 2 | 1000 | 19 | 1336 | 13077 | 4 |
| p21 | 107-121 | 1 | 19596 | 92 | 3000 | 18 | 474 | 15 | 4709 | 3633 | 17 |
| p22 | 111-125 | 9487 | 8485 | 81548 | 33437 | 1749 | >100000 | >100000 | 1285 | >100000 | 40000 |
| p23 | 114-128 | 406 | 51962 | 17664 | 37789 | 684 | >100000 | >100000 | 2291 | >100000 | 1500 |
| p24 | 116-130 | 35 | >100000 | 3873 | 4472 | 184 | >100000 | >100000 | >100000 | >100000 | 3633 |
| p25 | 121-135 | 10 | 1631 | 325 | 2958 | 42 | 2739 | 125 | 85528 | 27386 | 52 |
| p26 | 124-138 | 151 | 4613 | 39126 | 825 | 4583 | 46904 | 469 | >100000 | >100000 | 1378 |
| p27 | 128-142 | >100000 | >100000 | >100000 | >100000 | >100000 | >100000 | 648 | >100000 | >100000 | 1876 |
| p28 | 131-145 | 67 | >100000 | 1530 | 12845 | 10488 | >100000 | >100000 | 40497 | >100000 | 1000 |

Fig. 9 (Cont.)

| | | | | | | | | |
|---|---|---|---|---|---|---|---|---|
| p29 | 136-150 | 40000 | >100000 | >100000 | >100000 | 3873 | >100000 | >100000 | 33 |
| p30 | 145-159 | 29 | 16523 | 118 | 401 | >100000 | 938 | >100000 | 806 |
| p31 | 150-164 | 629 | >100000 | >100000 | 3340 | 8062 | 26 | >100000 | >100000 |
| p32 | 154-168 | 63 | 1844 | 1732 | 149 | >100000 | 276 | >100000 | 1095 |
| p33 | 157-171 | 25 | 34900 | 9165 | 637 | 13416 | 4743 | 12649 | 8944 |
| p34* | 163-177 | >100000 | >100000 | >100000 | >100000 | 5000 | 22226 | >100000 | 58095 |
| p35* | 165-179 | 598 | >100000 | >100000 | 251 | 8062 | 245 | >100000 | >100000 |
| p36 | 169-183 | 704 | >100000 | 28000 | 738 | 11619 | 68993 | >100000 | 4850 |
| p37 | 177-191 | 2000 | >100000 | 60000 | >100000 | >100000 | >100000 | >100000 | 27568 |
| p38 | 187-201 | 80000 | >100000 | >100000 | 53666 | >100000 | >100000 | >100000 | >100000 |
| p39 | 192-206 | 18 | >100000 | 1285 | 25080 | 4271 | 140 | >100000 | 51962 |
| p40 | 202-216 | 26 | 5225 | 2000 | 45 | >100000 | 28 | 8 | 3969 |
| p41 | 206-220 | 50 | >100000 | 917 | >100000 | >100000 | >100000 | 4517 | >100000 |
| p42 | 211-225 | 1342 | >100000 | >100000 | 6000 | >100000 | 18762 | 4583 | 30000 |
| p43 | 215-229 | >100000 | 97468 | >100000 | >100000 | >100000 | 4099 | >100000 | >100000 |
| p44 | 228-242 | 4472 | >100000 | 70356 | 8746 | >100000 | 474 | >100000 | >100000 |
| p45* | 239-253 | 4 | >100000 | 99 | 340 | >100000 | >100000 | >100000 | 45 |
| p46* | 241-256 | 218 | 7348 | 326 | 626 | >100000 | >100000 | >100000 | 1732 |
| p47 | 245-259 | 2236 | 980 | >100000 | 42214 | 7483 | >100000 | >100000 | 1530 |
| p48 | 245-269 | 1918 | >100000 | 57446 | 29496 | >100000 | >100000 | >100000 | 20494 |
| p49 | 264-278 | 497 | >100000 | 497 | 70993 | >100000 | 50200 | 33882 | 4690 |
| p50* | 268-282 | 458 | >100000 | 134 | 97 | >100000 | 5612 | 45826 | 3550 |
| p51* | 270-284 | 525 | >100000 | 497 | 72 | >100000 | 2439 | >100000 | 28983 |
| p52* | 280-294 | 19 | >100000 | >100000 | 212 | >100000 | >100000 | >100000 | >100000 |
| p53* | 282-296 | 26 | 131 | >100000 | 179 | 1367 | 283 | >100000 | >100000 |

Fig. 10

| Patient ID | Age | Sex | Previous transplant | Previous transfusion | HLA Type | | | Anti-HLA specificities |
|---|---|---|---|---|---|---|---|---|
| | | | | | A | B | DR | |
| Group 1 | | | | | | | | |
| 1.1 | 37 | F | N | Y | 1,68 | 37,44 | 10,11 | A2,3,9,11,29,33,34,66,69,74,B,C,DR |
| 1.2 | 45 | M | Y (1) | Y | 23 | 7,72 | 11 | A1,2,3,10,11,19,24,28,36,43,80,B,DR |
| 1.3 | 42 | F | Y (1) | Y | 3,29 | 7,27 | 11,15 | A1,2,9,10,11,28,32,36,43,80,B,C,DR,DQ |
| 1.4 | 48 | F | N | N | 3,11 | 7,62 | 4,15 | A2,9,28,32,B,C |
| 1.5 | 42 | F | Y (1) | Y | 3,24 | 7,60 | 4,15 | A1,2,10,11,19,28,36,43,B,C,DR |
| 1.6 | 40 | M | Y (3) | Y | 1 | 8 | 17 | A2,3,9,10,11,19,28,43,80,B,C,DR,DQ |
| 1.7 | 38 | M | Y (1) | Y | 1,3 | 7,37 | 10,15 | A2,B |
| 1.8 | 45 | F | Y (1) | N | 1,24 | 8,62 | 13,17 | A2,3,10,11,28,30,31,32,33,74,B,C,DR,DQ |
| 1.9 | 50 | F | Y (1) | N | 33,74 | 18,45 | 1,11 | A1,2,3,9,10,11,28,32,36,80,B,C,DR,DQ |
| 1.10 | 50 | M | Y (1) | Y | 1,33 | 44,58 | 7,13 | A2,9,28,B,C,DR |
| 1.11 | 38 | F | Y (1) | Y | 11,26 | 18,45 | 15,17 | A2,9,28,B,DR,DQ |
| 1.12 | 47 | F | N | Y | 1,24 | 37,52 | 15 | A2,3,11,19,66,68,80,B,C |
| 1.13 | 53 | F | N | Y | 3,26 | 27,65 | 1,15 | A2,9,28,B,C,DR |
| 1.14 | 50 | M | Y (1) | N | 1 | 8,18 | 17 | A2,28,33,B,DR,DQ |
| 1.15 | 42 | M | N | Y | 29 | 7,27 | 8,15 | A1,2,9,10,11,28,31,32,36,74,B,C |
| 1.16 | 31 | M | Y (1) | Y | 11 | 12,44 | 5,11 | A2,28,B |
| 1.17 | 57 | F | N | Y | 3,32 | 27,35 | 10,14 | A2,9,28,B |
| 1.18 | 27 | M | Y (2) | | 11,33 | 35,44 | 1,8 | A1,2,9,10,19,68,B,C,DR,DQ |
| | | | | | | | | |
| Group 2 | | | | | | | | |
| 2.1 | 51 | M | Y (1) | Y | 1 | 57,63 | 13,17 | A3,9,11,26,31,B,C |
| 2.2 | 51 | M | Y (2) | Y | 3,68 | 64,57 | 7 | A1,30,31,32,33,74,B,DR,DQ |
| 2.3 | 48 | F | N | N | 1 | 8 | 15,17 | A9,10,11,32,80,B,C,DR |
| 2.4 | 37 | M | Y (1) | Y | 3,31 | 35,44 | 1,8 | A1,9,10,11,28,29,36,43,80,B,C,DR,DQ |
| 2.5 | 38 | F | Y (1) | Y | 1,24 | 55,60 | 7,14 | A23,30,32,B,C,DR,DQ |
| 2.6 | 37 | M | Y (1) | Y | 68,74 | 15,45 | 1,12 | A9,B,DR |
| 2.7 | 30 | F | Y (1) | Y | 23,74 | 35,72 | 11,15 | A29,B |
| 2.8 | 36 | F | N | N | 23,74 | 53 | 13,15 | A26,66,B |
| | | | | | | | | |
| Group 3 | | | | | | | | |
| 3.1 | 25 | M | N | Y | 1,11 | 7,55 | 4,15 | |
| 3.2 | 45 | F | N | N | 23 | 64,51 | 13 | |
| 3.3 | 34 | M | N | Y | 1,3 | 7,8 | 3,4 | |
| 3.4 | 27 | M | N | N | 29 | 7,44 | 1,7 | |
| 3.5 | 33 | M | N | N | 24,30 | 57,60 | 4,7 | |
| 3.6 | 35 | F | N | N | 3,30 | 18,62 | 15,17 | |
| 3.7 | 22 | M | N | N | 1,3 | 44,51 | 1,8 | |

Fig. 10 (Cont.)

| | | | | | | | | |
|---|---|---|---|---|---|---|---|---|
| 3.8 | 23 | F | N | N | 24,26 | 35,51 | 4,11 | |
| 3.9 | 36 | M | N | N | 3,34 | 7,35 | 13,15 | |
| 3.10 | 18 | F | N | N | 11,26 | 13,58 | 15,17 | |
| | | | | | | | | |
| Group 4 | | | | | | | | |
| 4.1 | 38 | F | N | Y | 2,68 | 71,60 | 7, 17 | A1,3,9,10,11,29,31,33,36,80,B |
| 4.2 | 39 | F | Y (2) | Y | 2,3 | 39,56 | 11,13 | A1,9,10,11,19,28,29,36,43,80,B,C,DR,DQ |
| 4.3 | 45 | F | Y (1) | Y | 2,32 | 27,62 | 15 | A10,11,30,31,33,36,74,80,B,C,DR,DQ |
| 4.4 | 50 | M | Y (1) | Y | 2 | 60,44 | 13,15 | A1,3,9,10,11,29,30,31,33,68,80,B,C,DR |
| 4.5 | 50 | F | Y (1) | Y | 2,24 | 62,57 | 14,15 | A1,3,10,11,19,36,43,68,74,80,C,DR,DQ |
| 4.6 | 50 | F | N | N | 2 | 44 | 11,15 | A1,32,34,66,B,DR |
| 4.7 | 32 | M | Y (1) | Y | 2,30 | 18,60 | 4,17 | A1,3,11,29,31,32,33,74,80,B,C,DR |
| 4.8 | 30 | F | Y (1) | Y | 2,26 | 52,62 | 4 | A1,3,9,11,19,35,74,80,B,C,DR,DQ |
| 4.9 | 29 | F | Y (1) | Y | 2 | 50,37 | 10,17 | A1,3,9,10,11,19,28,29,36,43,80,B,C,DR,DQ |
| | | | | | | | | |
| Group 5 | | | | | | | | |
| 5.1 | 41 | M | N | N | 1,2 | 8,39 | 4,8 | |
| 5.2 | 33 | M | N | Y | 2,3 | 7,51 | 1,103 | |
| 5.3 | 34 | M | Y (1) | Y | 2 | 18,62 | 15,17 | |
| 5.4 | 49 | M | N | N | 2,3 | 37,40 | 10,15 | |
| 5.5 | 50 | M | Y (1) | Y | 2 | 18,57 | 1,7 | |
| 5.6 | 22 | F | N | N | 2,11 | | 4 | |
| 5.7 | 27 | M | N | N | 2 | 18,60 | 1,17 | |
| 5.8 | 37 | F | N | N | 1,2 | 35,39 | 1,13 | |
| 5.9 | 40 | M | N | N | 2,68 | 7,27 | 8,15 | |
| 5.10 | 27 | M | N | N | 2 | 8,27 | 1,17 | |
| | | | | | | | | |

Peptides 39

<u>Sequences</u>: 192-206

H A V S D H E A T L R C W A L

Peptides 40

Sequences: 202-216

R C W A L S F Y P A E I T L T

Peptides 50 & 51

Sequences: 268-282 & 270-284

K P L T L* R W* E P S S Q P T I*
    L T L* R W* E P S S Q P T I* P I*

Peptides 52 & 53

<u>Sequences</u>: 280-294 & 282-296

P T I\* P I\* V\* G I\* I\* A G L\* V\* L F\*
    I\* P I\* V\* G I\* I\* A G L\* V\* L F\* G A

SEQUENCE LISTING

<160> NUMBER OF SEQ ID NOS: 103

<210> SEQ ID NO 1
<211> LENGTH: 365
<212> TYPE: PRT
<213> ORGANISM: Homo sapiens

<400> SEQUENCE: 1

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Gly Glu Thr Arg Lys Val Lys Ala His Ser Gln
                85                  90                  95

Thr His Arg Val Asp Leu Gly Thr Leu Arg Gly Tyr Tyr Asn Gln Ser
            100                 105                 110

Glu Ala Gly Ser His Thr Val Gln Arg Met Tyr Gly Cys Asp Val Gly
        115                 120                 125

Ser Asp Trp Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
        195                 200                 205

Pro Lys Thr His Met Thr His His Ala Val Ser Asp His Glu Ala Thr
    210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Val Gln His Glu
        275                 280                 285

Gly Leu Pro Lys Pro Leu Thr Leu Arg Trp Glu Pro Ser Ser Gln Pro
    290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Ser Gln Ala Ala Ser Ser Asp Ser
            340                 345                 350

Ala Gln Gly Ser Asp Val Ser Leu Thr Ala Cys Lys Val
        355                 360                 365

<210> SEQ ID NO 2
<211> LENGTH: 341
<212> TYPE: PRT
<213> ORGANISM: Homo sapiens

<400> SEQUENCE: 2

```
Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Pro Thr Ile Pro Ile Val Gly Ile Ile
        275                 280                 285

Ala Gly Leu Val Leu Phe Gly Ala Val Ile Thr Gly Ala Val Val Ala
    290                 295                 300

Ala Val Met Trp Arg Arg Lys Ser Ser Asp Arg Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala Cys Lys Val
            340
```

<210> SEQ ID NO 3
<211> LENGTH: 3287
<212> TYPE: DNA
<213> ORGANISM: Homo sapiens

```
<400> SEQUENCE: 3
ggattcccca actccgcagt ttcttttctc cctctcccaa cctatgtagg gtccttcttc      60
ctggatactc acgacgcgga cccagttctc actcccatcg ggtgtcgggt ttccagagaa     120
gccaatcagt gtcgtcgcgg tcgcggttct aaagtccgca cgcacccacc gggactcaga     180
ttctccccag acgccgagga tggccgtcat ggcgccccga accctcgtcc tgctactctc     240
gggggctctg gccctgaccc agacctgggc gggtgagtgc gggtcggga gggaaacggc      300 ctctgtgggg agaagcaacg ggcccgcctg gcggggcgc aggacccggg aagccgcgcc      360
gggaggaggg tcggcgggt ctcagccact cctcgtcccc aggctctcac tccatgaggt      420
atttcttcac atccgtgtcc cggcccggcc gcggggagcc ccgcttcatc gcagtgggct     480
acgtggacga cacgcagttc gtgcggttcg acagcgacgc cgcgagccag aggatggagc     540
cgcgggcgcc gtggatagag caggagggtc cggagtattg ggacggggag acacggaaag     600
tgaaggccca ctcacagact caccgagtgg acctgggac cctgcgcggc tactacaacc      660
agagcgaggc cggtgagtga cccggcccg gggcgcaggt cacgacctct catccccac      720 ggacgggcca ggtcgcccac agtctccggg tccgagatcc gccccgaagc cgcgggaccc     780 cgagacccttt gccccgggag aggcccaggc gcctttaccc ggtttcattt tcagtttagg     840
ccaaaaatcc ccccaggttg gtcggggcgg ggcggggctc gggggaccgg gctgaccgcg     900
gggtccgggc caggttctca caccgtccag aggatgtatg gctgcgacgt ggggtcggac     960
tggcgcttcc tccgcgggta ccaccagtac gcctacgacg gcaaggatta catcgccctg    1020
aaagaggacc tgcgctcttg gaccgcggcg gacatggcag ctcagaccac caagcacaag    1080
tgggaggcgg cccatgtggc ggagcagttg agagcctacc tggagggcac gtgcgtggag    1140
tggctccgca gatacctgga gaacgggaag gagacgctgc agcgcacggg taccaggggc    1200
cacggggcgc ctccctgatc gcctgtagat ctcccgggct ggcctccac aaggagggga     1260 gacaattggg accaacacta gaatatcgcc ctccctctgg tcctgaggga gggaatcct     1320 cctgggtttc cagatcctgt accagagagt gactctgagg ttccgccctg ctctctgaca    1380
caattaaggg ataaaatctc tgaaggaatg acgggaagac gatccctcga atactgatga    1440
gtggttccct ttgacacaca caggcagcag ccttgggccc gtgacttttc ctctcaggcc    1500
ttgttctctg cttcacactc aatgtgtgtg ggggtctgag tccagcactt ctgagtcctt    1560
cagcctccac tcaggtcagg accagaagtc gctgttccct cttcagggac tagaattttc    1620
cacggaatag gagattatcc caggtgcctg tgtccaggct ggtgtctggg ttctgtgctc    1680
ccttccccat cccaggtgtc ctgtccattc tcaagatagc cacatgtgtg ctggaggagt    1740
gtcccatgac agatgcaaaa tgcctgaatg atctgactct tcctgacaga cgcccccaaa    1800
acgcatatga ctcaccacgc tgtctctgac catgaagcca ccctgaggtg ctgggccctg    1860
agcttctacc ctgcggagat cacactgacc tggcagcggg atggggagga ccagaccag     1920 gacacggagc tcgtggagac caggcctgca gggatggaa ccttccagaa gtgggcggct     1980
gtggtggtgc cttctggaca ggagcagaga tacacctgcc atgtgcagca tgagggtttg    2040
cccaagcccc tcaccctgag atgggtaag agggagacg gggtgtcat gtcttttagg       2100 gaaagcagga gcctctctga cctttagcag ggtcagggcc cctcaccttc ccctcttttc    2160
ccagagccgt cttcccagcc caccatcccc atcgtgggca tcattgctgg cctggttctc    2220
tttggagctg tgatcactgg agctgtggtc gctgctgtga tgtggaggag gaagagctca    2280
ggtggggaag gggtgaaggg tgggtctgag atttcttgtc tcactgaggg ttccaagacc    2340
```

```
caggtagaag tgtgccctgc ctcgttactg ggaagcacca cccacaatta tgggcctacc    2400
cagcctgggc cctgtgtgcc agcacttact cttttgtaaa gcacctgtta aaatgaagga    2460
cagatttatc accttgatta cagcggtgat gggacctgat cccagcagtc acaagtcaca    2520
ggggaaggtc cctgaggacc ttcaggaggg cggttggtcc aggacccaca cctgctttct    2580
tcatgtttcc tgatcccgcc ctgggtctgc agtcacacat ttctggaaac ttctctgagg    2640
tccaagactt ggaggttcct ctaggacctt aaggccctga ctcctttctg gtatctcaca    2700
ggacattttc ttcccacaga tagaaaagga gggagctact ctcaggctgc aagtaagtat    2760
gaaggaggct gatgcctgag gtccttggga tattgtgttt gggagcccat gggggagctc    2820
acccacccca caattcctcc tctagccaca tcttctgtgg gatctgacca ggttctgttt    2880
ttgttctacc ccaggcagtg acagtgccca gggctctgat gtgtctctca cagcttgtaa    2940
aggtgagagc ctggagggcc tgatgtgtgt tgggtgttgg gcggaacagt ggacacagct    3000
gtgctatggg gtttctttcc attggatgta ttgagcatgc gatgggctgt ttaaagtgtg    3060
acccctcact gtgacagata cgaatttgtt catgaatatt ttttctata gtgtgagaca     3120 gctgccttgt gtgggactga gaggcaagag ttgttcctgc ccttcccttt gtgacttgaa    3180
gaaccctgac tttgtttctg caaaggcacc tgcatgtgtc tgtgttcgtg taggcataat    3240
gtgaggaggt ggggagacca ccccacccccc atgtccacca tgaccct                 3287
```

```
<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

His Ser Met Arg Tyr Phe Phe Thr Ser Val Ser Arg Pro Gly Arg
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met Arg Tyr Phe Phe Thr Ser Val Ser Arg Pro Gly Arg Gly Glu
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Ser Val Ser Arg Pro Gly Arg Gly Glu Pro Arg Phe Ile Ala
1               5                   10                  15

<210> SEQ ID NO 7
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 7

Pro Arg Phe Ile Ala Val Gly Tyr Val Asp Asp Thr Gln Phe Val
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Ala Val Gly Tyr Val Asp Asp Thr Gln Phe Val Arg Phe Asp
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Gly Tyr Val Asp Asp Thr Gln Phe Val Arg Phe Asp Ser Asp
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Gln Phe Val Arg Phe Asp Ser Asp Ala Ala Ser Gln Arg Met
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Arg Phe Asp Ser Asp Ala Ala Ser Gln Arg Met Glu Pro Arg
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Gln Arg Met Glu Pro Arg Ala Pro Trp Ile Glu Gln Glu Gly Pro
1               5                   10                  15
```

```
<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Pro Trp Ile Glu Gln Glu Gly Pro Glu Tyr Trp Asp Gly Glu
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Pro Glu Tyr Trp Asp Gly Glu Thr Arg Lys Val Lys Ala His Ser
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Lys Val Lys Ala His Ser Gln Thr His Arg Val Asp Leu Gly
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

His Arg Val Asp Leu Gly Thr Leu Arg Gly Tyr Tyr Asn Gln Ser
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Asp Leu Gly Thr Leu Arg Gly Tyr Tyr Asn Gln Ser Glu Ala
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18
```

```
Gly Thr Leu Arg Gly Tyr Tyr Asn Gln Ser Glu Ala Gly Ser His
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Gly Tyr Tyr Asn Gln Ser Glu Ala Gly Ser His Thr Val Gln
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

His Thr Val Gln Arg Met Tyr Gly Cys Asp Val Gly Ser Asp Trp
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Val Gln Arg Met Tyr Gly Cys Asp Val Gly Ser Asp Trp Arg Phe Leu
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Cys Asp Val Gly Ser Asp Trp Arg Phe Leu Arg Gly Tyr His Gln
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Asp Trp Arg Phe Leu Arg Gly Tyr His Gln Tyr Ala Tyr Asp
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
```

-continued

```
    peptide

<400> SEQUENCE: 24

Trp Arg Phe Leu Arg Gly Tyr His Gln Tyr Ala Tyr Asp Gly Lys
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Gly Tyr His Gln Tyr Ala Tyr Asp Gly Lys Asp Tyr Ile Ala
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

His Gln Tyr Ala Tyr Asp Gly Lys Asp Tyr Ile Ala Leu Lys Glu
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Tyr Ala Tyr Asp Gly Lys Asp Tyr Ile Ala Leu Lys Glu Asp Leu
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Asp Tyr Ile Ala Leu Lys Glu Asp Leu Arg Ser Trp Thr Ala
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ile Ala Leu Lys Glu Asp Leu Arg Ser Trp Thr Ala Ala Asp Met
1               5                   10                  15

<210> SEQ ID NO 30
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Glu Asp Leu Arg Ser Trp Thr Ala Ala Asp Met Ala Ala Gln Thr
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Ser Trp Thr Ala Ala Asp Met Ala Ala Gln Thr Thr Lys His
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Asp Met Ala Ala Gln Thr Thr Lys His Lys Trp Glu Ala Ala
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

His Lys Trp Glu Ala Ala His Val Ala Glu Gln Leu Arg Ala Tyr
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala His Val Ala Glu Gln Leu Arg Ala Tyr Leu Glu Gly Thr Cys
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Glu Gln Leu Arg Ala Tyr Leu Glu Gly Thr Cys Val Glu Trp Leu
1               5                   10                  15
```

```
<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ala Tyr Leu Glu Gly Thr Cys Val Glu Trp Leu Arg Arg Tyr
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Thr Cys Val Glu Trp Leu Arg Arg Tyr Leu Glu Asn Gly Lys Glu
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Val Glu Trp Leu Arg Arg Tyr Leu Glu Asn Gly Lys Glu Thr Leu
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Arg Tyr Leu Glu Asn Gly Lys Glu Thr Leu Gln Arg Thr Asp
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Thr Leu Gln Arg Thr Asp Ala Pro Lys Thr His Met Thr His
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 41

Thr His Met Thr His His Ala Val Ser Asp His Glu Ala Thr Leu
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

His Ala Val Ser Asp His Glu Ala Thr Leu Arg Cys Trp Ala Leu
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Cys Trp Ala Leu Ser Phe Tyr Pro Ala Glu Ile Thr Leu Thr
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Leu Ser Phe Tyr Pro Ala Glu Ile Thr Leu Thr Trp Gln Arg Asp
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Glu Ile Thr Leu Thr Trp Gln Arg Asp Gly Glu Asp Gln Thr
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Leu Thr Trp Gln Arg Asp Gly Glu Asp Gln Thr Gln Asp Thr Glu
1               5                   10                  15

<210> SEQ ID NO 47
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 47

Thr Glu Leu Val Glu Thr Arg Pro Ala Gly Asp Gly Thr Phe Gln
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Thr Phe Gln Lys Trp Ala Ala Val Val Pro Ser Gly Gln
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Phe Gln Lys Trp Ala Ala Val Val Val Pro Ser Gly Gln Glu Gln Arg
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ala Ala Val Val Val Pro Ser Gly Gln Glu Gln Arg Tyr Thr Cys
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Glu Gln Arg Tyr Thr Cys His Val Gln His Glu Gly Leu Pro Lys Pro
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Glu Gly Leu Pro Lys Pro Leu Thr Leu Arg Trp Glu Pro Ser Ser
1               5                   10                  15
```

```
<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Lys Pro Leu Thr Leu Arg Trp Glu Pro Ser Ser Gln Pro Thr Ile
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Leu Thr Leu Arg Trp Glu Pro Ser Ser Gln Pro Thr Ile Pro Ile
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Pro Thr Ile Pro Ile Val Gly Ile Ile Ala Gly Leu Val Leu Phe
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ile Pro Ile Val Gly Ile Ile Ala Gly Leu Val Leu Phe Gly Ala
1               5                   10                  15

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Lys Pro Leu Thr Leu Arg Trp Glu Pro Ser Ser Gln Pro Thr Ile Pro
1               5                   10                  15

Ile

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 58

Pro Thr Ile Pro Ile Val Gly Ile Ile Ala Gly Leu Val Leu Phe Gly
1               5                   10                  15

Ala

<210> SEQ ID NO 59
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Thr Phe Gln Lys Trp Ala Ala Val Val Val Pro Ser Gly Gln Glu
1               5                   10                  15

Gln Arg

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

His Pro Ile Ser Asp His Glu Ala Thr Leu Arg Cys Trp Ala Leu
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

His Pro Val Ser Asp His Glu Ala Thr Leu Arg Cys Trp Ala Leu
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

His Pro Val Ser Asp His Glu Val Thr Leu Arg Cys Trp Ala Leu
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Cys Trp Ala Leu Gly Phe Tyr Pro Ala Glu Ile Thr Leu Thr
1               5                   10                  15
```

```
<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Lys Pro Leu Thr Leu Arg Trp Glu Leu Ser Ser Gln Pro Thr Ile Pro
1               5                   10                  15

Ile

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Pro Thr Ile Pro Ile Val Gly Ile Ile Ala Gly Leu Val Leu Leu Gly
1               5                   10                  15

Ala

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Lys Pro Leu Thr Leu Lys Trp Glu Pro Ser Ser Gln Pro Thr Ile Pro
1               5                   10                  15

Ile

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Lys Pro Leu Thr Leu Arg Trp Glu Pro Ser Ser Gln Pro Thr Val Pro
1               5                   10                  15

Ile

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Pro Leu Thr Leu Arg Trp Glu Pro Ser Ser Gln Pro Thr Val His
1               5                   10                  15

Ile
```

```
<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Pro Thr Val Pro Ile Val Gly Ile Ile Ala Gly Leu Val Leu Leu Gly
1               5                   10                  15

Ala

<210> SEQ ID NO 70
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Pro Thr Val His Ile Val Gly Ile Ile Ala Gly Leu Val Leu Phe Gly
1               5                   10                  15

Ala

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Pro Thr Ile Pro Ile Val Gly Ile Ile Ala Gly Leu Ala Val Leu Ala
1               5                   10                  15

Val

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Pro Thr Val Pro Ile Val Gly Ile Ile Ala Gly Leu Ala Val Leu Ala
1               5                   10                  15

Val

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Thr Phe Gln Lys Trp Ala Ala Val Val Val Pro Ser Gly Glu Glu
1               5                   10                  15

Gln Arg
```

```
<210> SEQ ID NO 74
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Thr Phe Gln Lys Trp Ala Ser Val Val Pro Ser Gly Gln Glu
1               5                   10                  15

Gln Arg

<210> SEQ ID NO 75
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
cactccatga ggtatttctt cacatccgtg tcccggcccg gccgc              45

<210> SEQ ID NO 76
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
atgaggtatt tcttcacatc cgtgtcccgg cccggccgcg gggag              45

<210> SEQ ID NO 77
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
cacaagtggg aggcggccca tgtggcggag cagttgagag cctac              45

<210> SEQ ID NO 78
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
cacgctgtct ctgaccatga agccaccctg aggtgctggg ccctg              45

<210> SEQ ID NO 79
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
aggtgctggg ccctgagctt ctaccctgcg gagatcacac tgacc              45
```

```
<210> SEQ ID NO 80
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
aagcccctca ccctgagatg ggagccgtct cccagccca ccatc              45

<210> SEQ ID NO 81
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
ctcaccctga gatgggagcc gtcttcccag cccaccatcc ccatc              45

<210> SEQ ID NO 82
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
cccaccatcc ccatcgtggg catcattgct ggcctggttc tcttt              45

<210> SEQ ID NO 83
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
atccccatcg tgggcatcat tgctggcctg gttctctttg gagct              45

<210> SEQ ID NO 84
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
ggaaccttcc agaagtgggc ggctgtggtg gtgccttctg gacag              45

<210> SEQ ID NO 85
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ttccagaagt gggcggctgt ggtggtgcct tctggacagg agcagaga          48

<210> SEQ ID NO 86
```

```
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
aagcccctca ccctgagatg ggagccgtct tcccagccca ccatccccat c            51

<210> SEQ ID NO 87
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
cccaccatcc ccatcgtggg catcattgct ggcctggttc tctttggagc t            51

<210> SEQ ID NO 88
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
ggaaccttcc agaagtgggc ggctgtggtg gtgccttctg acaggagca gaga          54

<210> SEQ ID NO 89
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
tcggactggc gcttcctccg cgggtaccac cagtacgcct acgac                   45

<210> SEQ ID NO 90
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
tggcgcttcc tccgcgggta ccaccagtac gcctacgacg gcaag                   45

<210> SEQ ID NO 91
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
caccccatct ctgaccatga ggccaccctg aggtgctggg ccctg                   45

<210> SEQ ID NO 92
<211> LENGTH: 51
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 92
aagcccctca ccctgagatg ggagccttct tcccagccca ccatccccat c              51

<210> SEQ ID NO 93
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
cccaccatcc ccatcgtggg catcattgct ggcctggttc tccttggagc t              51

<210> SEQ ID NO 94
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
aggtgctggg ccctgggctt ctaccctgcg gagatcacac tgacc                    45

<210> SEQ ID NO 95
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
ggaaccttcc agaagtgggc ggctgtggtg gtgccttctg agaggagca gaga           54

<210> SEQ ID NO 96
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
ggaaccttcc agaagtgggc gtctgtggtg gtgccttctg acaggagca gaga           54

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Pro Lys Tyr Val Lys Gln Asn Thr Leu Lys Leu Ala Thr
1               5                   10

<210> SEQ ID NO 98
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 98

Ala Ala Tyr Ala Ala Ala Lys Ala Ala Ala Leu Ala Ala
1               5                   10

<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ala Lys Thr Ile Ala Tyr Asp Glu Glu Ala Arg Arg Gly Leu Glu
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Thr Glu Arg Val Arg Leu Val Thr Arg His Ile Tyr Asn Arg Glu Glu
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Glu Ala Glu Gln Leu Arg Ala Tyr Leu Asp Gly Thr Gly Val Glu
1               5                   10                  15

<210> SEQ ID NO 102
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Glu Ser Trp Gly Ala Val Trp Arg Ile Asp Thr Pro Asp Lys Leu Thr
1               5                   10                  15

Gly Pro Phe Thr
            20

<210> SEQ ID NO 103
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 103

Ala Gly Asp Leu Leu Ala Ile Glu Thr Asp Lys Ala Thr Ile
1               5                   10
```

HLA PEPTIDE THERAPY

FIELD OF THE INVENTION

The present invention relates to peptide therapy, and particularly although not exclusively, to the use of peptide immunotherapy to treat or prevent allograft rejection. The invention extends to various constructs, and methods of using such constructs in treating transplant patients, for example, patients suffering from end stage renal failure (ESRF) who require a kidney transplant.

BACKGROUND OF THE INVENTION

The results of renal transplantation are good in the short and medium term. However, in the long term, kidneys are consistently lost as a consequence of chronic allograft (transplant) nephropathy. This is largely a consequence of two ongoing phenomena:—(i) chronic rejection; and (ii) calcineurin inhibitor nephrotoxicity. Both of these phenomena interact with a pre-existing determinant of outcome, i.e. chronic damage to the renal parenchyma established prior to and early post transplantation. Furthermore, the requirement for long term immunosuppression in transplant recipients has adverse consequences, such as increased susceptibility to infection and to malignancy.

The benefits of transplantation as treatment for patients suffering from ESRF are manifest both in quality of life and enhanced survival. However, a long wait to be transplanted can be frustrating for the individual and materially affect long-term outcome. A variety of factors determine the waiting time, but particularly important is the presence in the transplant recipient of antibodies that exhibit immunospecificity against polymorphic molecules known as human leukocyte antigens (HLA), present on potential donor organs. Anti-HLA antibodies produced by the transplant recipient can cause a very rapid onset or 'hyperacute' rejection of the transplant organ, and their presence must therefore be determined prior to transplantation. The potential recipient is then excluded from receiving a transplant bearing relevant HLA, and the patient must wait for an organ bearing HLA antigens to which antibodies are not produced. Anti-HLA antibodies may be stimulated by pregnancy, blood transfusion and transplantation. The use of erythropoetin has reduced transfusion, and enhanced HLA matching through organ sharing has reduced the stimulation of antibody synthesis by transplantation.

Nevertheless, the production of anti-HLA antibodies, i.e. "HLA sensitisation", remains a significant problem for transplantation. This is particularly evident in patients who have long-standing ESRF, often from a young age, who have heavy cumulative exposure to allogeneic (i.e foreign HLA). The formation of affinity-matured class switched anti-HLA antibodies by B lymphocytes requires the presence of T cell help. The presence of T cell help for antibody production implies the engagement of HLA by T cell receptors through the indirect pathway. CD4+ T lymphocytes can recognise allogeneic HLA through conventional mechanisms of uptake by autologous antigen presenting cells, processing to peptide and presentation in the context of self-MHC class II. This is called the indirect pathway of allorecognition. As well as its role in antibody formation, T cells are also thought to play a particularly important role in chronic rejection. The direct pathway of allorecognition is the cross-reaction of T cell receptor specific for self-MHC and nominal exogenous peptide on allogeneic MHC (with associated peptide). This is thought to be particularly important in acute rejection. The inventor of the present invention therefore considered that treatment to minimise, prevent or completely abolish the indirect pathway of allorecognition could be of considerable value both prior to and after receiving a transplant in order to reduce the likelihood of rejection and the synthesis of anti-HLA antibodies.

A long-term goal of immunological research in transplantation has been to develop antigen specific modulation of the immune response that would render non-specific immunosuppression unnecessary. Although a complete abrogation of the requirement for immunosuppression may be unrealistic, the inventor realised that any gain in specificity would be welcome.

Non-antigen specific immunosuppression seems to be of limited value in modulating chronic rejection and anti-HLA antibody synthesis. However, while the inventor does not wish to be bound by any hypothesis, they believe that antigen specific reduction or inhibition of indirect presentation could diminish chronic rejection and HLA antibody synthesis. By analogy with evidence in the field of allergy, the inventor speculates that treatments based on fragments of antigen, i.e. peptides, could prove beneficial.

SUMMARY OF THE INVENTION

Therefore, the inventor set out to develop a peptide immunotherapy technique that could modulate the indirect pathway of allorecognition in humans. They believe that this has the potential for antigen specific modulation of alloimmune responses. In order to test their hypothesis, they studied indirect allorecognition in patients in whom there was evidence of a specific indirect allogeneic response. The inventor therefore chose to investigate patients who had made an anti-HLA antibody of known specificity, since this implied the presence of a specific indirect alloresponse. The inventor based his studies on a common and problematic MHC class I antigen molecule, HLA-A2, which is illustrated in FIG. 1.

The inventor wanted to understand exactly which parts of this antigen molecule stimulate T lymphocytes through the indirect pathway, and could therefore help anti-HLA- A2 antibody synthesis in these patients. Hence, using bioinformatics, a series of 60 overlapping 15 mer peptides was designed, which corresponded to various regions of the HLA-A2 molecule, and which formed the basis of a so-called 'epitope map'. This 'map' of responses to HLA-A2 was thought likely to differ between individuals, determined by genetically controlled elements, such as HLA-DR and the nature of any prior exposure to HLA-A2, i.e. sensitisation. Surprisingy, of the 60 overlapping peptides that were designed, 7 peptides could not be synthesised due to technical difficulties in the synthesis procedure. While the inventor does not wish to be bound by any hypothesis, they believe that this was a consequence of the extreme hydrophobicity of the 7 peptides not synthesised.

The inventor wanted to understand exactly which parts of this antigen molecule stimulate T lymphocytes through the indirect pathway, and could therefore help anti-HLA-A2 antibody synthesis in these patients. Hence, using bioinformatics, a series of 60 overlapping 15mer peptides was designed, which corresponded to various regions of the HLA-A2 molecule, and which formed the basis of a so-called 'epitope map'. This 'map' of responses to HLA-A2 was thought likely to differ between individuals, determined by genetically controlled elements, such as HLA-DR and the nature of any prior exposure to HLA-A2, i.e. sensitisation. Surprisingly, of the 60 overlapping peptides that were designed, 7 peptides could not be synthesised due to technical difficulties in the synthesis procedure. While the inventor does not wish to be bound by any hypothesis, they believe that this was a consequence of the extreme hydrophobicity of the 7 peptides not synthesised.

The inventor studied the biochemistry of the 53 peptides, designated p1-p53, that were synthesised from HLA-A2, as listed in FIG. 3 in order to see which were most likely to act as stimulators through the indirect pathway of allorecognition by binding to MHC class II molecules, in particular HLA-DR. Using an ELISA based system, the inventor measured the binding affinity of these 53 overlapping peptides to a range of purified MHC class II molecules. The various MHC class II molecules that were tested included: DR1, DR3, DR4, DR7, DR11, DR13, DR15, DR51, DR52, DR53, DP0401, and DP0402. The inventor was surprised to find that peptides from several locations along the HLA-A2 molecule exhibited promiscuous binding to MHC class II. The inventor then carried out in vitro investigations using 30 of the peptides to stimulate peripheral blood mononuclear cells (PBMC) from 27 transplant-listed patients with known antibody sensitisation histories. Some patients tested had been pre-sensitised to HLA-A2, and therefore did produce anti-HLA-A2 antibodies, other patients had not been pre-sensitised to HLA-A2 but to other HLA antigens, and others had no anti-HLA-A2 antibodies. The subjects were also stratified according to their own expression of HLA-A2. Hence, the inventor hoped to systematically determine peptide epitopes to which an indirect alloimmune response had been made. These would form candidate therapeutic peptides for treatment of patients, to reverse and prevent sensitisation to HLA-A2. In order to count the number of patient's cells that made a response, the inventor used a technique to detect cytokine production from a single cell known as the "γ-interferon ELISPOT (enzyme-linked immunosorbent assay)".

To his surprise, the inventor found that peptides that were derived from, and corresponded to certain regions of the HLA-A2 molecule are likely to have a beneficial effect on transplant patients. To his greater surprise, the inventor found that peptides derived from the α3 domain and/or transmembrane domains of HLA-A2 are likely to have a beneficial effect on transplant patients. Hence, as a result of these data, the inventor believes that they are the first to discover and report a first medical use for HLA-A2 derived peptides or derivatives or analogues thereof.

The inventor chose HLA-A2 as a target antigen for their investigations, as this is the most common type in man (about 50%). They hypothesised that inhibition of T-cell help in the anti-HLA-A2 specific B-cell activation pathway would reduce the synthesis of anti-HLA-A2 antibodies. Hence, the inventor believes that the use of a peptide derived from HLA-A2 or a derivative or an analogue thereof will have a very wide range of therapeutic uses. For example, such therapeutic uses include treating medical conditions characterised by allosensitisation, such as in patients requiring repeated platelet transfusion.

The inventor has also shown that many of the polypeptides derived from HLA-A2 are also found in other MHC class I HLA proteins, particularly HLA-B.

Therefore, the invention provides a polypeptide consisting of less than 30 contiguous amino acids from the α3 domain and/or transmembrane domain of a MHC class I human leukocyte antigen (HLA), or a derivative or analogue thereof.

The invention also provides:
a nucleic acid molecule encoding a polypeptide, derivative or analogue according to the invention;
a recombinant vector containing a nucleic acid molecule of the invention;
a host cell comprising a recombinant vector of the invention;
a pharmaceutical composition comprising a therapeutically effective amount of a polypeptide, derivative or analogue of the invention or a nucleic acid molecule of the invention, and optionally a pharmaceutically acceptable vehicle;
a process for making a pharmaceutical composition comprising combining a therapeutically effective amount of a polypeptide, derivative or analogue of the invention or a nucleic acid molecule of and a pharmaceutically acceptable vehicle;
a polypeptide derived from a MHC class I HLA, or a derivative or analogue thereof, for use as a medicament;
a nucleic acid molecule encoding a polypeptide derived from a MHC class I HLA, or a derivative or analogue thereof, or a nucleic acid molecule that hybridizes to a nucleic acid molecule encoding a polypeptide derived from a MHC class I HLA, or a derivative or analogue thereof, or its complement under stringent conditions, for use as a medicament;
use of:
  (a) at least one polypeptide derived from a MHC class I HLA, or a derivative or analogue thereof;
  (b) at least one nucleic acid molecule encoding a polypeptide, derivative or analogue of (a); or
  (c) at least one nucleic acid molecule that hybridizes to a nucleic acid molecule of (b) or its complement under stringent conditions;
for the manufacture of a medicament for the treatment or prevention of a condition characterised by allosensitisation.
  a method of treating or preventing a condition characterised by allosensitisation, the method comprising administering to a subject in need of such treatment, a therapeutically effective amount of:
  (a) at least one polypeptide derived from a MHC class I HLA, or a derivative or analogue thereof;
  (b) at least one nucleic acid molecule encoding a polypeptide, derivative or analogue of (a); or
  (c) at least one nucleic acid molecule that hybridizes to a nucleic acid molecule of (b) or its complement under stringent conditions; and
an in vitro method of stimulating T cells, the method comprising contacting the T cells with:
  (a) a polypeptide derived from a MHC class I HLA, or a derivative or analogue thereof;
  (b) a nucleic acid molecule encoding a polypeptide, derivative or analogue of (a); or
  (c) a nucleic acid molecule that hybridizes to a nucleic acid molecule of (b) or its complement under stringent conditions;
under conditions which allow stimulation of the T cells and thereby stimulating the T cells.

DESCRIPTION OF THE FIGURES

FIG. 3 shows a Table listing 53 peptides (p1 to p53) (SEQ ID NOS 4-56, respectively in order of appearance) covering regions of HLA-A2, their molecular weight, and their actual sequence. The 53 peptides were used in Examples 1 and 2.

FIG. 4 shows data resulting from binding affinity studies in Example 1 of the 53 peptides shown in FIG. 2 to a range of purified MHC II molecules DR1, DR3, DR4, DR7, DR11, DR13, DR15, DR51-DRB5, DR52-DRB4, and DR53-DRB3

FIG. 5 shows a schematic representation of the extracellular portion of the human class MHC class I, HLA-A2, and peptide p39 (residues 192-206 of HLA-A2) (SEQ ID NO: 42).

FIG. 9 shows data resulting from the binding affinity studies in Example 1 of the 53 peptides shown in FIG. 2 to a range of purified MHC II molecules DR1, DR3, DR4, DR7, DR11, DR13, DR15, DR51-DRB5, DR52-DRB4, and DR53-DRB3. The IC50 expressed in nM were evaluated from at least three independent experiments for each of 53 different peptides.

Biotinylated reference peptides were good binders to the HLA-DR molecules and exhibited the following IC50: HA 306-318 (PKYVKQNTLKLAT (SEQ ID NO: 97)) for HLA-DRB1*0101 (1 nM; pH 6), HLADRB1* 0401 (22 nM; pH 6), HLA-DRB1*1101 (19 nM; pH 5) and HLA-DRB5*0101 (8 nM; pH 5.5); YKL (AAYAAAKAAALAA (SEQ ID NO: 98)) for HLADRB1*0701 (6 nM; pH 5); MT 2-16 (AKTIAYDEE-ARRGLE (SEQ ID NO: 99)) for DRB1*0301 (303 nM; pH 4.5); B1 21-36 (TERVRLVTRHIYNREE (SEQ ID NO: 100)) for HLA-DRB1*1301 (131 nM; pH 4.5); A3 152-166 (EAEQLRAYLDGTGVE (SEQ ID NO: 101)) for HLA-DRB1*1501 (59 nM; pH 4.5); LOL 191-210 (ES-WGAVWRIDTPDKLTGPFT (SEQ ID NO: 102)) for HLA-DRB3*0101 (20 nM; pH 5.5) and E2/E168 (AGDLLAIETDKATI (SEQ ID NO: 103)) for HLA-DRB4*0101 (27 nM; pH 5). * means adjacent pairs of peptides used in combination in subsequent functional assays.

FIG. 10 shows the age, sex, tissue type, transplantation, transfusion and sensitisation history of study subjects in Example 2. The different patient groups are defined on the basis of the presence of HLA-A2 in the subject and their production of antibodies to HLA-A2 or to other HLA. Group 1: HLA-A2 negative with antibodies to HLA-A2; Group 2: HLA-A2 negative with antibodies to none -A2 HLA; Group 3: HLA-A2 negative with no history of anti HLA antibody formation; Group 4: HLA-A2 positive with antibodies to none -A2 HLA; Group 5: HLA-A2 positive with no history of anti HLA antibody formation.

Figure 11:
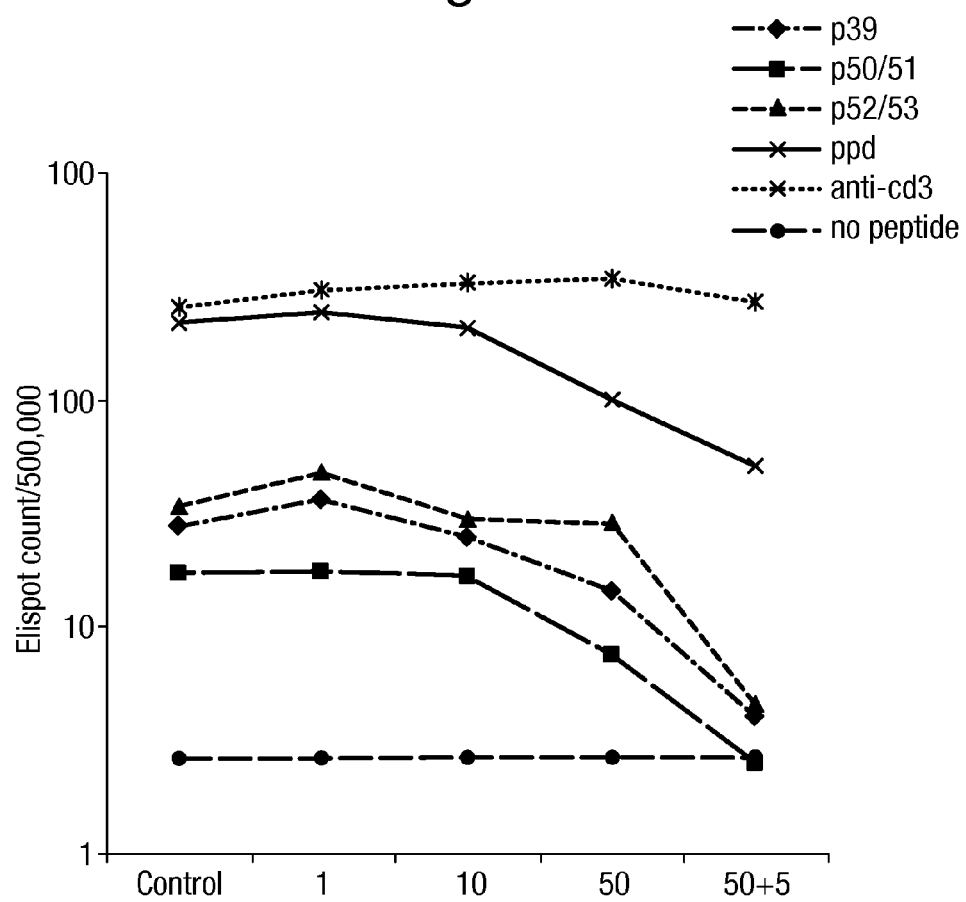

FIG. 11 shows a bar graph showing ELISPOT (enzyme-linked immunosorbent assay) count data of reactive cells/500,000 PBMCs in a single patient for the peptides studied in Example 2. The mean number of responding cells per well ($5 \times 10^5$ PBMCs) is shown for one subject cultured in the absence or presence of increasing concentrations (1, 10 & 50 µgml$^{-1}$) of antibody against MHC class II (Tu39, Becton Dickinson, Oxford, United Kingdom). Antibody against HLA-DR (L243 Becton Dickinson) at 50 µgml$^{-1}$ was added at the highest concentration of anti-MHC class II. PBMC's were cultured in the presence of peptide (p39 , P50/51 or p52/53) at 20 µgml$^{-1}$, PPD at 10 µgml$^{-1}$, the anti-CD3 positive control supplied with the γ-interferon ELISPOT plate (Mabtech) or medium alone.

Figure 2:
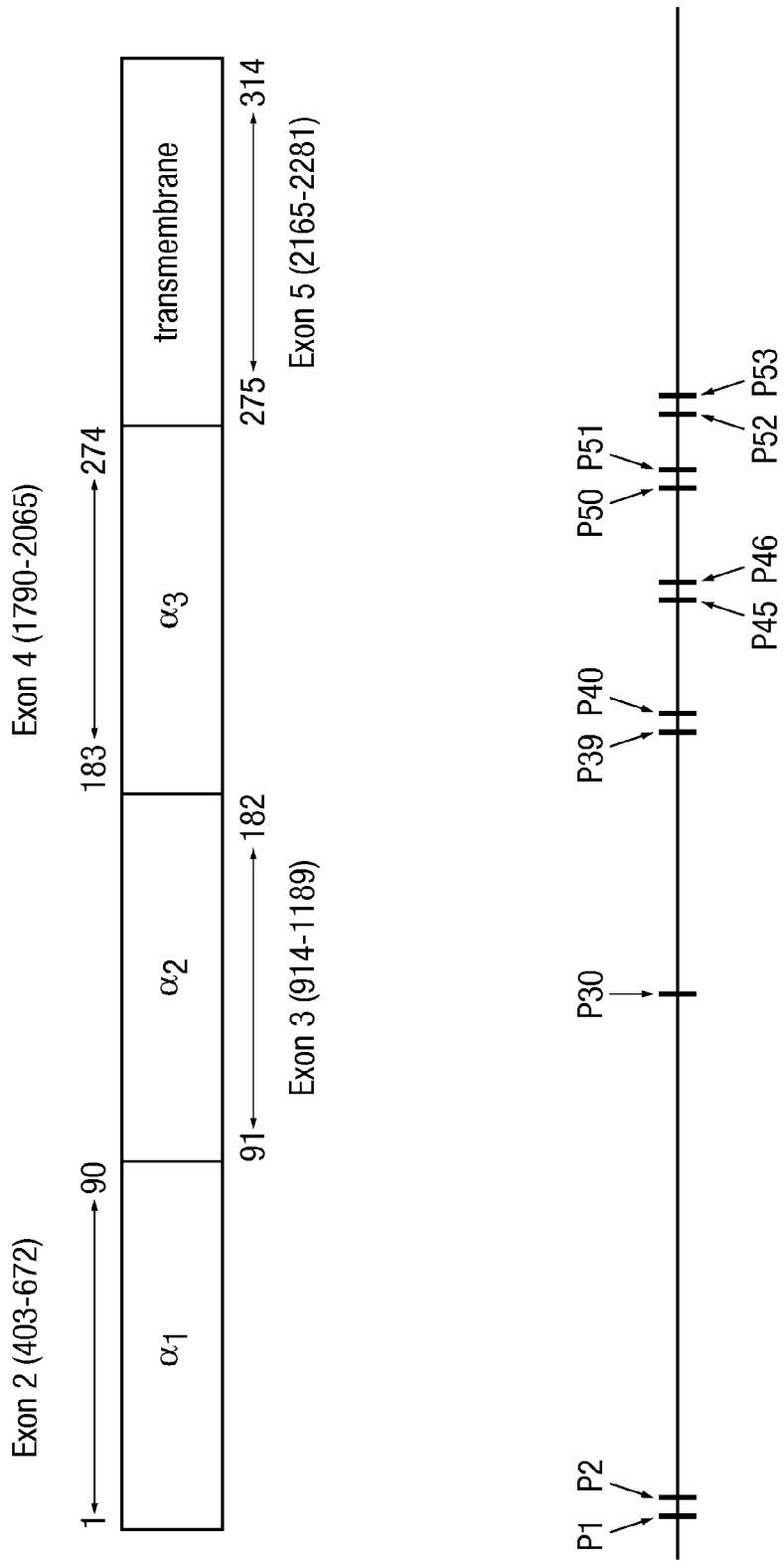
FIG. 2 shows a schematic representation of the extracellular portion of HLA-A2, showing amino acid and DNA sequences of the α1, α2, α3, and transmembrane domains.
Figure 12:
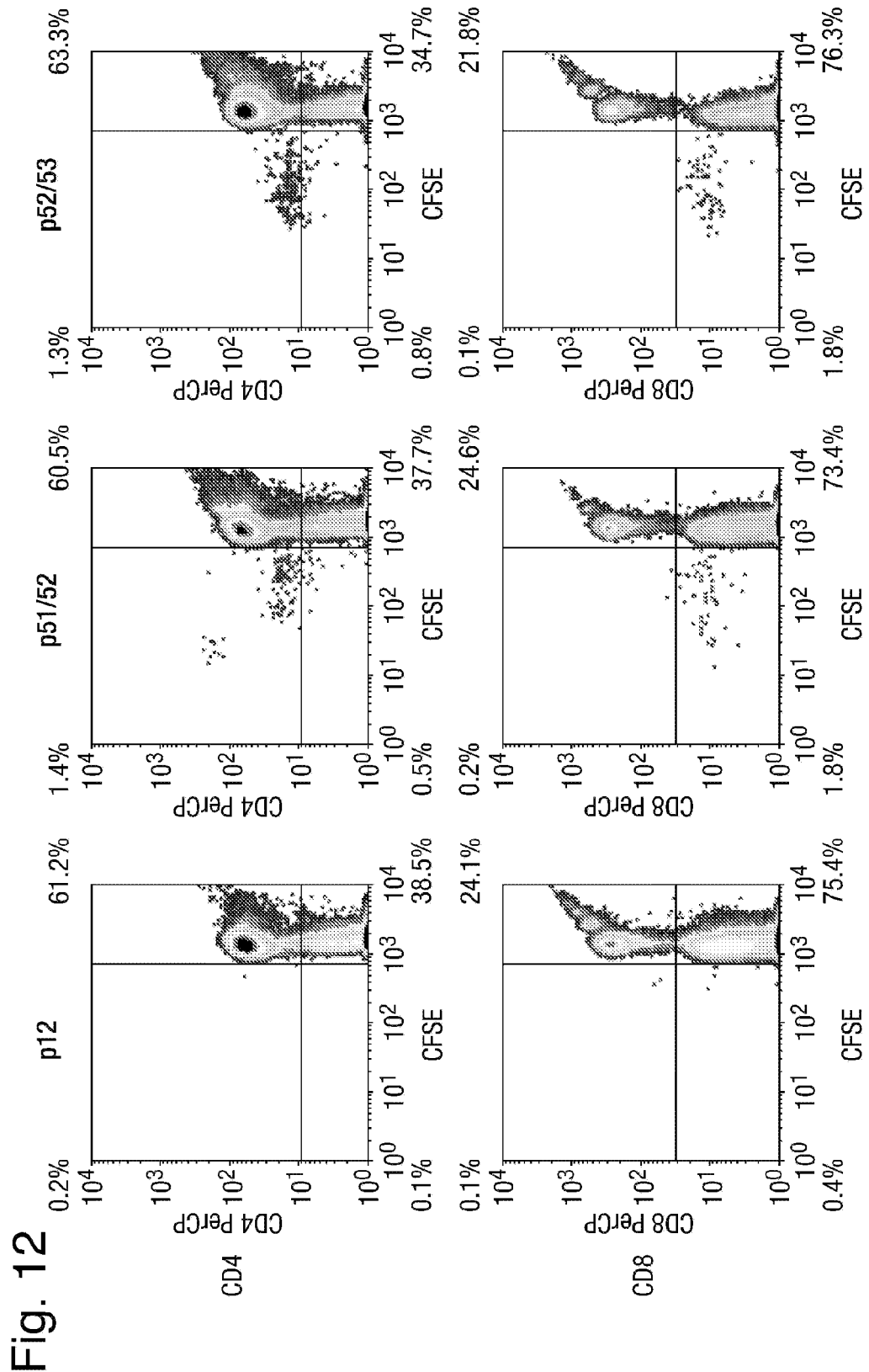

FIG. 12 shows proliferation of T cells in response to some of the peptides in FIG. 2. Mean γ-interferon ELISPOT frequencies per $5 \times 10^5$ PBMCs (y-axis) for each peptide or peptide pair (x-axis) are shown for individuals who made a response significantly greater than background. 21 different peptides or pairs of peptides were studied at a concentration of 20 µgml$^{-1}$ (shown) or 4 µgml$^{-1}$. Positive controls were ppd at 10 µgml$^{-1}$ or tetanus toxoid at 1 µgml$^{-1}$ or in some later experiments anti-CD3 supplied with the γ-interferon ELISPOT plate (Mabtech). The HLA-DR types of the responders are shown in parentheses.

Figure 13:
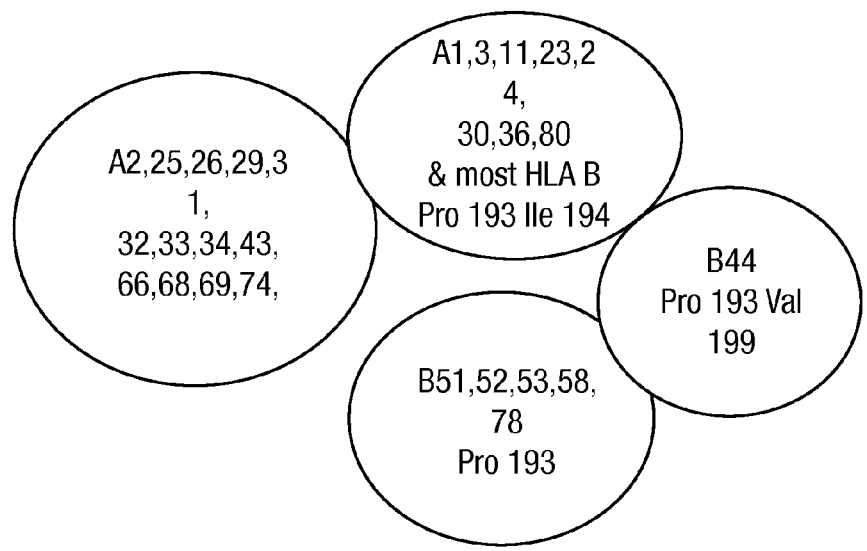

FIG. 13 shows a schematic representation of the peptide p39 (residues 192-206 of HLA-A2) (SEQ ID NO: 42). It also shows the difference(s) between p39 and the corresponding sequence in various HLA-B alleles.

Figure 14:
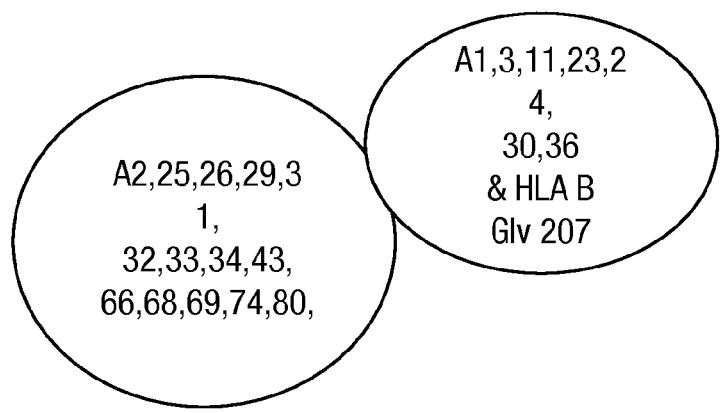

FIG. 14 shows a schematic representation of the peptide p40 (residues 202-216 of HLA-A2) (SEQ ID NO: 43). It also shows the difference(s) between p39 and the corresponding sequence in HLA-B.

Figure 15:
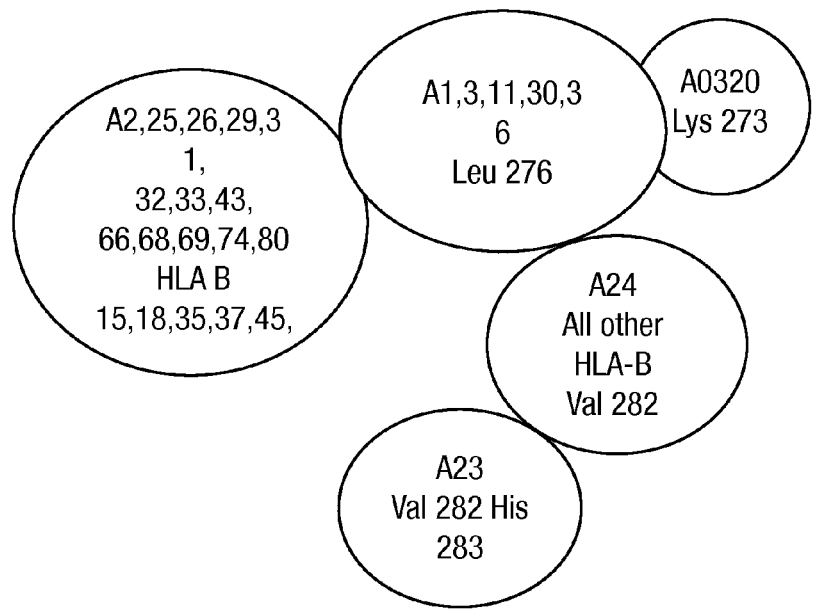

FIG. 15 shows a schematic representation of the peptides p50 (residues 268-282 of HLA-A2) (SEQ ID NO: 53) and p51 (residues 270-284 of HLA-A2) (SEQ ID NO: 54). It also shows the difference(s) between p39 and the corresponding sequence in various HLA-B alleles.

Figure 16:
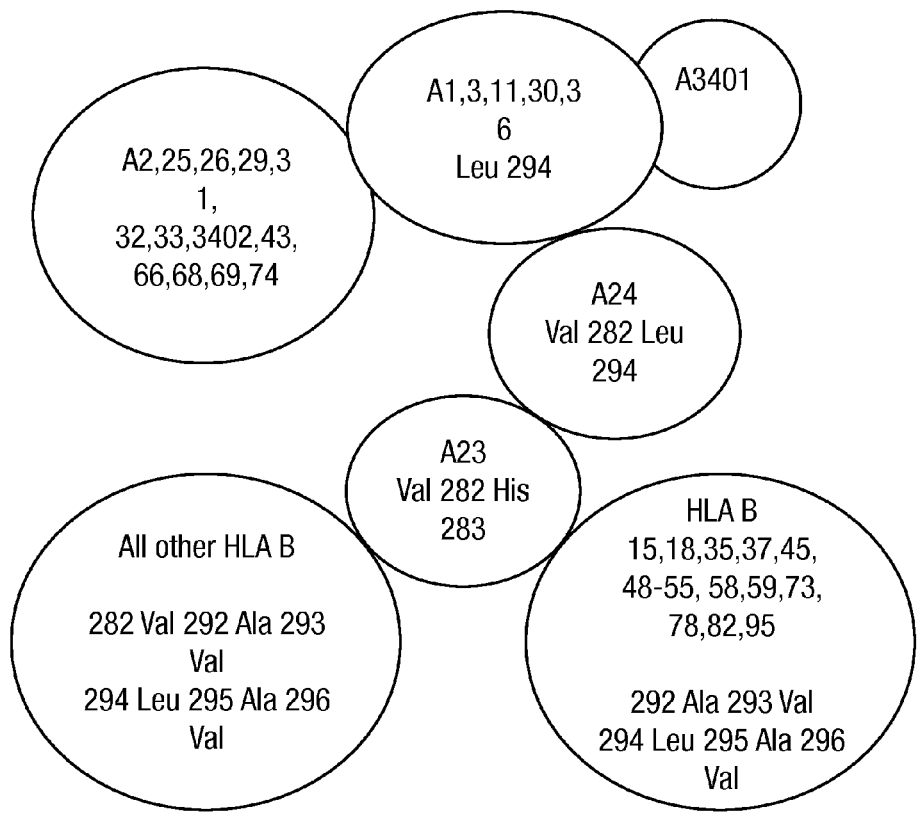

FIG. 16 shows a schematic representation of the peptides p52 (residues 280-294 of HLA-A2) (SEQ ID NO: 55) and p53 (residues 282-296 of HLA-A2) (SEQ ID NO: 56). It also shows the difference(s) between p39 and the corresponding sequence in various HLA-B alleles.

DESCRIPTION OF THE SEQUENCES

SEQ ID NO: 1 shows the full-length amino acid sequence of human MHC class I antigen, HLA-A2, (i.e. the HLA*020101 allele).

SEQ ID NO: 2 shows the mature version of the amino acid sequence of human MHC class I antigen, HLA-A2, (i.e. the HLA*020101 allele). In other words, SEQ ID NO: 2 shows the sequence of HLA-A2 without its signal sequence. SEQ ID NO: 2 corresponds to residues 25-365 of SEQ ID NO: 1.

SEQ ID NO: 3 shows the nucleic acid sequence encoding the full length human MHC class I antigen, HLA-A2, (i.e. the HLA*020101 allele) shown in SEQ ID NO: 1.

SEQ ID NO: 4 shows the amino acid sequence of p1 in Figure 3.

SEQ ID NO: 5 shows the amino acid sequence of p2 in Figure 3.

SEQ ID NO: 6 shows the amino acid sequence of p3 in Figure 3.

SEQ ID NO: 7 shows the amino acid sequence of p4 in Figure 3.

SEQ ID NO: 8 shows the amino acid sequence of p5 in Figure 3.

SEQ ID NO: 9 shows the amino acid sequence of p6 in Figure 3.

SEQ ID NO: 10 shows the amino acid sequence of p7 in Figure 3.

SEQ ID NO: 11 shows the amino acid sequence of p8 in Figure 3.

SEQ ID NO: 12 shows the amino acid sequence of p9 in Figure 3.

SEQ ID NO: 13 shows the amino acid sequence of p10 in Figure 3.

SEQ ID NO: 14 shows the amino acid sequence of p11 in Figure 3.
SEQ ID NO: 15 shows the amino acid sequence of p12 in Figure 3.
SEQ ID NO: 16 shows the amino acid sequence of p13 in Figure 3.
SEQ ID NO: 17 shows the amino acid sequence of p14 in Figure 3.
SEQ ID NO: 18 shows the amino acid sequence of p15 in Figure 3.
SEQ ID NO: 19 shows the amino acid sequence of p16 in Figure 3.
SEQ ID NO: 20 shows the amino acid sequence of p17 in Figure 3.
SEQ ID NO: 21 shows the amino acid sequence of p18 in Figure 3.
SEQ ID NO: 22 shows the amino acid sequence of p19 in Figure 3.
SEQ ID NO: 23 shows the amino acid sequence of p20 in Figure 3.
SEQ ID NO: 24 shows the amino acid sequence of p21 in Figure 3.
SEQ ID NO: 25 shows the amino acid sequence of p22 in Figure 3.
SEQ ID NO: 26 shows the amino acid sequence of p23 in Figure 3.
SEQ ID NO: 27 shows the amino acid sequence of p24 in Figure 3.
SEQ ID NO: 28 shows the amino acid sequence of p25 in Figure 3.
SEQ ID NO: 29 shows the amino acid sequence of p26 in Figure 3.
SEQ ID NO: 30 shows the amino acid sequence of p27 in Figure 3.
SEQ ID NO: 32 shows the amino acid sequence of p29 in Figure 3.
SEQ ID NO: 33 shows the amino acid sequence of p30 in Figure 3.
SEQ ID NO: 34 shows the amino acid sequence of p31 in Figure 3.
SEQ ID NO: 35 shows the amino acid sequence of p32 in Figure 3.
SEQ ID NO: 36 shows the amino acid sequence of p33 in Figure 3.
SEQ ID NO: 37 shows the amino acid sequence of p34 in Figure 3.
SEQ ID NO: 38 shows the amino acid sequence of p35 in Figure 3.
SEQ ID NO: 39 shows the amino acid sequence of p36 in Figure 3.
SEQ ID NO: 40 shows the amino acid sequence of p37 in Figure 3.
SEQ ID NO: 41 shows the amino acid sequence of p38 in Figure 3.
SEQ ID NO: 42 shows the amino acid sequence of p39 in Figure 3.
SEQ ID NO: 43 shows the amino acid sequence of p40 in Figure 3.
SEQ ID NO: 44 shows the amino acid sequence of p41 in Figure 3.
SEQ ID NO: 45 shows the amino acid sequence of p42 in Figure 3.
SEQ ID NO: 46 shows the amino acid sequence of p43 in Figure 3.
SEQ ID NO: 47 shows the amino acid sequence of p44 in Figure 3.
SEQ ID NO: 48 shows the amino acid sequence of p45 in Figure 3.
SEQ ID NO: 49 shows the amino acid sequence of p46 in Figure 3.
SEQ ID NO: 50 shows the amino acid sequence of p47 in Figure 3.
SEQ ID NO: 51 shows the amino acid sequence of p48 in Figure 3.
SEQ ID NO: 52 shows the amino acid sequence of p49 in Figure 3.
SEQ ID NO: 53 shows the amino acid sequence of p50 in Figure 3.
SEQ ID NO: 54 shows the amino acid sequence of p51 in Figure 3.
SEQ ID NO: 55 shows the amino acid sequence of p52 in Figure 3.
SEQ ID NO: 56 shows the amino acid sequence of p53 in Figure 3.
SEQ ID NO: 57 shows the amino acid sequence of p50/51 (overlapping amino acids 268-282 and 270-284 SEQ ID NO: 2).
SEQ ID NO: 58 shows the amino acid sequence of p52/53 (overlapping amino acids 280-294 and 282-296 of SEQ ID NO: 2).
SEQ ID NO: 59 shows the amino acid sequence of p45/46 (overlapping amino acids 239-253 & 241-256 of SEQ ID NO: 1).
SEQ ID NO: 60 shows the amino acid sequence of p39 analogue 1.
SEQ ID NO: 61 shows the amino acid sequence of p39 analogue 2.
SEQ ID NO: 62 shows the amino acid sequence of p39 analogue 3.
SEQ ID NO: 63 shows the amino acid sequence of p40 analogue.
SEQ ID NO: 64 shows the amino acid sequence of p50/51 analogue 1.
SEQ ID NO: 65 shows the amino acid sequence of p52/53 analogue 1.
SEQ ID NO: 66 shows the amino acid sequence of p50/51 analogue 2.
SEQ ID NO: 67 shows the amino acid sequence of p50/51 analogue 3.
SEQ ID NO: 68 shows the amino acid sequence of p50/51 analogue 4.
SEQ ID NO: 69 shows the amino acid sequence of p52/53 analogue 2.
SEQ ID NO: 70 shows the amino acid sequence of p52/53 analogue 3.
SEQ ID NO: 71 shows the amino acid sequence of p52/53 analogue 4.
SEQ ID NO: 72 shows the amino acid sequence of p52/53 analogue 5.
SEQ ID NO: 73 shows the amino acid sequence of p45/46 analogue 1.
SEQ ID NO: 74 shows the amino acid sequence of p45/46 analogue 2.
SEQ ID NO: 75 shows the nucleic acid sequence encoding p1.
SEQ ID NO: 76 shows the nucleic acid sequence encoding p2.
SEQ ID NO: 77 shows the nucleic acid sequence encoding p30.
SEQ ID NO: 78 shows the nucleic acid sequence encoding p39.
SEQ ID NO: 79 shows the nucleic acid sequence encoding p40.

SEQ ID NO: 80 shows the nucleic acid sequence encoding p50.

SEQ ID NO: 81 shows the nucleic acid sequence encoding p51.

SEQ ID NO: 82 shows the nucleic acid sequence encoding p52.

SEQ ID NO: 83 shows the nucleic acid sequence encoding p53.

SEQ ID NO: 84 shows the nucleic acid sequence encoding p45.

SEQ ID NO: 85 shows the nucleic acid sequence encoding p46.

SEQ ID NO: 86 shows the nucleic acid sequence encoding p50/51 SEQ ID NO: 87 shows the nucleic acid sequence encoding p52/53 SEQ ID NO: 88 shows the nucleic acid sequence encoding p45/46

SEQ ID NO: 89 shows the nucleic acid sequence encoding p20 SEQ ID NO: 90 shows the nucleic acid sequence encoding p21.

SEQ ID NO: 91 shows the nucleic acid sequence encoding p39 analogue 1.

SEQ ID NO: 92 shows the nucleic acid sequence encoding p50/51 analogue 1.

SEQ ID NO: 93 shows the nucleic acid sequence encoding p52/53 analogue 1.

SEQ ID NO: 94 shows the nucleic acid sequence encoding p40 analogue.

SEQ ID NO: 95 shows the nucleic acid sequence encoding p45/46 analogue 1.

SEQ ID NO: 96 shows the nucleic acid sequence encoding p45/46 analogue 2.

DETAILED DESCRIPTION OF THE INVENTION

Polypeptides

The invention provides a polypeptide consisting of less than 30 contiguous amino acids from the α3 domain and/or transmembrane domain of a major histocompatibility complex (MHC) class I human leukocyte antigen (HLA), or a derivative or analogue thereof. The invention also concerns the use of polypeptides derived from a MHC class I HLA, or a derivative or analogue thereof, as a medicament.

By the term "a MHC class I HLA" used herein, we refer to any gene product (for example, a protein as identified as SEQ ID NO: 1), defined as a MHC class I HLA in the 14$^{th}$ International HLA & Immunogenetics Workshop, 2005. The gene product may comprise at least 50% identity with a gene product encoded by a human MHC class I HLA allele (for example, as identified as SEQ ID NO: 3) and/or human HLA homologues from other species, or a variant or functional fragment thereof. More preferably, the MHC class I HLA gene product has at least 60%, preferably 70%, preferably 80%, preferably 90%, preferably 95%, and most preferably 99% identity with products encoded by human MHC class I HLA alleles and/or human MHC class I HLA homologues from other species, or a variant or functional fragment thereof. The HLA may be HLA-A, HLA-B or HLA-C.

The inventor based his investigations on the most common MHC I class I antigen, HLA-A2. Sequences for MHC class I antigen, HLA-A2, are known in the art, and may be found in publicly available databases, such as NCBI, e.g. at the NCBI website.

For example, the full-length protein sequence of human MHC class I antigen, HLA-A2, (i.e. the HLA*020101 allele) is identified as SEQ ID NO: 1. The mature protein sequence of human MHC class I antigen, HLA-A2, (i.e. the HLA*020101 allele) is identified as SEQ ID NO: 2. Furthermore, the nucleic acid sequence encoding human MHC class I antigen, HLA-A2, (i.e. the HLA*020101 allele) may be identified as SEQ ID NO: 3.

The nucleic acid sequence identified by SEQ ID NO: 3 comprises 8 exons, and 7 introns. These may be defined as follows:—exon 1: 200 bp-272 bp; intron 1: 273 bp-402 bp; exon 2: 403 bp-672 bp; intron 2: 673 bp-913 bp; exon 3: 914 bp-1189 bp; intron 3: 1190 bp-1789 bp; exon 4: 1790 bp-2065 bp; intron 4: 2066 bp-2164 bp; exon 5: 2165 bp-2281 bp; intron 5: 2282 bp-2719 bp; exon 6: 2720 bp-2752 bp; intron 6: 2753 bp-2894 bp; exon 7: 2895 bp-2942 bp; intron 7: 2943 bp-3111 bp; and exon 8: 3112 bp-3116 bp.

In preferred embodiments, the HLA is HLA-A2. By the term "HLA-A2" used herein, we refer to any gene product (for example, a protein as identified as SEQ ID NO: 1 or 2), defined as HLA-A2 in the 14$^{th}$ International HLA & Immunogenetics Workshop, 2005. The gene product may comprise at least 50% identity with a gene product encoded by a human HLA-A2 allele (for example, as identified as SEQ ID NO: 3) and/or human HLA-A2 homologues from other species, or a variant or functional fragment thereof. More preferably, the HLA-A2 gene product has at least 60%, preferably 70%, preferably 80%, preferably 90%, preferably 95%, and most preferably 99% identity with products encoded by human HLA-A2 alleles and/or human HLA-A2 homologues from other species, or a variant or functional fragment thereof.

In preferred embodiments, the HLA has the amino acid sequence shown in SEQ ID NO: 1 or SEQ ID NO: 2.

By the term "derived from a MHC class I HLA", we mean a polypeptide, derivative or analogue, which comprises an amino acid sequence forming a MHC class I antigen, HLA, and which is a derivative, analogue or modification thereof. In preferred embodiments, a polypeptide derived from a MHC class I HLA is a fragment or truncation of a MHC class I HLA. Surprisingly, peptides or polypeptides, or derivatives or analogues derived from HLA have been shown to exhibit therapeutic activity, and in particular, have been shown to be useful for preventing or minimising allograft failure or rejection.

By the term "derived from HLA-A2", we mean a polypeptide, derivative or analogue, which comprises an amino acid sequence forming the MHC class I antigen, HLA-A2, and which is a derivative, analogue or modification thereof. In preferred embodiments, a polypeptide derived from HLA-A2 is a fragment or a truncation of HLA-A2. Surprisingly, peptides or polypeptides, or derivatives or analogues derived from HLA-A2 have been shown to exhibit therapeutic activity, and in particular, have been shown to be useful for preventing or minimising allograft failure or rejection. All of SEQ ID NOs: 1, 2 and 4 to 73 are polypeptides that have been derived from HLA-A2.

By the term "derivative or analogue thereof", we mean that the amino acid residues of the polypeptide derived from the MHC class I HLA protein may be replaced by residues (whether natural amino acids, non-natural amino acids or amino acid mimics) with similar side chains or peptide backbone properties. Additionally, the terminals of such peptides may be protected by N- or C-terminal protecting groups with similar properties to acetyl or amide groups.

Similarly, by the term "derivative or analogue thereof", we mean that the amino acid residues of the polypeptide derived from the HLA-A2 protein may be replaced by residues (whether natural amino acids, non-natural amino acids or amino acid mimics) with similar side chains or peptide backbone properties. Additionally, the terminals of such peptides may be protected by N- or C-terminal protecting groups with similar properties to acetyl or amide groups.

Derivatives and analogues can be formed by making one or more mutations to the polypeptide sequence derived from a MHC class I HLA protein (or HLA-A2). The mutations can be substitutions, deletions or insertions of amino acids. A derivative or an analogue may differ from the polypeptide by at least 1, but less than 5, 10, 20, 50, 100, 150, 200 or 250 amino acids from the sequences shown in SEQ ID NO: 1 or 2. Examples of derivatives and analogues include all of the truncations, analogues, variants, fragments and alloantigens discussed in more detail below.

A derivative or an analogue of a polypeptide, such as a derivative or analogue of a polypeptide derived from a MHC class I antigen or derived from HLA-A2, binds to a MHC class II HLA and activates a T cell specific for the polypeptide. In other words, a derivative or an analogue of a polypeptide will bind to a MHC class II HLA and activate a T cell bearing a T cell receptor that is specific for the polypeptide. For instance, a derivative or an analogue of a polypeptide derived from HLA-A2 will bind to a MHC class II HLA and activate a T cell bearing a receptor that is specific for the polypeptide derived from HLA-A2. A T cell is specific for a polypeptide or bears a T cell receptor that is specific for the polypeptide if it is selected or cloned by exposure to the polypeptide. Methods for selection or cloning of T cells are well known in the art. For instance, a suitable method is described in Lamb et al., J. Exp. Biol., 1983; 157: 1434-1447.

A MHC class I HLA comprises five domains, namely α1 domain, an α2 domain, an α3 domain, a transmembrane domain and a cytosolic domain.

Figure 1:
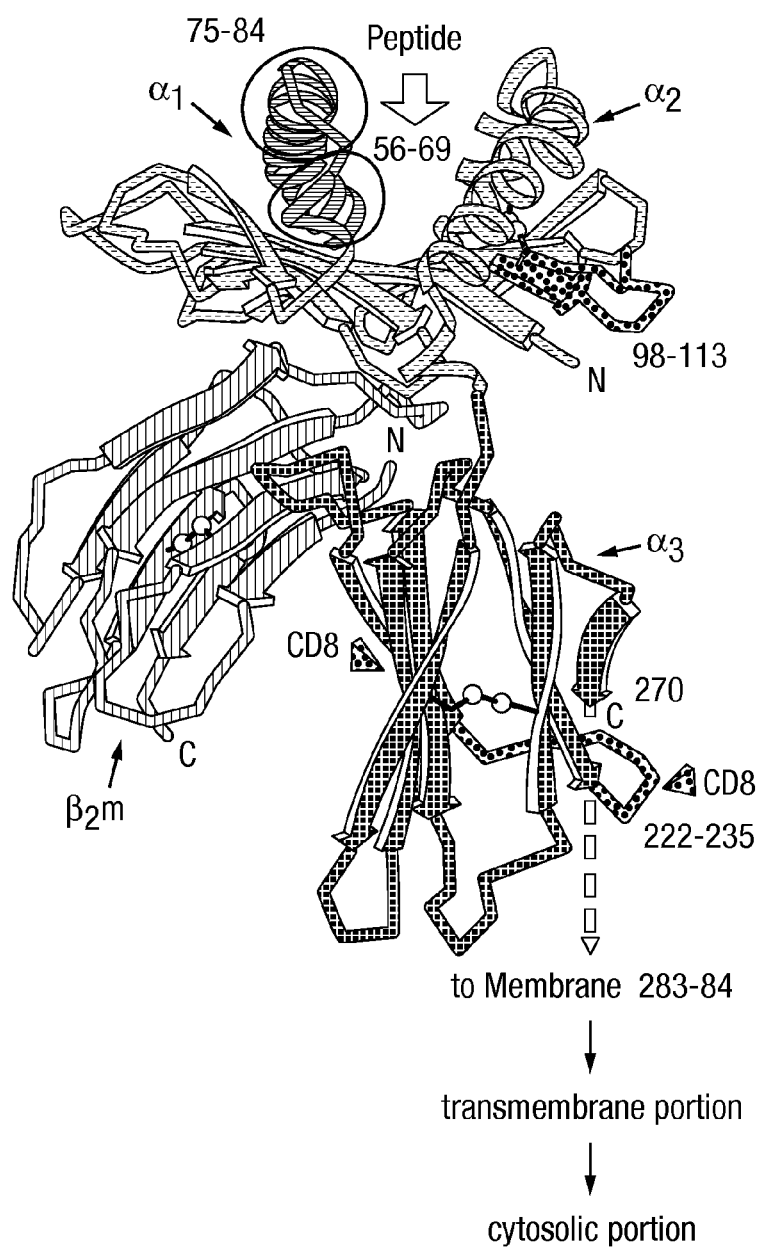
FIG. 1 shows a 3D structure representation of the extracellular portion of the human MHC class I, HLA-A2, showing α1, α2, α3, and transmembrane domains, and a β2 microglobulin bound thereto.

It will be appreciated from SEQ ID NO: 1 that full-length human class I histocompatability molecule, HLA-A2 protein, consists of 365 amino acid residues. It will be appreciated from SEQ ID NO: 2 that mature human class I histocompatability molecule, HLA-A2 protein, consists of 341 amino acid residues. FIG. 1 shows a schematic representation of the extracellular portion of HLA-A2. It can be seen that HLA-A2 comprises an α1 domain, an α2 domain, an α3 domain, and also a transmembrane domain and a cytosolic domain, the latter two domains not being shown in the Figure. It will be appreciated that the α1 and α2 domains define a substantially polymorphic region of the HLA-A2 molecule, and that the α3 domain and the transmembrane domain define a substantially non-polymorphic region of the HLA-A2 molecule. Furthermore, a molecule of beta-2-microglobulin ($\beta_2$m) binds to the junction of the α1 and α2 domains, and to the α3 domain by non-covalent interactions. Not shown in FIG. 1 is the presence of a short peptide bound non-covalently in the groove between the alpha helices of α1 and α2 domains. It will be appreciated that the combination of the peptide and adjacent portions of alpha helices makes up the epitope seen by CD8+ T cells. This discussion concerning the structure and function of the five domains in HLA-A2 also applies to other MHC class I HLAs, such as HLA-B or HLA-C.

In some embodiments, the invention may use polypeptides, derivatives or analogues thereof which are derived substantially from the whole MHC class I HLA. In some embodiments, the invention may use polypeptides, derivatives or analogues thereof, which are derived from substantially the whole HLA-A2 protein molecule, substantially as set out defined by SEQ ID NO: 1 or 2. Hence, the MHC class I HLA or the HLA-A2 molecule used in the invention may comprise the α1 domain, the α2 domain, the α3 domain, the transmembrane domain, and the cytosolic domain. The entire HLA-A2 molecule comprises 365 amino acids (SEQ ID NO: 1).

However, the inventor has demonstrated that polypeptides, or derivatives or analogues derived from the HLA-A2 protein molecule (i.e. less than 365 amino acids) may also be used in accordance with the invention. Hence, the polypeptide, derivative or analogue thereof used in accordance with the invention may comprise a truncation of the entire MHC class I HLA. Preferably, the polypeptide, derivative or analogue thereof used in accordance with the invention comprises a truncation of the entire HLA-A2 protein. The discussion below concerning truncations focuses on truncations of HLA-A2. However, such discussion also applies to other MHC class I HLAs, such as HLA-B or HLA-C By the term "truncation", we mean a polypeptide which corresponds to a region or fragment of the HLA-A2 protein, but which is reduced in size by removal of amino acids. The reduction of amino acids may be by removal of residues from the C- or N-terminal of the peptide, or may be by deletion of one of more amino acids from within the core of the HLA-A2 molecule (i.e. amino acids 2-364 of SEQ ID NO: 1). For example, the peptide may comprise a deletion of 5, 10, 15, 20, or 25 amino acid residues from the whole HLA-A2 molecule. More preferably, the peptide may comprise a deletion of 50, 75, 100, 125, 150, 200, 225, or 150 amino acid residues from the whole HLA-A2 molecule.

Suitably, the polypeptide or derivative or analogue thereof derived from HLA-A2 comprises less than about 100 amino acids, more suitably, less than about 75 amino acids, and even more suitably, less than 50 amino acids. It is preferred that the polypeptide, derivative or analogue thereof derived from HLA-A2 comprises less than 30 amino acids, and more preferably, less than 20 amino acids, and most preferably, about 15 amino acids. The inventor believes that reducing the size of HLA-A2 that still shows a therapeutic effect would help therapeutic delivery to a subject being treated.

Since T lymphocytes recognise proteins on the basis of their primary sequence as short peptides bound to MHC molecules, the inventor believes that peptides, derivatives or analogues according to the invention may be used to specifically desensitise T cell responses, without the risk of exposure to 'whole' antigen. This is particularly advantageous because the whole antigen or at least large parts of the antigen with secondary and/or tertiary structure may itself cause sensitisation. Furthermore, another clinical benefit observed in such so-called peptide therapy is that peptides, derivatives or analogues thereof which are derived from a MHC class I HLA, such as HLA-A2, may induce regulatory T cells that can exert an antigen specific, dominant negative effect on the immune system. Another significant advantage of the use of peptides is that they can be easily delivered without the induction of a danger signal, which would promote productive immunity in the subject being treated.

Hence, the polypeptide or derivative or analogue thereof derived from MHC class I HLA protein may be derived from a domain independently selected from a group of domains consisting of the α1 domain; the α2 domain; the α3 domain; the transmembrane domain; the cytosolic domain; or any combination thereof. For example, the polypeptide or analogue may be derived from the α1 domain and/or the α2 domain of HLA-A2. Preferably, the polypeptide or analogue may be derived from the α3 domain and/or the transmembrane domain of a MHC class I HLA.

The invention specifically provides a polypeptide consisting of less than 30 contiguous amino acids from the α3 domain and/or transmembrane domain of a MHC class I HLA, or a derivative or analogue thereof. In preferred embodiments, the polypeptide consists of less than 20 contiguous amino acids or about 15 contiguous amino acids from the α3 domain and/or transmembrane domain of a MHC class I HLA. In another preferred embodiment, the derivative or analogue has a sequence identity of greater than 65% sequence identity to at least 9 contiguous amino acids in the polypeptide. Specific sequences provided by the invention (SEQ ID NOs: 42, 43, 48, 49 and 53 to 74) are discussed in more detail below.

Similarly, a polypeptide or derivative or analogue thereof derived from HLA-A2 protein may be derived from a domain independently selected from a group of HLA-A2 domains consisting of the α1 domain; the α2 domain; the α3 domain; the transmembrane domain; the cytosolic domain; or any combination thereof. For example, the peptide or analogue may be derived from the α1 domain and/or the α2 domain of HLA-A2. Alternatively, the peptide or analogue may be derived from the α3 domain and/or the transmembrane domain of HLA-A2.

In HLA-A2, the α1 domain is encoded by exon 2, i.e. nucleotides 403-672 of SEQ ID NO: 3. Hence, the polypeptide, derivative or analogue may comprise substantially the amino acid sequence defined as residues 1-90 of SEQ ID NO: 2, and may be encoded by nucleotides 403-672 of SEQ ID NO: 3. The α2 domain is encoded by exon 3, i.e. nucleotides 914-1189 of SEQ ID NO: 3. Hence, the polypeptide, derivative or analogue may comprise substantially the amino acid sequence defined as residues 91-182 of SEQ ID NO: 2, and may be encoded by nucleotides 914-1189 of SEQ ID NO: 3. The α3 domain is encoded by exon 4, i.e. nucleotides 1790-2065 of SEQ ID NO: 3. Hence, the polypeptide, derivative or analogue may comprise substantially the amino acid sequence defined as residues 183-274 of SEQ ID NO: 2, and may be encoded by nucleotides 1790-2065 of SEQ ID NO: 3. The transmembrane domain is encoded by exon 5, i.e. nucleotides 2165-2281 of SEQ ID NO: 3. Hence, the polypeptide, derivative or analogue may comprise substantially the amino acid sequence defined as residues 275-314 of SEQ ID NO: 2, and may be encoded by nucleotides 2165-2281 of SEQ ID NO: 3.

Surprisingly, the results of the binding studies discussed the Examples 1 and 2 revealed a significant number of polypeptides that bind relatively 'promiscuously' to MHC class II. Some of the peptides are derived from the hypervariable or polymorphic region of HLA-A2 (i.e. the α1 & α2 domains). For example, peptide p20 (SEQ ID NO: 23) is derived from amino acid residues 105-119 of HLA-A2 (SEQ ID NO: 2), and peptide p21 (SEQ ID NO: 24) is derived from residues 107-121). Both peptides correspond to a 17 amino acid peptide that has been eluted from DR1. The inventor observed a positive response in 10 out of 15 patients who had made anti-HLA-A2. Hence, a single 17 amino acid peptide that binds promiscuously to MHC class II molecules accounts for much of the immunogenicity in this region whatever the MHC class II.

Accordingly, the inventor believes that a single (or two closely overlapping peptides) may be used in a treatment regime. Hence, the polypeptide, derivative or analogue used according to the invention may be derived from a substantially polymorphic region of the MHC class I HLA molecule, and more preferably, from the α1 and/or α2 domain thereof. Similarly, the polypeptide, derivative or analogue used according to the invention may be derived from a substantially polymorphic region of the HLA-A2 molecule, and more preferably, from the α1 and/or α2 domain thereof.

Hence, preferred polypeptides used according to the invention comprise substantially the amino acid sequence:

(a) HSMRYFFTSVSRPGR (SEQ ID NO: 4). This peptide corresponds to amino acids 3-17 of HLA-A2 protein (i.e. SEQ ID NO: 2), and is derived from the α1 domain of the HLA-A2 molecule. This peptide is designated p1 when referred to herein, and has a molecular weight of 1827.1.

(b) MRYFFTSVSRPGRGE (SEQ ID NO: 5). This peptide corresponds to amino acids 5-19 of HLA-A2 protein (i.e. SEQ ID NO: 2), and is derived from the α1 domain of the HLA-A2 molecule. This peptide is designated p2 when referred to herein, and has a molecular weight of 1789.

(c) HKWEAAHVAEQLRAY (SEQ ID NO: 33). This peptide corresponds to amino acids 145-159 of HLA-A2 protein (i.e. SEQ ID NO: 2), and is derived from the α2 domain of the HLA-A2 molecule. This peptide is designated p30 when referred to herein, and has a molecular weight of 1808.

(d) SDWRFLRGYHQYAYD (SEQ ID NO: 23). This peptide corresponds to amino acids 105-119 of HLA-A2 protein (i.e. SEQ ID NO: 2), and is derived from the α2 domain of the HLA-A2 molecule. This peptide is designated p20 when referred to herein, and has a molecular weight of 1976.1.

(e) WRFLRGYHQYAYDGK (SEQ ID NO: 24). This peptide corresponds to amino acids 107-121 of HLA-A2 protein (i.e. SEQ ID NO: 2), and is derived from the α2 domain of the HLA-A2 molecule. This peptide is designated p21 when referred to herein, and has a molecular weight of 1959.2.

It should be appreciated that each of the peptides (a) to (e) are derived from the polymorphic region of HLA-A2. However, the inventor was surprised to find that a significant number of individuals also respond to peptides derived from elsewhere in the HLA-A2 molecule, and in particular, regions of HLA-A2 that are of limited polymorphism, for example, the α3 and transmembrane domains. The inventor believes that to date there have been no reports of immune responses to peptides from at least limited or substantially non-polymorphic regions of HLA-A2, and in particular, the α3 and transmembrane domains of HLA-A2, or any other HLA molecule, and consequently no report or proposal for their use in peptide-based therapies. The inventor also believes that using peptides derived from the non-polymorphic regions of HLA-A2 may have a wider applicability than those derived from the polymorphic and therefore unique regions of HLA-A2. Because they are of limited polymorphism, these peptides act as sites of potential cross-reactivity between different HLA molecules.

Accordingly, preferred polypeptides, derivatives or analogues thereof of the invention are derived from a substantially limited or non-polymorphic region of the MHC class I HLA molecule, such as the α3 and/or transmembrane domain. It is especially preferred that polypeptides, derivatives or analogues thereof used according to the invention are derived from a substantially limited or non-polymorphic region of the HLA-A2 molecule. Preferably, the polypeptide, derivative or analogue thereof is derived from the α3 and/or transmembrane domain of HLA-A2.

Therefore, most preferred peptides used according to the invention comprise substantially the amino acid sequence:

(f) HAVSDHEATLRCWAL (SEQ ID NO: 42 ). This peptide corresponds to amino acids 192-206 of HLA-A2 protein (i.e. SEQ ID NO: 2 ), and is derived from the a3 domain of the HLA-A2 molecule. This peptide is designated p39 when referred to herein, and has a molecular weight of 1708.

(g) RCWALSFYPAEITLT (SEQ ID NO: 43 ). This peptide corresponds to amino acids 202-216 of HLA-A2 protein (i.e. SEQ ID NO: 2 ), and is derived from the a3 domain of the HLA-A2 molecule. This peptide is designated p40 when referred to herein, and has a molecular weight of 1770.

(h) KPLTLRWEPSSQPTI (SEQ ID NO: 53 ). This peptide corresponds to amino acids 268-282 of HLA-A2 protein (i.e. SEQ ID NO: 2 ), and is derived from the a3 domain and the transmembrane domain of the HLA-A2 molecule. This peptide is designated p50 when referred to herein, and has a molecular weight of 1752.

(i) LTLRWEPSSQPTIPI (SEQ ID NO: 54). This peptide corresponds to amino acids 270-284 of HLA-A2 protein (i.e. SEQ ID NO: 2), and is derived from the α3 domain and the transmembrane domain of the HLA-A2 molecule. This peptide is designated p51 when referred to herein, and has a molecular weight of 1737.

(j) PTIPIVGIIAGLVLF (SEQ ID NO: 55). This peptide corresponds to amino acids 280-294 of HLA-A2 protein (i.e. SEQ ID NO: 2), and is derived from the transmembrane domain of the HLA-A2 molecule. This peptide is designated p52 when referred to herein, and has a molecular weight of 1522.

(k) IPIVGIIAGLVLFGA (SEQ ID NO: 56). This peptide corresponds to amino acids 282-296 of HLA-A2 protein (i.e. SEQ ID NO: 2), and is derived from the transmembrane domain of the HLA-A2 molecule. This peptide is designated p53 when referred to herein, and has a molecular weight of 1452.

(l) GTFQKWAAVVVPSGQEQR GTFOKWAAVVVPSGO (SEQ ID NO: 48). This peptide corresponds to amino acids 239-253 of HLA-A2 protein (i.e. SEQ ID NO: 2), and is derived from the α3 domain of the HLA-A2 molecule. This peptide is designated p45 when referred to herein, and has a molecular weight of 1574.

(m) FQKWAAVVVPSGQEQR (SEQ ID NO: 49). This peptide corresponds to amino acids 241-256 of HLA-A2 protein (i.e. SEQ ID NO: 2), and is derived from the α3 domain of the HLA-A2 molecule. This peptide is designated p46 when referred to herein, and has a molecular weight of 1829.

It should be appreciated that each of the peptides (f) to (m) are derived from the substantially non-polymorphic region of HLA-A2. The inventor has found that peptides that are derived from the non-polymorphic region (i.e. α3 and transmembrane domains) of HLA-A2 show a surprisingly high frequency of response in patients that have made antibody to HLA-A2 and significant responses in some others. The inventor believes that these have not been previously defined as T cell epitopes, and are important because they are of limited polymorphism.

The inventor has also found that use of polypeptides, derivatives or analogues, which comprise overlapping regions of any of the preferred peptides disclosed herein have a therapeutic effect, and show surprising efficacy for treating conditions characterised by allosensitisation, such as, allograft failure of rejection. It is therefore preferred that polypeptides, derivatives or analogues thereof derived from the non-polymorphic regions of a MHC class I HLA, such as HLA-A2, comprise overlapping sections or regions.

Hence, further preferred polypeptides used according to the invention comprise substantially the amino acid sequence:

(n) KPLTLRWEPSSQPTIPI (SEQ ID NO: 57). This peptide corresponds to overlapping amino acids 268-282 and 270-284 of HLA-A2 protein (i.e. SEQ ID NO: 2). This peptide is designated p50/51 when referred to herein.

(o) PTIPIVGIIAGLVLFGA (SEQ ID NO: 58). This peptide corresponds to overlapping amino acids 280-294 and 282-296 of HLA-A2 protein (i.e. SEQ ID NO: 2). This peptide is designated p52/53 when referred to herein.

(p) GTFQKWAAVVVPSGQEQR (SEQ ID NO: 59). This peptide corresponds to overlapping amino acids 239-253 & 241-256 of HLA-A2 protein (i.e. SEQ ID NO: 2). This peptide is designated p45/46 when referred to herein.

By analogy with anti-HLA antibodies, the inventor believes that the preferred peptides derived from the α3 and transmembrane domains could be referred to as 'public' T cell epitopes. This is relevant to the evolution of spreading immune responses to different HLA, and in designing peptides or mixtures thereof having therapeutic potential.

By way of example, as shown in FIGS. 5 and 13, the sequence of peptide p39, i.e. SEQ ID NO: 42, which is derived from amino acids 192-206 of HLA-A2, is also present in the sequence of the following HLA molecules: HLA-A2, HLA-A25, HLA-A26, HLA-A29, HLA-A31, HLA-A32, HLA-A33, HLA-A34, HLA-A43, HLA-A66, HLA-A68, HLA-A69, and HLA-A74. Therefore, upon administration of peptide p39 or a derivative or an analogue thereof to a patient, the inventor believes that it is capable of modulating the immune response to a transplant bearing any of these HLA molecules, and is not limited to HLA-A2 only. It will be appreciated that this is a significant advantage of using such a peptide, derivative or analogue in therapy, because of its multiple effects, thereby preventing rejection or failure of an allograft harbouring a wide range of HLA antigens.

Furthermore, similarly, there is only a single variant of the sequence of p39 (SEQ ID NO: 42) expressed by all other HLA-A molecules, HLA-A1, HLA-A3, HLA-A11, HLA-A23, HLA-A24, HLA-A30, HLA-A36, HLA-A80, and most HLA-B molecules, as indicated in FIGS. 5 and 13. This variant is called p39 analogue 1 and is shown in SEQ ID NO: 60. Accordingly, upon administration of peptide p39 and an analogue thereof having the sequence of SEQ ID NO: 60 (in which proline replaces alanine at residue 193 and isoleucine replaces valine at residue 194), the inventor believes that such a combination has the potential to modulate the immune response to a transplant bearing all HLA-A molecules and most HLA-B molecules also.

Furthermore, similarly, there is a single variant of the sequence of p39 (SEQ ID NO: 42) expressed by other HLA-B molecules, HLA-B51, HLA-B52, HLA-B53, HLA-B58, HLA-B78 as indicated in FIG. 13. This variant is called p39 analogue 2 and is shown in SEQ ID NO: 61. Accordingly, upon administration of peptide p39 and an analogue thereof having the sequence of SEQ ID NO: 61 (in which proline replaces alanine at residue 193), the inventor believes that such a combination has the potential to modulate the immune response to a transplant bearing a wide range of HLA-A molecules and some HLA-B molecules also.

Furthermore, similarly, there is a single variant of the sequence of p39 (SEQ ID NO: 42) expressed by HLA-B44 as indicated in FIG. 13. This variant is called p39 analogue 3 and is shown in SEQ ID NO: 62. Accordingly, upon administration of peptide p39 and an analogue thereof having the sequence of SEQ ID NO: 62 (in which proline replaces alanine at residue 193 and valine replaces alanine at residue 199), the inventor believes that such a combination has the potential to modulate the immune response to a transplant bearing a wide range of HLA-A molecules as well as HLA-B44.

By way of a further example, as shown in FIG. 13, the sequence of peptide p40, i.e. SEQ ID NO: 43, which is derived from amino acids 202-216 of HLA-A2, is also present in the sequence of the following HLA molecules: HLA-A2, HLA-A25, HLA-A26, HLA-A29, HLA-A31, HLA-A32, HLA-A33, HLA-A34, HLA-A43, HLA-A66, HLA-A68, HLA-A69, HLA-A74, and HLA-A74. Therefore, upon administration of peptide p40 or a derivative or an analogue thereof to a patient, the inventor believes that it is capable of modulating the immune response to a transplant bearing any of these HLA molecules, and is not limited to HLA-A2 only.

It will be appreciated that this is a significant advantage of using such a peptide, derivative or analogue in therapy, because of its multiple effects, thereby preventing rejection or failure of an allograft harbouring a wide range of HLA antigens.

Furthermore, similarly, there is a single variant of the sequence of p40 (SEQ ID NO: 43) expressed by other HLA-A molecules, HLA-A1, HLA-A3, HLA-A11, HLA-A23, HLA-A24, HLA-A30, HLA-A36, as well as most HLA-B molecules, as indicated in FIG. 14. This variant is called p40 analogue and is shown in SEQ ID NO: 63. Accordingly, upon administration of peptide p40 and an analogue thereof having the sequence of SEQ ID NO: 63 (in which glycine replaces serine at residue 207), the inventor believes that such a combination has the potential to modulate the immune response to a transplant bearing a wide range of HLA-A molecules and HLA-B molecules also.

Figure 6:
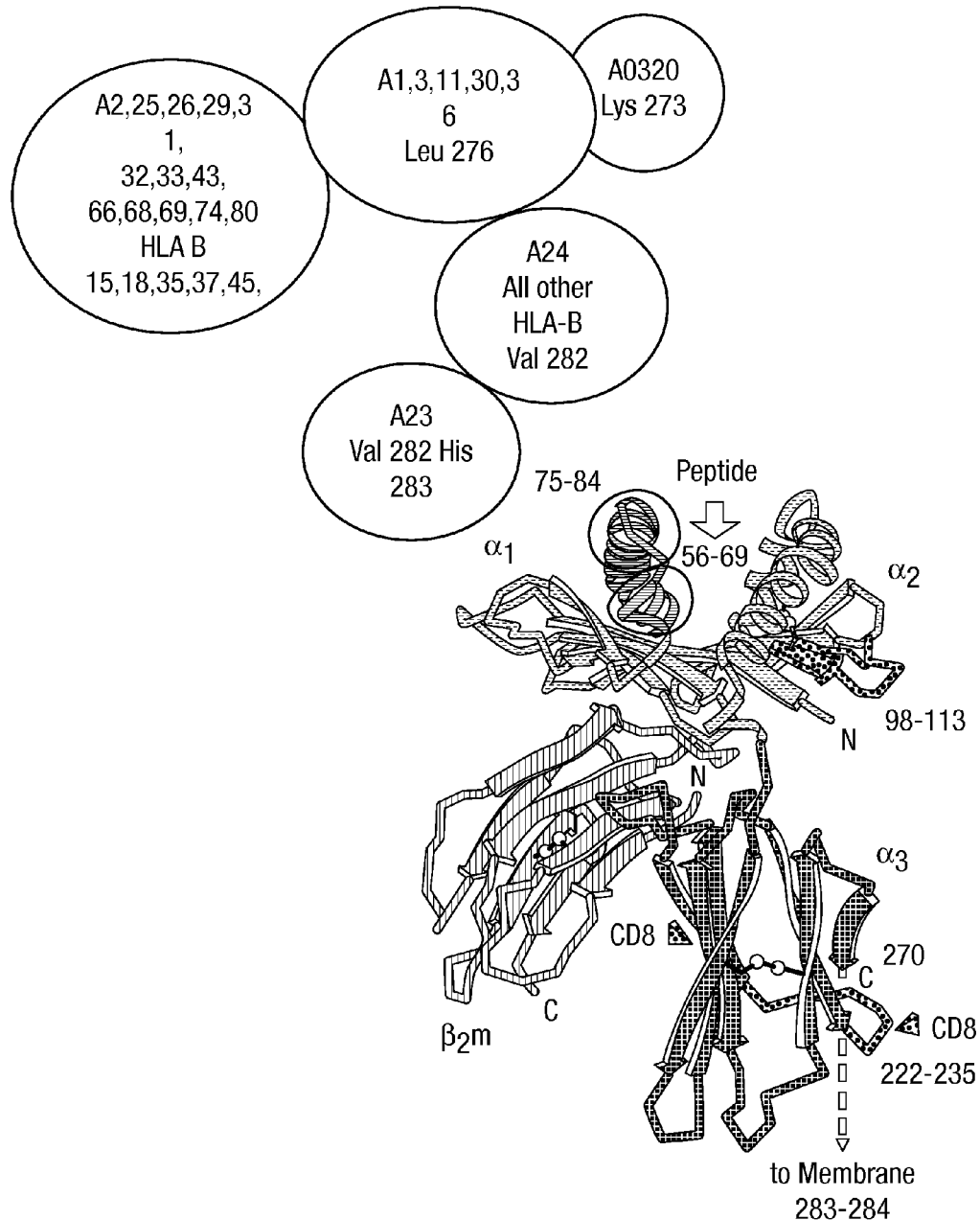
FIG. 6 shows a schematic representation of the extracellular portion of the human class MHC class I, HLA-A2, and peptides p50 (residues 268-282 of HLA-A2) (SEQ ID NO: 53) and p51 (residues 270-284 of HLA-A2) (SEQ ID NO: 54).
Figure 7:
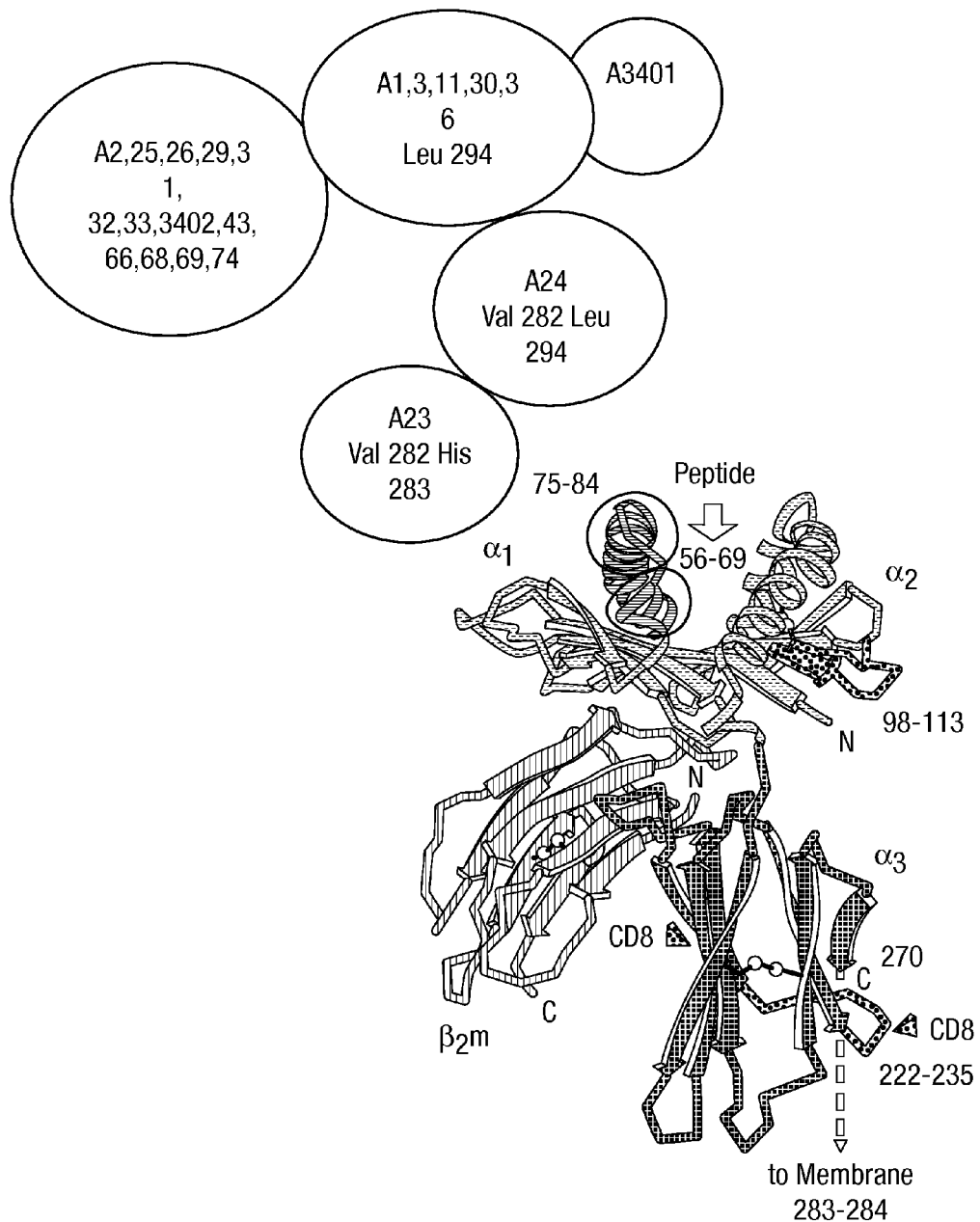
FIG. 7 shows a schematic representation of the extracellular portion of the human class MHC class I, HLA-A2, and peptides p52 (residues 280-294 of HLA-A2) (SEQ ID NO: 55) and p53 (residues 282-296 of HLA-A2) (SEQ ID NO: 56).

Furthermore, as illustrated in FIGS. 6 and 15, peptide p50 (SEQ ID NO: 53), which is derived from amino acids 268-282, and peptide p51 (SEQ ID NO: 54), which is derived from amino acids 270-284, comprise sequences that are offset by only 2 amino acids and therefore span a 17 amino acid stretch. Similarly, as illustrated in FIGS. 7 and 16, peptide p52 (SEQ ID NO: 55), which is derived from amino acids 280-294, and peptide p53 (SEQ ID NO: 56), which is derived from amino acids 282-296, comprise sequences that are offset by only 2 amino acids and therefore span a 17 amino acid stretch. In both cases, the identified peptides are not only present in HLA-A2, but also in HLA-A25, HLA-A26, HLA-A29, HLA-A31, HLA-A32, HLA-A33, HLA-A43, HLA-A66, HLA-A68, HLA-A69, HLA-A74, and HLA-A80.

p51 (SEQ ID NO: 54) and p52 (SEQ ID NO: 55) are also present in HLA-B15, HLA-B18, HLA-B35, HLA-B37, HLA-B45, HLA-B48, HLA-B49, HLA-B50, HLA-B51, HLA-B52, HLA-B53, HLA-B54, HLA-B55, HLA-B58, HLA-B59, HLA-B73, HLA-B78, HLA-B82 and HLA-B95 (FIG. 14).

Additionally, analogues of these two sequences in which a leucine is substituted for a proline at residue 276 (for the 17mer 268-284; SEQ ID NO: 64) or a leucine is substituted for a phenylanine at 294 (for the 17mer 280-296; SEQ ID NO: 65), would provide peptide sequences that would be expressed by the majority of HLA-A molecules in a way analogous to that described for p39, the only substantial omissions being HLA-A23 & HLA-A24.

Other analogues of p50/51 and p52/53 are described in the Table 1 below.

TABLE 1

Additional analogues of p50/51 and p52/53

| SEQ ID NO: | Analogue | Change(s) to arrive at the analogue | Present in HLA |
|---|---|---|---|
| 66 | p50/51 analogue 2 | Lysine at 273 | A0320 |
| 67 | p50/51 analogue 3 | Valine at 282 | A24 All HLA-B in which p50 is not present |
| 68 | p50/51 analogue 4 | Valine at 282 Histidine at 283 | A23 |
| 69 | p52/53 analogue 2 | Valine at 282 Leucine at 294 | A24 |
| 70 | p52/53 analogue 3 | Valine at 282 Histidine at 283 | A23 |
| 71 | p52/53 analogue 4 | Alanine at 292 Valine at 293 Leucine at 294 Alanine at 295 Valine at 296 | HLA-B 15, 18, 35, 37, 45, 48-55, 58, 59, 73, 78, 82, 95 |

TABLE 1-continued

Additional analogues of p50/51 and p52/53

| SEQ ID NO: | Analogue | Change(s) to arrive at the analogue | Present in HLA |
|---|---|---|---|
| 72 | p52/53 analogue 5 | Valine at 282 Alanine at 292 Valine at 293 Leucine at 294 Alanine at 295 Valine at 296 | All other HLA-B |

Therefore, upon administration of a combination of polypeptides p50, p51, 52, and p53, or derivatives or analogues thereof to a patient, the inventor believes that it is capable of modulating the immune response to a transplant bearing any of these HLA molecules.

As will be apparent, specific combinations of p39, p40, p50, p51, p50/51, p52, p53 and/or p52/53 and one or more of their analogues discussed above have the potential to modulate the immune response to a transplant bearing all HLA-A molecules as well as all HLA-B molecules. This has the advantage of using as few polypeptides as possible to modulate the immune response to a transplant bearing any HLA-A or HLA-B molecule.

Hence, it will be appreciated from the foregoing that preferred polypeptides, derivatives or analogues thereof which are derived from the non-polymorphic region of HLA-A2 are also expressed by many other HLA-A molecules, and not just HLA-A2, by acting as sites of potential cross-reactivity between different HLA molecules. Hence, surprisingly, the inventor believes that the benefits of using such peptides in methods according to the invention, and in particular for uses in treating or preventing conditions characterised by allosensitisation, and particularly, allograft rejection, and alloantibody synthesis, may be much wider than to HLA-A2 antigen alone. Accordingly, the inventor believes that the implications of their findings are much broader than solely help for antibody production, but relate to immune mechanisms of graft rejection per se, and are wider than target HLA-A2, extending to responses to transplantation antigens in general.

Polypeptides use in accordance with the invention can be an alloantigen, or a polypeptide derived therefrom, or a derivative or analogue thereof. Preferably, the alloantigen, or polypeptide derived therefrom, or derivative or analogue thereof may be independently selected from a group consisting of HLA-A2, HLA-A25, HLA-A26, HLA-A29, HLA-A31, HLA-A33, HLA-A34, HLA-A43, HLA-A66, HLA-A68, HLA-A69, HLA-A74, HLA-A1, HLA-A3, HLA-A11, HLA-A24, HLA-A30, HLA-A36, HLA-A80, HLA-A1, HLA-A3, HLA-A11, and HLA-A23, or any combination thereof.

Preferred polypeptides derived from the alloantigen may include p39 (SEQ ID NO: 42), p50/51 (SEQ ID NO: 57), p52/53 (SEQ ID NO: 58), p50 (SEQ ID NO: 53), p51 (SEQ ID NO: 54), 52 (SEQ ID NO: 55), and p53 (SEQ ID NO: 56), or derivatives or analogues thereof, or any combination thereof. It will be appreciated that these polypeptides are all derived from HLA-A2. Furthermore, efficacious derivatives or analogues of any of the polypeptides defined herein may also be used in accordance with the invention. For instance, corresponding polypeptides from other MCH class I antigens, such as HLA-B and HLA-C, can be used.

The inventor also believes that various analogues of any of the preferred polypeptides may also show efficacy at preventing or minimising allograft failure or rejection, as shown in the alignments below:

p39
HAVSDHEATLRCWAL (SEQ ID NO: 42)

(q) p39 analogue 1
HPISDHEATLRCWAL (SEQ ID NO: 60)

p50
KPLTLRWEPSSQPTI (SEQ ID NO: 53)

p51
LTLRWEPSSQPTIPI (SEQ ID NO: 54)

(r) analogue 1 17mer
KPLTLRWELSSQPTIPI (SEQ ID NO: 64)

p52
PTIPIVGIIAGLVLF (SEQ ID NO: 55)

p53
IPIVGIIAGLVLFGA (SEQ ID NO: 56)

(s) analogue 1 17mer
PTIPIVGIIAGLVLLGA (SEQ ID NO: 65)

p40
RCWALSFYPAEITLT (SEQ ID NO: 43)

(t) p40 analogue
RCWALGFYPAEITLT (SEQ ID NO: 63)

p45/46
GTFQKWAAVVVPSGQEQR (SEQ ID NO: 59)

(u) p45/46 analogue 1
GTFQKWAAVVVPSGEEQR (SEQ ID NO: 73)

(v) p45/46 analogue 2
GTFQKWASVVVPSGQEQR (SEQ ID NO: 74)

Hence, preferred analogues used according to the invention comprise substantially the amino acid sequence:

(q) HPISDHEATLRCWAL (SEQ ID NO: 60). This analogue is derived from peptide p39 (SEQ ID NO: 42), and is derived from the α3 domain of the HLA-A2 molecule, except that the alanine residue is replaced with a proline residue, and the valine residue is replaced with an isoleucine residue. This analogue is designated "p39 analogue 1" when referred to herein.

(r) KPLTLRWELSSQPTIPI (SEQ ID NO: 64). This analogue is derived from peptides p50 (SEQ ID NO: 53) and p51 (SEQ ID NO: 54), and is derived from the α3 domain and the transmembrane domain of the HLA-A2 molecule, except that the proline residue at position 276 is replaced with a leucine residue. This analogue is designated "p50/p51 analogue 1" when referred to herein.

(s) PTIPIVGIIAGLVLLGA (SEQ ID NO: 65). This analogue is derived from peptides p52 (SEQ ID NO: 55) and p53 (SEQ ID NO: 56), and is derived from the transmembrane domain of the HLA-A2 molecule, except that the phenylalanine residue at 294 is replaced with a leucine residue. This analogue is designated "p52/53 analogue 1" when referred to herein.

(t) RCWALGFYPAEITLT (SEQ ID NO: 63). This analogue is derived from peptide p40 (i.e. SEQ ID NO: 43), and is derived from the α3 domain of the HLA-A2 molecule, except that the serine residue at position 207 is replaced with a glycine residue. This analogue is designated "p40 analogue" when referred to herein.

(u) GTFQKWAAVVVPSGEEQR (SEQ ID NO: 73). This analogue is derived from peptide p45/46 (SEQ ID NO: 59), and is derived from the α3 domain of the HLA-A2 molecule, except that the glutamine residue is replaced with a glutamic acid residue. This analogue is designated "p45/p46 analogue 1" when referred to herein.

(v) GTFQKWASVVVPSGQEQR (SEQ ID NO: 74). This analogue is derived from peptide p45/46 (SEQ ID NO: 59), and is derived from the α3 domain of the HLA-A2 molecule, except that the alanine residue is replaced with a serine residue. This analogue is designated "p45/46 analogue 2" when referred to herein.

It will be appreciated that the invention extends to use of any polypeptide, derivative or analogue thereof derived from a MHC class I HLA, which comprises substantially the amino acid sequences of any of the sequences referred to herein, including functional variants, or fragments thereof. It also will be appreciated that the invention extends to use of any polypeptide, derivative or analogue thereof derived from HLA-A2, which comprises substantially the amino acid sequences of any of the sequences referred to herein, including functional variants, or fragments thereof. By the terms "substantially the amino acid/polynucleotide/polypeptide sequence", "functional variant" and "functional fragment", we mean that the sequence has at least 40% sequence identity with the amino acid/polynucleotide/polypeptide sequences of any one of the sequences referred to herein, for example, 40% identity with the hla-a2 gene identified as SEQ ID NO: 2, or 40% identity with the HLA-A2 protein identified as SEQ ID NO: 1 or 2. Amino acid/polynucleotide/polypeptide sequences with a sequence identity which is greater than 65%, more preferably, greater than 70%, even more preferably, greater than 75%, and still more preferably, greater than 80% sequence identity to any of the sequences referred to is also envisaged. Preferably, the amino acid/polynucleotide/polypeptide sequence has 85% identity with any of the sequences referred to, more preferably 90% identity, even more preferably 92% identity, even more preferably 95% identity, even more preferably 97% identity, even more preferably 98% identity and, most preferably, 99% identity with any of the referred to sequences.

The percentage identity between two amino acid/polynucleotide/polypeptide sequences can be measured over any length of the amino acid/polynucleotide/polypeptide sequences. For instance, the identity can be measured over the full length of the sequences. Alternatively, the identity can be measured over parts of the sequences. Such parts may be at least 350, at least 300, at least 250, at least 200, at least 250, at least 150, at least 100, at least 50, at least 30, at least 20, at least 15, at least 10 or at least 9 contiguous amino acids/nucleotides in length.

The skilled technician will appreciate how to calculate the percentage identity between two amino acid/polynucleotide/polypeptide sequences, for example, as described in online databases such as Wikiomics. In order to calculate the percentage identity between two amino acid/polynucleotide/polypeptide sequences, an alignment of the two sequences must first be prepared, followed by calculation of the sequence identity value.

The percentage identity for two sequences may take different values depending on:—(i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: ENDGAP=−1, and GAPDIST=4. Those skilled in the art will be aware that it may be necessary to vary these and other parameters for optimal sequence alignment.

Preferably, calculation of percentage identities between two amino acid/polynucleotide/polypeptide sequences is then calculated from such an alignment as (N/T)*100, where N is the number of positions at which the sequences share an identical residue, and T is the total number of positions compared including gaps but excluding overhangs. Hence, a most preferred method for calculating percentage identity between two sequences comprises (i) preparing a sequence alignment using the ClustalW program using a suitable set of parameters, for example, as Set out above; and (ii) inserting the values of N and T into the following formula: Sequence Identity =(N/T)*100.

Derivatives and analogues can also include conservative substitutions. Conservative substitutions can made according to Table 2. Amino acids in the same block in the second column and preferably in the same line in the third column may be substituted for each other:

TABLE 2

Conservative substitutions that can be made in accordance with the invention

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Modifications can be made to the amino acids in the polypeptide derived from a MHC class I HLA or derivative or analogue thereof. It will also be appreciated that modified amino acids may be substituted into HLA-A2 derived peptides, or derivatives or analogues thereof with a number of amino acid variants that may be known to those skilled in the art to form further preferred derivatives or analogues according to the invention. Such derivative or analogue peptides will have anti-allograft rejection activity provided that the modification does not significantly alter its chemical characteristics. For instance, hydrogens on the side chain amines of R or K may be replaced with methylene groups (—$NH_2$→—NH (Me) or —$N(Me)_2$). Furthermore, the N-terminal amino group of the peptides may be protected by reacting with a carboxylic acid and the C-terminal carboxyl group of the peptide may be protected by reacting with an amine. Other examples include glycosylation and phosphorylation.

Analogues of peptides according to the invention may also include peptide variants that increase or decrease the peptide's half-life in vivo. Examples of analogues capable of increasing the half-life of peptides used according to the invention include peptoid analogues of the peptides, D-amino acid derivatives of the peptides, and peptide-peptoid hybrids.

Polypeptides used according to the invention may be subject to degradation by a number of means (such as protease activity in biological systems). Such degradation may limit the bioavailability of the polypeptides, and hence the ability of the polypeptides to achieve their biological function. There are wide ranges of well-established techniques by which polypeptide analogues or derivatives that have enhanced stability in biological contexts can be designed and produced. Such polypeptide derivatives may have improved bioavailability as a result of increased resistance to protease-mediated degradation. Preferably, a polypeptide derivative or analogue suitable for use according to the invention is more protease-resistant than the polypeptide from which it is derived. Protease-resistance of a polypeptide derivative and the polypeptide from which it is derived may be evaluated by means of well-known protein degradation assays. The relative values of protease resistance for the peptide derivative and peptide may then be compared.

Peptoid analogues or derivatives of the polypeptides used in accordance with the invention may be readily designed from knowledge of the structure of the polypeptide. Commercially available software may be used to develop peptoid derivatives according to well-established protocols.

Retropeptoids, (in which all amino acids are replaced by peptoid residues in reversed order), are also able to mimic MHC class I HLA derived peptides or HLA-A2 derived peptides, or derivatives or analogues thereof. A retropeploid is expected to bind in the opposite direction in the ligand-binding groove, as compared to a polypeptide or peptoid-peptide hybrid containing one peptoid residue. As a result, the side chains of the peptoid residues are able point in the same direction as the side chains in the original peptide.

A further embodiment of an analogue of a polypeptide used according to the invention comprises D-amino acid forms of the polypeptide. The preparation of polypeptides using D-amino acids rather than L-amino acids greatly decreases any unwanted breakdown of such an agent by normal metabolic processes, decreasing the amounts of agent which needs to be administered, along with the frequency of its administration.

The polypeptides, derivative or analogues used in accordance with the invention may be made synthetically or by recombinant means. For example, a recombinant polypeptide may be produced by transfecting cells in culture with an expression vector comprising a nucleotide sequence encoding the polypeptide operably linked to suitable control sequences, culturing the cells, extracting and purifying the polypeptide produced by the cells. Methods for the recombinant production of polypeptides are well-known in the art (for example, Sambrook et al., 2001, Molecular Cloning: a laboratory manual, 3$^{rd}$ edition, Cold Harbour Laboratory Press).

Nucleic Acid Molecules

The invention concerns provides nucleic acids encoding a polypeptide, derivative or analogue discussed above.

The nucleic acid molecule may encode a polypeptide, which polypeptide forms a MHC class I HLA domain which is independently selected from a group of MHC class I HLA domains consisting of the α1 domain; the α2 domain; the α3 domain; the transmembrane domain; the cytosolic domain; or any combination thereof. For example, the nucleic acid molecule may encode the α1 domain and/or the α2 domain of a MHC class I HLA. Alternatively, the nucleic acid molecule may encode the α3 domain and/or the transmembrane domain of a MHC class I HLA.

The nucleic acid molecule may encode a polypeptide, which polypeptide forms an HLA-A2 domain which is independently selected from a group of HLA-A2 domains consisting of the α1 domain; the α2 domain; the α3 domain; the transmembrane domain; the cytosolic domain; or any combination thereof. For example, the nucleic acid molecule may encode the α1 domain and/or the α2 domain of HLA-A2. Alternatively, the nucleic acid molecule may encode the α3 domain and/or the transmembrane domain of HLA-A2.

The nucleic acid sequence of the HLA-A2 gene is identified as SEQ ID NO: 3. Hence, preferably the nucleic acid molecule comprises the sequence substantially as represented by SEQ ID NO: 3 (i.e. encodes the entire HLA-A2 protein as identified by SEQ ID NO: 1 or the mature HLA-A2 shown in SEQ ID NO: 2). The nucleic acid sequence of the α1 domain is represented by nucleotides 403-672 of SEQ ID NO: 3. Hence, the nucleic acid molecule may comprise the sequence substantially as represented by nucleotides 403-672 of SEQ ID NO: 3. The nucleic acid sequence of the α2 domain is represented by nucleotides 914-1189 of SEQ ID NO: 3. Hence, the nucleic acid molecule may comprise the sequence substantially as represented by nucleotides 914-1189 of SEQ ID NO: 3. The nucleic acid sequence of the α3 domain is represented by nucleotides 1790-2065 of SEQ ID NO: 3. Hence, the nucleic acid molecule may comprise the sequence represented by nucleotides 1790-2065 of SEQ ID NO: 3. The nucleic acid sequence of the transmembrane domain is represented by nucleotides 2165-2281 of SEQ ID NO: 3. Hence, the nucleic acid molecule may be identified by nucleotides 2165-2281 of SEQ ID NO: 3.

Preferred nucleic acid molecules encode a peptide independently selected from a group of peptides consisting of: p1; p2; p20; p21; p30; p39; p40; p50; p51; p52; p53; p45; p46; p50/51; p52/53; and p45/46.

Hence, preferred nucleic acid molecules comprise substantially the nucleotide sequence:

(SEQ ID NO: 75)
(a) 5'- CAC TCC ATG AGG TAT TTC TTC ACA TCC GTG TCC CGG CCC GGC CGC-3'.
This nucleic acid molecule encodes peptide p1.

(SEQ ID NO: 76)
(b) 5'- ATG AGG TAT TTC TTC ACA TCC GTG TCC CGG CCC GGC CGC GGG GAG-3'.
This nucleic acid molecule encodes peptide p2.

(SEQ ID NO: 77)
(c) 5'- CAC AAG TGG GAG GCG GCC CAT GTG GCG GAG CAG TTG AGA GCC TAC-3'.
This nucleic acid molecule encodes peptide p30.

(SEQ ID NO: 78)
(d) 5'- CAC GCT GTC TCT GAC CAT GAA GCC ACC CTG AGG TGC TGG GCC CTG- 3'.
This nucleic acid molecule encodes peptide p39.

(SEQ ID NO: 79)
(e) 5'- AGG TGC TGG GCC CTG AGC TTC TAC CCT GCG GAG ATC ACA CTG ACC -3'.
This nucleic acid molecule encodes peptide p40.

(SEQ ID NO: 80)
(f) 5'- AAG CCC CTC ACC CTG AGA TGG GAG CCG TCT TCC CAG CCC ACC ATC- 3'.
This nucleic acid molecule encodes peptide p50.

(SEQ ID NO: 81)
(g) 5'- CTC ACC CTG AGA TGG GAG CCG TCT TCC CAG CCC ACC ATC CCC ATC- 3'.
This nucleic acid molecule encodes peptide p51.

(SEQ ID NO: 82)
(h) 5'- CCC ACC ATC CCC ATC GTG GGC ATC ATT GCT GGC CTG GTT CTC TTT- 3'.
This nucleic acid molecule encodes peptide p52.

(SEQ ID NO: 83)
(i) 5'- ATC CCC ATC GTG GGC ATC ATT GCT GGC CTG GTT CTC TTT GGA GCT- 3'.
This nucleic acid molecule encodes peptide p53.

(SEQ ID NO: 84)
(j) 5'- GGA ACC TTC AG AAG TGG GCG GCT GTG GTG GTG CCT TCT GGA CAG -3'.
This nucleic acid molecule encodes peptide p45.

(SEQ ID NO: 85)
(k) 5'- TTC CAG AAG TGG GCG GCT GTG GTG GTG CCT TCT GGA CAG GAG CAG AGA-3'.
This nucleic acid molecule encodes peptide p46.

(SEQ ID NO: 86)
(l) 5'- AAG CCC CTC ACC CTG AGA TGG GAG CCG TCT TCC CAG CCC ACC ATC CCC ATC-3'.
This nucleic acid molecule encodes peptide p50/51.

(SEQ ID NO: 87)
(m) 5'- CCC ACC ATC CCC ATC GTG GGC ATC ATT GCT GGC CTG GTT CTC TTT GGA GCT-3'.
This nucleic acid molecule encodes peptide p52/53.

(SEQ ID NO: 88)
(n) 5'- GGA ACC TTC CAG AAG TGG GCG GCT GTG GTG GTG CCT TCT GGA CAG GAG CAG AGA-3'.
This nucleic acid molecule encodes peptide p45/46.

(SEQ ID NO: 89)
(o) 5-TCG GAC TGG CGC TTC CTC CGC GGG TAC CAC CAG TAC GCC TAC GAC-3'.
This nucleic acid molecule encodes peptide p20.

(SEQ ID NO: 90)
(p) 5'-TGG CGC TTC CTC CGC GGG TAC CAC CAG TAC GCC TAC GAC GGC AAG-3'.
This nucleic acid molecule encodes peptide p21.

Furthermore, preferred nucleic acid molecules encode peptide analogues: p39 analogue 1; p50/51 analogue; p52/53 analogue 1; p40 analogue; p45/P46 analogue 1; or p45/46 analogue 2. Hence, preferred nucleic acid molecules used comprise substantially the nucleotide sequence:

(SEQ ID NO: 91)
(q) 5'-CAC CCC ATC TCT GAC CAT GAG GCC ACC CTG AGG TGC TGG GCC CTG-3'.
This nucleic acid molecule encodes peptide analogue, p39 analogue 1.

(SEQ ID NO: 92)
(r) 5'-AAG CCC CTC ACC CTG AGA TGG GAG CCT TCT TCC CAG CCC ACC ATC CCC ATC-3'.
This nucleic acid moleculeencodes peptide analogue, p50/51 analogue 1.

```
                                            (SEQ ID NO: 93)
(s) 5'-CCC ACC ATC CCC ATC GTG GGC ATC ATT GCT GGC
CTG GTT CTC CTT GGA GCT-3'.
This nucleic acid molecule encodes peptide
analogue, p52/53 analogue 1.

(SEQ ID NO: 94)
(t) 5'-AGG TGC TGG GCC CTG GGC TTC TAC CCT GCG GAG
ATC ACA CTG ACC-3'.
This nucleic acid molecule encodes peptide
analogue, p40 analogue.

(SEQ ID NO: 95)
(u) 5'-GGA ACC TTC CAG AAG TGG GCG GCT GTG GTG GTG
CCT TCT GGA GAG GAG CAG AGA-3'.
This nucleic acid molecule encodes peptide
analogue, p45/46 analogue 1.

(SEQ ID NO: 96)
(v) 5'-GGA ACC TTC CAG AAG TGG GCG TCT GTG GTG GTG
CCT TCT GGA CAG GAG CAG AGA-3'.
This nucleic acid molecule encodes peptide
analogue, p45/46 analogue 2.
```

The nucleic acid molecule may comprise an isolated or purified nucleic acid molecule. The nucleic acid molecule may comprise a DNA sequence. The nucleic acid molecule may further comprise elements capable of controlling and/or enhancing its expression. The nucleic acid molecule may be contained within a suitable vector to form a recombinant vector. The vector may for example be a plasmid, cosmid or phage.

Other suitable vectors would be apparent to persons skilled in the art. By way of further example in this regard we refer to Sambrook et al., 2001, Molecular Cloning: a laboratory manual, 3$^{rd}$ edition, Cold Harbour Laboratory Press.

Such recombinant vectors are highly useful in the delivery systems for transforming cells with the nucleic acid molecule. Hence, the invention provides a host cell comprising a vector comprising any of the nucleic acids disclosed herein. For instance, the invention provides a host cell comprising a vector comprising nucleic acid molecule encoding a polypeptide derived from HLA-A2, or a derivative or analogue thereof.

Recombinant vectors may also include other functional elements. For instance, recombinant vectors can be designed such that the vector will autonomously replicate in a cell. In this case elements that induce nucleic acid replication may be required in the recombinant vector. Alternatively, the recombinant vector may be designed such that the vector and recombinant nucleic acid molecule integrates into the genome of a cell. In this case nucleic acid sequences, which favour targeted integration (e.g. by homologous recombination) are desirable. Recombinant vectors may also comprise DNA coding for genes that may be used as selectable markers in the cloning process. The recombinant vector may also further comprise a promoter or regulator to control expression of the gene as required.

The nucleic acid molecule may (but not necessarily) be one, which becomes incorporated in the DNA of cells of the subject being treated. Undifferentiated cells may be stably transformed leading to the production of genetically modified daughter cells (in which case regulation of expression in the subject may be required e.g. with specific transcription factors or gene activators). Alternatively, the delivery system may be designed to favour unstable or transient transformation of differentiated cells in the subject being treated. When this is the case, regulation of expression may be less important because expression of the DNA molecule will stop when the transformed cells die or stop expressing the protein (ideally when the required therapeutic effect has been achieved).

The delivery system may provide the nucleic acid molecule to the subject without it being incorporated in a vector. For instance, the nucleic acid molecule may be incorporated within a liposome or virus particle. Alternatively a "naked" nucleic acid molecule may be inserted into a subject's cells by a suitable means, e.g. direct endocytotic uptake. The nucleic acid molecule may be transferred to the cells of a subject to be treated by transfection, infection, microinjection, cell fusion, protoplast fusion or ballistic bombardment. For example, transfer may be by ballistic transfection with coated gold particles, liposomes containing the nucleic acid molecule, viral vectors (e.g. adenovirus) and means of providing direct nucleic acid uptake (e.g. endocytosis) by application of the nucleic acid molecule directly.

Alternative methods for identifying similar sequences will be known to those skilled in the art. The invention concerns using a nucleic acid molecule that hybridizes to a nucleic acid molecule that encodes a polypeptide derived from a MHC class I HLA, or a derivative or analogue thereof, or its complement. The invention preferably concerns using a nucleic acid molecule that hybridizes to a nucleic acid molecule that encodes a polypeptide derived from HLA-A2, or a derivative or analogue thereof, or its complement. For example, a substantially similar nucleotide sequence will be encoded by a sequence which hybridizes to the sequences shown in SEQ ID NO: 3 or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C.

Due to the degeneracy of the genetic code, it is clear that any nucleic acid sequence could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will known the nucleotide sequences encoding these amino acids. Reference is also made to Table 2 above.

Therapy

The invention also concerns using the polypeptides, derivatives, analogues and nucleic acids described herein in therapy. In particular, the invention provides a polypeptide derived from a MHC class I HLA, or a derivative or analogue thereof, for use as a medicament. The invention also provides a nucleic acid molecule encoding a polypeptide, derivative or analogue of the invention, or a nucleic acid molecule that hybridizes to a nucleic acid molecule encoding a polypeptide, derivative or analogue of the invention or its complement under stringent conditions, for use as a medicament. The invention further provides use of:

(a) at least one polypeptide derived from a MHC class I HLA, or a derivative or analogue thereof;

(b) at least one nucleic acid molecule encoding a polypeptide, derivative or analogue of (a); or (c) at least one nucleic acid molecule that hybridizes to a nucleic acid molecule of (b) or its complement under stringent conditions;

for the manufacture of a medicament for the treatment or prevention of a condition characterised by allosensitisation. Any of the polypeptides, derivatives, analogues and nucleic acids described above may be used.

The invention also provides a polypeptide derived from HLA-A2, or a derivative or analogue thereof for use as a medicament. The invention also provides use of a polypeptide derived from HLA-A2, or a derivative or analogue thereof, for the manufacture of a medicament for the treatment or prevention of a condition characterised by allosensitisation. The invention further provides a method of treating or preventing a condition characterised by allosensitisation, the method comprising administering to a subject in need of such treatment, a therapeutically effective amount of a polypeptide derived from HLA-A2, or a derivative or analogue thereof.

Accordingly, in a most preferred embodiment, there is provided a polypeptide derived from the α3 domain or the transmembrane domain of HLA-A2, or a derivative or analogue thereof, for use as a medicament. Furthermore, in another most preferred embodiment, there is provided use of a polypeptide derived from the α3 domain or the transmembrane domain of HLA-A2, or a derivative or analogue thereof, for the manufacture of a medicament for the treatment or prevention of a condition characterised by allosensitisation. It is especially preferred that the medicament is for the treatment or prevention of allograft rejection.

It will be appreciated that a polypeptide derived from HLA-A2, or a derivative or analogue thereof, used according to the invention also represent favourable agents capable of being administered by techniques involving cellular expression of nucleic acid sequences encoding such molecules. Such methods of cellular expression are particularly suitable for medical use in which the therapeutic effects of the HLA-A2 derived peptides or derivatives or analogues derived therefrom are required over a prolonged period. Hence, the invention also provides a nucleic acid molecule encoding a polypeptide derived from HLA-A2, or a derivative or analogue thereof for use as a medicament.

Furthermore, the invention also provides use of a nucleic acid molecule encoding a polypeptide derived from HLA-A2, or a derivative or analogue thereof for the manufacture of a medicament for the treatment or prevention of a condition characterised by allosensitisation. Preferably, the medicament is for the treatment of prevention of allograft failure or rejection.

By the term "allosensitisation", we mean the development of antibodies to foreign antigens, which results in a number of disease conditions. Often patients suffering from such conditions require repeated blood transfusions. However, allosensitisation can often render patients almost impossible to transfuse, and can be life-threatening. Hence, conditions that are characterised by allosensitisation include thalassemia, and blood transfusions HLA-A2 is known to be a major factor in transplant organ rejection, a medical problem in which the inventor was particularly interested, and accordingly, the inventor has found that HLA-A2 derived peptides or derivatives or analogues thereof is particularly useful for treating or preventing allograft rejection By the term "allograft", we mean a transplant process wherein a tissue or organ is taken from one individual (i.e. a donor) and placed into another genetically non-identical individual (i.e. a recipient). Both the donor and the recipient are members of the same species. The term allograft may also be used to describe the transplanted tissue or organ.

By the term "tissue", we mean a group of similar cells specialised to perform similar functions, for example, muscle, nerve, bone, cartilage, skin, or connective tissue.

By the term "organ", we mean a bodily structure containing different tissues that are organized to carry out a specific function of the body, for example, the heart, lungs, brain, skin, liver, etc.

While the inventor does not wish to be bound by any hypothesis, they believe that use of a polypeptide derived from HLA-A2 or other MHC class I HLAs, such as HLA-B or HLA-C, or a derivative or an analogue thereof, will have beneficial effects on transplant outcome, not only by inhibiting the formation of anti-HLA antibodies, but also by inhibiting other recognised pathways of allograft rejection. This may occur not simply by directly inhibiting the activation of certain effector cells, which damage allograft or organ transplants, but also by activating regulatory cells that inhibit these effector cells. Accordingly, the inventor believes that the surprising findings regarding the pattern of reactivity to a peptide derived from HL-A2 or a derivative or an or analogue thereof suggest that such peptides or analogues may be harnessed in a method of treatment or therapy to prevent conditions characterised by allosensitisation, for example, transfusion.

The inventor believes that the surprising findings regarding the pattern of reactivity to a polypeptide derived from HLA-A2, or a derivative or analogue thereof also suggest that such peptides or analogues derived therefrom may be harnessed in a method for treating or preventing allograft rejection in transplant patients, not only when there is an organ mismatched for HLA-A2, but also in the majority of cases of transplantation. The same is true for polypeptides derived from other MHC class I HLAs or derivatives or analogues thereof. Hence, it is especially preferred that the method be used to treat allograft rejection.

The inventor believes that the identification of such peptide-based epitopes allows the development of a peptide-based therapy, which comprises administering to a subject a mixture of peptides that could be used in a range of individuals with different MHC class II epitopes.

Accordingly, it is preferred that the method of the invention comprises administering to a subject in need of treatment a therapeutically effective amount of at least one polypeptide, or derivative or analogue thereof, and preferably, a plurality of polypeptides, derivatives or analogues thereof, which are derived from a MHC class I HLA. A combination or mixture of polypeptides derived from a MEC class I HLA, or derivatives or analogues thereof, may be administered to the subject. A combination or mixture of any of the polypeptides discussed above may be administered.

Accordingly, it is especially preferred that the method of the invention comprises administering to a subject in need of treatment a therapeutically effective amount of at least one polypeptide, or derivative or analogue thereof, and preferably, a plurality of polypeptides, derivatives or analogues thereof, which are derived from HLA-A2. A combination or mixture of polypeptides derived from HLA-A2, or derivatives or analogues thereof, may be administered to the subject.

The at least one polypeptide, derivative or analogue, or plurality thereof, may be administered to a sensitised patient, i.e. one who has made anti-HLA antibody. Alternatively, the at least one polypeptide, derivative or analogue, or mixture thereof, may be administered to an individual prior to transplantation or transfusion in order to abrogate sensitisation to HLA. In considering desensitisation, one may expect peptides p39 (SEQ ID NO: 42), p50/51 (SEQ ID NO: 57) and p52/53 (SEQ ID NO: 58) to benefit individuals who do not express these sequences themselves, i.e. a subject who express HLA-A1, HLA-A3, HLA-A11, HLA-A23, HLA-A24, HLA-A30, or HLA-A36, and who subsequently receive (or who have previously received) mismatched transplants (or transfusions) expressing HLA-A2, HLA-A25, HLA-A26, HLA-A29, HLA-A31, HLA-A32, HLA-A33, HLA-A34, HLA-A43, HLA-A66, HLA-A68, HLA-A69, HLA-A74.

Hence, it will be appreciated from the foregoing that preferred polypeptides, derivatives or analogues thereof which are derived from the non-polymorphic region of HLA-A2 are also expressed by many other HLA-A molecules, and not just HLA-A2, by acting as sites of potential cross-reactivity between different HLA molecules. Hence, surprisingly, the inventor believes that the benefits of using such peptides in methods according to the invention, and in particular for uses in treating or preventing conditions characterised by allosensitisation, and particularly, allograft rejection, and alloantibody synthesis, may be much wider than to HLA-A2 antigen alone. Accordingly, the inventor believes that the implications of their findings are much broader than solely help for antibody production, but relate to immune mechanisms of graft rejection per se, and are wider than target HLA-A2, extending to responses to transplantation antigens in general.

Hence, in a further aspect, there is provided use of an alloantigen, or a polypeptide derived therefrom, or a derivative or analogue thereof, for the manufacture of a medicament for the treatment or prevention of a condition characterised by allosensitisation. Preferably, the medicament is for the treatment of allograft rejection. Preferably, the alloantigen, or polypeptide derived therefrom, or derivative or analogue thereof may be independently selected from a group consisting of HLA-A2, HLA-A25, HLA-A26, HLA-A29, HLA-A31, HLA-A32, HLA-A33, HLA-A34, HLA-A43, HLA-A66, HLA-A68, HLA-A69, HLA-A74, HLA-A1, HLA-A3, HLA-A11, HLA-A24, HLA-A30, HLA-A36, HLA-A80, HLA-A1, HLA-A3, HLA-A11, and HLA-A23, or any combination thereof. Preferred polypeptides derived from the alloantigen are discussed above.

The therapeutically effective amount of the polypeptide derived from the MHC class I HLA, such as HLA-A2, or a derivative or analogue thereof, may be administered to the subject after the subject has been given an allograft, or a transplant, or a transfusion. However, it is most preferred that it is administered to the subject before the subject has been given an allograft, or transplant, or transfusion. Hence, preferably, the medicament is administered to a subject prior to antigen exposure, for example at the time of transplant listing or transfusion. Hence, the method effectively comprises administering a vaccine or so-called 'negative vaccine' comprising a therapeutically effective amount of a polypeptide derived from a MHC class I HLA, or a derivative or analogue thereof. The method also effectively comprises administering a vaccine or so-called 'negative vaccine' comprising a therapeutically effective amount of a polypeptide derived from HLA-A2, or a derivative or analogue thereof.

Therefore, there is provided a vaccine comprising a polypeptide derived from a MHC class I HLA, or a derivative or analogue thereof. There is also provided a vaccine comprising a polypeptide derived from HLA-A2, or a derivative or analogue thereof.

The inventor believes that a course of treatment would be undertaken with progressively higher doses of the 'negative vaccine', at approximately weekly intervals (but it may be administered daily, or every other day, for example), over the course of approximately 1 to 6 months. The amount of polypeptide, derivative or analogue administered may be in the region of about 1 µg to 1 mg.

It will be appreciated that the invention is for the prevention or treatment of a condition characterised by allosensitisation, rejection of an allograft, or alloimmunisation secondary to transfusion. It is common practise to transplant tissues or organs from a donor subject to a recipient subject. Hence, the invention extends to the treatment or prevention of failure or rejection of any tissue, such as muscle, nerve, bone, bone marrow, cartilage, skin, or connective tissue, or any organ such as the heart, lungs, brain, skin, liver, etc. or alloimmunisation secondary to transfusion.

However, the inventor focussed their research on patients suffering from end stage renal failure. Hence, it is especially preferred that the medicament may be used for the treatment or prevention of rejection of a kidney transplant, or alloimmunisation secondary to such a kidney transplant, or prior to transfusion. Furthermore, the subject being treated in the method of invention may be suffering from kidney transplant rejection. Accordingly, it is preferred that the allograft or transplant comprises a kidney or a portion thereof.

The following discussion concerning monotherapy, combination therapy, timing of administration, compositions, routes of administration, release devices and dosages relates to polypeptides derived from HLA-A2, or derivatives or analogues thereof. However, it also applies to polypeptides derived from another MHC class I HLAs such as HLA-B or HLA-C, derivatives or analogues thereof, and nucleic acids encoding the same.

It will be appreciated that the polypeptide derived from HLA-A2 or a derivative or analogue thereof, or nucleic acid molecule encoding HLA-A2 or a polypeptide, derivative or analogue thereof, may be used in a monotherapy (i.e. use of a polypeptide derived from HLA-A2 or a derivative or analogue thereof or nucleic acid molecule encoding same alone to prevent and/or treat a allograft failure or rejection). Alternatively, a polypeptide derived from HLA-A2 or a derivative or analogue thereof or nucleic acid molecule encoding same may be used as an adjunct, or in combination with known therapies for treating a condition characterised by allosensitisation, such as, allograft rejection, or preventing allosensitisation, such as conventional immunosuppression with calcineurin inhibitors, TOR inhibitors or antibodies targeting lymphocyte antigens.

A therapeutically effective amount of the polypeptide derived from HLA-A2 or a derivative or analogue thereof, or nucleic acid molecule encoding polypeptide derived from HLA-A2 or a derivative or analogue thereof may be administered to the subject after the subject has been given an allograft or transplant. Alternatively, the at least one peptide or mixture thereof may be administered to a subject prophylactically, i.e. to attenuate responses to HLA.

While the inventor does not wish to be bound by any hypothesis, they believe that if the mechanism of attenuation involves dominant negative regulation, then this may also diminish the response to other mismatched antigens, for example, when an HLA-A2 mismatched transplant is implanted. Hence, it is preferred that a therapeutically effective amount of the polypeptide derived from HLA-A2 or a derivative or analogue thereof, or nucleic acid molecule encoding polypeptide derived from HLA-A2 or a derivative or analogue thereof is administered to the subject before the subject has been given an allograft or transplant, i.e. similar to a vaccination.

The inventor envisages administration to a subject at least one, and preferably a plurality of peptides derived from HLA-A2 or derivatives or analogues thereof. They believe that the or each peptide, derivative or analogue thereof may be used to down-regulate the response to alloantigen, and therefore improve the outcome of transplantation and/or permit the desensitisation of patients who have made anti-HLA antibody.

The polypeptide derived from HLA-A2 or a derivative or analogue thereof, or nucleic acid molecule encoding a polypeptide derived from HLA-A2 or a derivative or analogue thereof may be combined in compositions having a number of different forms depending, in particular, on the manner in which the composition is to be used.

For example, the composition may be in the form of a powder, tablet, capsule, liquid, ointment, cream, gel, hydrogel, aerosol, spray, micelle, transdermal patch, liposome or any other suitable form that may be administered to a subject in need of treatment. It will be appreciated that the vehicle of the composition of the invention should be one which is well tolerated by the subject to whom it is given, and preferably enables delivery of the polypeptide derived from HLA-A2 or a derivative or analogue thereof, or nucleic acid molecule encoding polypeptide derived from HLA-A2 or a derivative or analogue thereof to the immune system. The vehicle of the composition of the invention should be one which is well tolerated by the subject to whom it is given, and preferably enables delivery of the polypeptide derived from HLA-A2 or a derivative or analogue thereof, or nucleic acid molecule encoding polypeptide derived from HLA-A2 or a derivative or analogue thereof to the immune system.

Compositions comprising a polypeptide derived from HLA-A2 or a derivative or analogue thereof, or nucleic acid molecule encoding a polypeptide derived from HLA-A2 or a derivative or analogue thereof used according to the invention may be used in a number of ways. For instance, oral administration may be required in which case the polypeptide derived from HLA-A2 or a derivative or analogue thereof or nucleic acid molecule may be contained within a composition that may, for example, be ingested orally in the form of a tablet, capsule or liquid. The composition comprising polypeptide derived from HLA-A2 or a derivative or analogue thereof or nucleic acid molecule may be administered by inhalation (e.g. intranasally). Compositions may be formulated for topical use. For instance, ointments may be applied to the skin.

The polypeptide derived from HLA-A2 or a derivative or analogue thereof or nucleic acid molecule may also be incorporated within a slow or delayed release device. Such devices may, for example, be inserted on or under the skin, and the composition may be released over weeks or even months. Such devices may be particularly advantageous when long-term treatment with polypeptide derived from HLA-A2 or a derivative or analogue thereof or nucleic acid molecule used according to the invention is required and which would normally require frequent administration (e.g. at least daily injection).

However, in a most preferred embodiment, the composition comprising a polypeptide derived from HLA-A2 or a derivative or analogue thereof or nucleic acid molecule is administered to a subject in need of such treatment by injection into the blood stream. Injections may be intravenous (bolus or infusion) or subcutaneous (bolus or infusion), or intradermal (bolus or infusion).

It will be appreciated that the amount of polypeptide derived from HLA-A2 or a derivative or analogue thereof or nucleic acid molecule that is required is determined by its biological activity and bioavailability which in turn depends on the mode of administration, the physicochemical properties of the polypeptide derived from HLA-A2 or a derivative or analogue thereof or nucleic acid molecule employed and whether the polypeptide derived from HLA-A2 or a derivative or analogue thereof or nucleic acid molecule is being used as a monotherapy or in a combined therapy. The frequency of administration will also be influenced by the above-mentioned factors and particularly the half-life of polypeptide derived from HLA-A2 or a derivative or analogue thereof or nucleic acid molecule within the subject being treated.

Optimal dosages to be administered may be determined by those skilled in the art, and will vary with the particular polypeptide derived from HLA-A2 or a derivative or analogue thereof or nucleic acid molecule in use, the strength of the preparation, the mode of administration, and the advancement of the disease condition. Additional factors depending on the particular subject being treated will result in a need to adjust dosages, including subject age, weight, gender, diet, and time of administration.

Known procedures, such as those conventionally employed by the pharmaceutical industry (e.g. in vivo experimentation, clinical trials, etc.), may be used to establish specific formulations of polypeptide derived from HLA-A2 or a derivative or analogue thereof or nucleic acid molecule used according to the invention and precise therapeutic regimes (such as daily doses of the polypeptide derived from HLA-A2 or a derivative or analogue thereof or nucleic acid molecule and the frequency of administration).

Generally, a daily dose of between 0.001 μg/kg of body weight and 100 μg/kg of body weight of polypeptide derived from HLA-A2 or a derivative or analogue thereof or nucleic acid molecule may be used for the prevention and/or treatment of allograft failure or rejection, depending upon which specific polypeptide derived from HLA-A2 or a derivative or analogue thereof or nucleic acid molecule is used. More preferably, the daily dose is between 0.01 μg/kg of body weight and 10 μg/kg of body weight, and most preferably, between approximately 0.01 μg/kg and 1 μg/kg.

Daily doses may be given as a single administration (e.g. a single daily injection). Alternatively, the polypeptide derived from HLA-A2 or a derivative or analogue thereof or nucleic acid molecule used may require administration twice or more times during a day. As an example, polypeptide derived from HLA-A2 or a derivative or analogue thereof or nucleic acid molecule may be administered as two (or more depending upon the severity of the condition) daily doses of between 0.07 μg and 7000 μg (i.e. assuming a body weight of 70 kg). A patient receiving treatment may take a first dose upon waking and then a second dose in the evening (if on a two dose regime) or at 3 or 4 hourly intervals thereafter. Alternatively, a slow release device may be used to provide optimal doses to a patient without the need to administer repeated doses.

The invention also provides a pharmaceutical composition comprising a therapeutically effective amount of a polypeptide, derivative or analogue of the invention or a nucleic acid molecule of the invention, and optionally a pharmaceutically acceptable vehicle. The invention preferably provides a pharmaceutical composition comprising a therapeutically effective amount of polypeptide derived from HLA-A2 or a derivative or analogue thereof, or nucleic acid molecule encoding polypeptide derived from HLA-A2 or a derivative or analogue thereof, and optionally, a pharmaceutically acceptable vehicle. The composition can comprise one or more of any of the polypeptides, derivatives, analogues or nucleic acids discussed above.

The invention further provides a process for making a pharmaceutical composition comprising combining a therapeutically effective amount of a polypeptide, derivative or analogue of the invention or a nucleic acid molecule of the invention and a pharmaceutically acceptable vehicle. The invention preferably provides a process for making a pharmaceutical composition comprising combining a therapeutically effective amount of a polypeptide derived from HLA-A2 or a derivative or analogue thereof or nucleic acid molecule encoding a polypeptide derived from HLA-A2 or a derivative or analogue thereof, and a pharmaceutically acceptable vehicle.

The following discussion concerning amounts, vehicles and routes of administration relates to polypeptides derived from HLA-A2, or derivatives or analogues thereof. However, it also applies to polypeptides derived from other MHC class I HLAs, such as HLA-B or HLA-C, derivatives or analogues thereof, and nucleic acids encoding the same.

The amount of the polypeptide derived from HLA-A2 or a derivative or analogue thereof or nucleic acid molecule may be from about 0.01 µg to about 800 µg and preferably, from about 0.01 mg to about 500 µg. It is preferred that the amount of polypeptide derived from HLA-A2 or a derivative or analogue thereof or nucleic acid molecule is an amount from about 0.01 mg to about 250 mg, more preferably, about 0.1 mg to about 60 mg, and most preferably, from about 0.1 mg to about 20 mg. A "therapeutically effective amount" is any amount of polypeptide derived from HLA-A2 or a derivative or analogue thereof or nucleic acid molecule which, when administered to a subject provides prevention and/or treatment of a condition characterised by allosensitisation, such as, allograft failure or rejection. A "subject" may be a vertebrate, mammal, or domestic animal, and is preferably, a human being.

A "pharmaceutically acceptable vehicle" as referred to herein is any physiological vehicle known to those of ordinary skill in the art useful in formulating pharmaceutical compositions. In one embodiment, the pharmaceutically acceptable vehicle may be a solid and the composition may be in the form of a powder or tablet. A solid pharmaceutically acceptable vehicle may include one or more substances which may also act as flavouring agents, lubricants, solubilisers, suspending agents, fillers, glidants, compression aids, binders or tablet-disintegrating agents; it can also be an encapsulating material. In powders, the vehicle is a finely divided solid that is in admixture with the finely divided active polypeptide derived from HLA-A2 or a derivative or analogue thereof or nucleic acid molecule. In tablets, the active polypeptide derived from HLA-A2 or a derivative or analogue thereof or nucleic acid molecule is mixed with a vehicle having the necessary compression properties in suitable proportions and compacted in the shape and size desired. The powders and tablets preferably contain up to 99% of the active polypeptide derived from HLA-A2 or a derivative or analogue thereof or nucleic acid molecule. Suitable solid vehicles include, for example, calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, in a preferred embodiment, the pharmaceutical vehicle is a liquid and the pharmaceutical composition is in the form of a solution. Liquid vehicles are used in preparing solutions, suspensions, emulsions, syrups, elixirs and pressurized compositions. The active polypeptide derived from HLA-A2 or a derivative or analogue thereof or nucleic acid molecule may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be halogenated hydrocarbon or other pharmaceutically acceptable propellant.

Liquid pharmaceutical compositions which are sterile solutions or suspensions can be utilized by for example, intramuscular, intrathecal, epidural, intraperitoneal, intravenous and particularly subcutaneous, intracerebral or intracerebroventricular injection. The polypeptide derived from HLA-A2 or a derivative or analogue thereof or nucleic acid molecule may be prepared as a sterile solid composition that may be dissolved or suspended at the time of administration using sterile water, saline, or other appropriate sterile injectable medium. Vehicles are intended to include necessary and inert binders, suspending agents, lubricants, flavourants, sweeteners, preservatives, dyes, and coatings.

The polypeptide derived from HLA-A2 or a derivative or analogue thereof or nucleic acid molecule may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like.

The polypeptide derived from HLA-A2 or a derivative or analogue thereof or nucleic acid molecule used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Agents Increasing HLA Activity

It will be appreciated that the therapeutic effects of polypeptides derived from HLA-A2 or derivatives or analogues thereof may be mediated "indirectly" by agents that increase the activity of such peptides or analogues. Hence, the present invention also provides the first medical use of such agents.

Thus, the invention also provides an agent capable of increasing the biological activity of a polypeptide derived from HLA-A2, or a derivative or analogue thereof, for use as a medicament.

Agents capable of increasing the biological activity of HLA-A2 derived peptides or derivatives or analogues thereof may achieve their effect by a number of means. For instance, such agents may increase the expression of HLA-A2 derived peptides, or derivatives or analogues thereof. Alternatively, or additionally, such agents may increase the half-life of a polypeptide derived from HLA-A2, or a derivative or analogue thereof in a biological system, for example, by decreasing turnover of HLA-A2 derived peptides or derivatives or analogues thereof. Due to their increased biological activity, a polypeptide derived from HLA-A2, or a derivative or analogue thereof are of utility as anti-allograft rejection agents.

In Vitro Methods

The invention also provides an in vitro method of stimulating T cells, the method comprising contacting the T cells with:

(a) a polypeptide derived from a MHC class I HLA, or a derivative or analogue thereof;

(b) a nucleic acid molecule encoding a polypeptide, derivative or analogue of (a); or (c) a nucleic acid molecule that hybridizes to a nucleic acid molecule of (b) or its complement under stringent conditions;

under conditions which allow stimulation of the T cells and thereby stimulating the T cells.

Any of the polypeptides, derivatives, analogues or nucleic acids described above can be used in this method. Suitable conditions for the stimulation of T cells are known in the art.

This method of the invention has various uses. For instance, the method could be carried out on a sample of T cells from a transplant patients undergoing chronic rejection of the graft. A positive response by the patient's T cells to the HLA-derived polypeptides could suggest that the chronic rejection involves an immune system component. A negative response by the patient's T cells to the HLA-derived polypeptides could suggest that the chronic rejection is due to non-immune system based mechanism, such as cyclosporin nephrotoxicity.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made to the following Examples.

EXAMPLES

Overview

The inventor realised that the presence of anti-HLA antibody contraindicates renal transplantation, and post-transplantation is associated with allograft failure. Furthermore, the acquisition of HLA specific antibody implies T cell help through indirect allorecognition, and this pathway also plays a role in rejection independent to alloantibody synthesis. The inventor therefore systematically studied responses to a single MHC class I molecule, HLA-A2, which is a common target antigen in sensitised patients on the organ transplantation waiting list, i.e. patients who have made HLA-A2 antibodies.

In both Examples 1 and 2, the inventor designed a series of 60 overlapping 15mer peptides that spanned the primary sequence of HLA*020101. However, only 53 (p1-p53) could be synthesised using F-moc technology. The binding affinity of these 53 peptides to 13 different MHC class II molecules was then studied by ELISA. The inventor found that peptides from several locations along the HLA-A2 molecule exhibited promiscuous binding to MHC.

The 30 peptides that bound MHC class II were then used to stimulate peripheral blood mononuclear cells (PBMC) from 40 transplant-listed patients with known antibody sensitisation histories. Responses were assessed by γ-interferon ELISPOT (enzyme-linked immunosorbent assay), and the findings are summarised below.

In Example 3, the inventor compared the sequence of some of the 15mer peptides from HLA-A2 with sequences in other HLA polypeptides to find additional sequences of relevance.

Example 1

Materials & Methods

1) In Silico Epitope Prediction

In order to minimise the numbers of peptides to be screened in direct MHC-peptide binding assays and to maximise discrimination in areas likely to be of interest, a systematic approach was adopted involving an initial computer based evaluation of the primary amino acid sequence of the HLA-A*0201 molecule, i.e. HLA-A2. The DNA sequence of HLA-A2 is identified as SEQ ID NO: 3 and the amino acid sequence is identified as SEQ ID NOs: 1 and 2.

Referring to FIG. 1, there is shown a schematic representation of the extracellular portion of the human class I histocompatability molecule, HLA-A2. The stretches of beta conformation are represented by broad arrows (pointing N to C terminal). Regions of alpha helix are shown as helical ribbons. The pairs of spheres represent disulphide bridges. The molecule of beta-2-microglobulin ($\beta_2$m) is bound to the junction of the α1 and α2 domains, and to the α3 domain by non-covalent interactions only. Not shown in FIG. 1 is the presence of a short peptide bound non-covalently in the groove between the alpha helices of α1 and α2 domains. The combination of peptide and adjacent portions of alpha helices makes up the epitope seen by CD8+ T cells. The transmembrane and cytosolic portion of the HLA-A2 molecule are not shown, but it will be appreciated that the transmembrane portion extends from about amino acid residue 283 onwards.

The analysis of the primary amino acid sequence of the HLA-A2 molecule was performed using the widely available algorithm TEPITOPE (Sturniolo, T., et al., Generation of tissue-specific and promiscuous HLA ligand databases using DNA microarrays and virtual HLA class II matrices. Nat Biotechnol, 1999. 17(6): p. 555-61). The programme was used to identify sequences that share HLA-binding motifs with previously identified and characterised epitopes. However, because such in silico approaches may omit epitopes that do not conform to standard motifs, the inventor conducted additional literature and database searches in order to identify all previously reported MHC class II-binding sequences from the HLA-A2 molecule.

2) Solubility Analysis

Sequences predicted to bind to MHC class II molecules were evaluated for solubility using predictive computer-based algorithms such as that at the online database EXPASY. The inventor believed that such solubility analysis was an important precursor to physical binding assays as it allowed identification of any peptide sequences that contain important, naturally processed, but nominally insoluble MHC-binding core motifs. Frequently, such epitopes can be rendered soluble by the addition of various flanking residues that occur naturally in the source protein (HLA-A*0201 in this case). This approach avoided time-consuming and costly synthesis of peptides that would not generate data in MHC-binding assays, and would therefore have ultimately been of little use for clinical intervention.

3) Peptide Synthesis

A series of 60 overlapping 15mer peptides that spanned the primary sequence of HLA*020101 was designed. However, only 53 (p1-p53) could be synthesised. Hence, a series of 53 synthetic overlapping 15mers offset by 2 to 5 residues, corresponding to soluble, MHC class II-binding motifs, were generated as HCl salts by standard Fmoc chemistry and supplied as lyophilised powder (NeoMPS SA, Strasbourg, France). Peptides were reconstituted in $10^{-4}$M HCl.

Referring to FIG. 2, there are shown details of all 53 peptides, designated p1 to p53. FIG. 2 shows the position, molecular weight and sequence of each peptide.

4) Peptide Binding to Purified MHC Molecules In Vitro

The peptide-MHC binding assay was a competition assay in which "query" peptides are titrated into wells containing immobilised, purified MHC molecules and known concentrations of biotinylated reference peptides that are known to bind to the molecule in question with high affinity.

The MHC molecules for study included: DRB1*0101 (DR1), DRB1*0301 (DR3), DRB1*0401 (DR4), DRB1*0701 (DR7), DRB1*1101 (DR11), DRB1*1301 (DR13), DRB1*1501 (DR15); DRB3*0101 (DRB3), HLA-DRB4*0101 (DRB4) and HLA-DRB5*0101 (DRB %); HLA-DPA1*0103/DPB1*0401 (DP401) and HLA-DPA1*0103/DPB1*0402 (DP402). These were undertaken at CEA-Saclay using techniques that are well established in his laboratory for the analysis of other antigens (Texier, C., et al., HLA-DR restricted peptide candidates for bee venom immunotherapy. J Immunol, 2000. 164(6): p. 3177-84).

Binding experiments were repeated on three separate occasions to confirm results. Results were expressed as both nm IC50 and as the ratio of binding of each peptide compared to a reference peptide (also screened in the assay) of known high affinity binding to each particular MHC allele.

Binding ratios of less than 20 are considered high affinity binders and those with a ratio of 21-100, moderate binders. Previous data indicated that important T cell epitopes only rarely have binding affinities outside of these windows, although there are exceptions.

Referring to FIG. 4, there is shown the binding studies data generated. These data show the ratio of the 50% inhibitory concentration (IC50) of test peptide compared to the 50% binding concentration of control peptide, to the MHC class II molecule under investigation.

5) In vitro Functional Analysis—Immune Responses of Peripheral Blood Mononuclear Cells The studies described above identified that a wide range of peptides bound to at least one MHC class II molecule, although a limited number showed promiscuous binding. On the basis of these studies, the number of peptides for future study was reduced from 53 to 30. 23 peptides which showed little or no significant binding to MHC class II, that is the ratio of their binding affinity to that of control peptide was >100, were not studied further. This was undertaken in order to limit the amount of blood that was required from each patient under study.

The presence of lymphocytes specific for any given peptide was determined using γ interferon ELISPOT (enzyme-linked immunosorbent assay) with 500,000 peripheral blood mononuclear cells per well in quadruplicate. (Briefly, peripheral blood mononuclear cells (PBMCs) were separated from heparinised whole blood by density centrifugation. These were washed and resuspended in complete culture medium (containing 10% AB serum). Cells were cultured with individual peptides in 96 well γ-interferon ELISPOT plates, (Mabtech, Nacka Strand, Sweden) in 100 µl complete medium, with peptide at a concentration of 4 µg and 20 µg/ml. The frequency of γ-interferon producing cells was evaluated by ELISPOT, as shown in FIG. 7 for a single example patient. The frequency and specificity of peptide specific responses was then compared between individuals in the sensitised and unsensitised groups.

6) Recruitment of Subjects for Study

Patient subjects were recruited from the University Hospital Birmingham renal transplant waiting list Patients on dialysis at University Hospital Birmingham were approached initially, following receipt of local research ethical committee approval. Subjects who were currently receiving immunosuppression or who had a haemoglobin<10 g/dl were excluded. Having obtained fully informed consent, 50 ml of venous blood was obtained at the time of routine venesection.

The HLA type determined by standard molecular techniques was available for each subject from routine clinical assessment by the West Midlands Blood Transfusion Service Immunogenetics Laboratory. This laboratory characterised anti-HLA antibody specificities using standard flow-cytometric based techniques including the use of monospecific beads, within the context of routine clinical practice and provided relevant historical information on antibody specificities for the respective subjects.

Results

The inventor examined 5 groups of patients summarised in the Table below.

TABLE 3

| Patient groups | | |
|---|---|---|
| Patient anti-HLA | Patient HLA type | |
| antibody status | A2+ | A2− |
| Sensitised with anti-HLA A2 | | 12/15 (Group1) |
| Sensitised no anti-HLA A2 | 0/6 (Group 2) | 1/5 (Group 3) |
| Unsensitised | 1/6 (Group 4) | 2/8 (Group 5) |

The presence or absence of antibodies was determined using standard solid phase, flow cytometric based techniques ('Luminex™'). The denominator in each group identifies the number of patients studied and the numerator, the number in each group that responded to at least 1 peptide.

In group 1, 10 patients responded to peptides p20/21. This is from the highly polymorphic region of HLA-A2. Closely overlapping peptides have been eluted from human B lymphocyte HLA DR1, i.e. it has been shown to be a 'naturally processed' and presented endogenous protein. A larger peptide containing these sequences has also been identified as a DR15 restricted epitope in a patient who rejected an A2 positive kidney.

In group 1: 10 patients responded to peptides derived from the α3 and transmembrane domains that show very limited polymorphism. These peptides were most commonly p39 (192-206), p50/51(268-284) and p52/53 (280-296), although a small number of other sites also resulted in responses including p40 (202-216) and p45/46 (239-256). These peptides have not previously been identified as T cell epitopes. In two of the patients, some of the α3/transmembrane peptides were autologous epitopes, for example patient 1 is A68 positive and therefore shares the sequences of p39, p52/53 with HLA-A2.

Referring to FIG. 5, there is shown the sequence of peptide 39. The left hand circle shows the HLA types in which the sequence of the homologous region is shared with HLA-A2 and the right hand circle, those HLA types in which the homologous region is different from HLA-A2, and the two amino acids by which they differ (alanine to proline at 193 and valine to isoleucine at 194).

Referring to FIG. 6, there is shown the sequences of peptides p50 and p51. The left hand circle shows the HLA types in which the sequence of the homologous region is shared with HLA-A2 and the other circles, those in which the homologous region is different from HLA-A2, and the amino acids by which they differ, (proline to leucine at 276, for A1, A3, A11, A30, A36 etc).

Referring to FIG. 7, there is shown the sequences of peptides p52 and p53. The left hand circle shows the HLA types in which the sequence of the homologous region is shared with HLA-A2 and the other circles, those in which the homologous region is different from HLA-A2, and the amino acids by which they differ, (phenylalanine to leucine at 294 for A1, A3, All, A30, A36 etc).

In group 2: there was no response.

In group 3: 1/5 patients made a response to peptides from the α3 and transmembrane domains. This again is consistent with the hypothesis that patients sensitised to other HLA-A, not HLA-A2 are likely to make responses to shared sequences from the α3 and transmembrane domains.

In group 4: 1/6 patients made a response. This is an auto response to p39, 50/51, 52/53 and p11. Such a response has also been observed in 1/6 'non-dialysis' normal controls.

In group 5: 2/8 made a response p39 or p50/51 & p52/53. These patients had received previous transfusions and may therefore have been sensitised at the T lymphocyte level without producing anti-HLA antibody.

Example Patient

Figure 8:
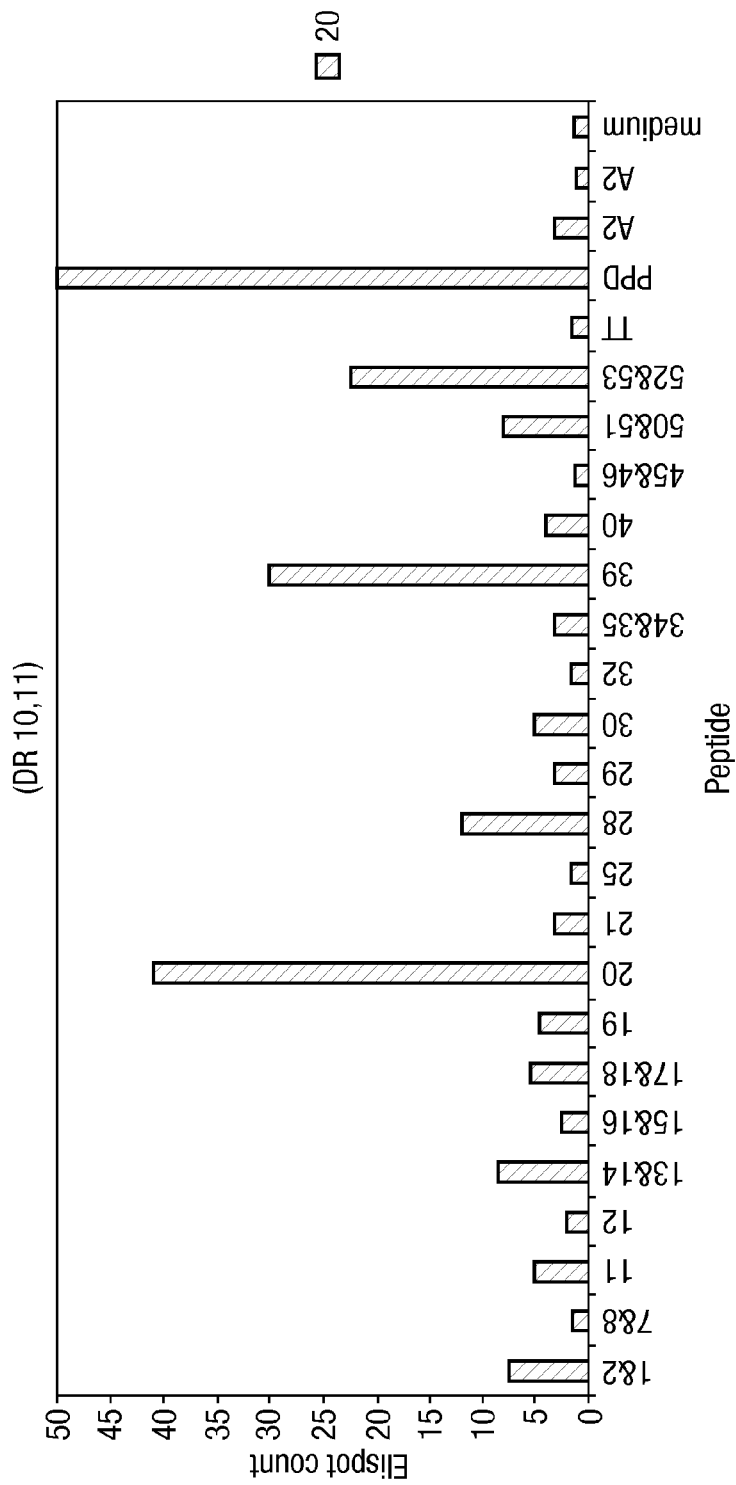
FIG. 8 shows a bar graph showing ELISPOT (enzyme-linked immunosorbent assay) count data of reactive cells/500,000 PBMCs in a single patient for the peptides studied in Example 1'.

Referring to FIG. 8, there is shown an ELISPOT count of peptide reactive cells/500,000 PBMCs. The concentration of peptide was 20 μg/ml. The data show that this individual, who has made high levels of anti-HLA antibody for approximately 10 years, on the background of previous pregnancy and transfusion, makes high frequency responses to p20, p39 and a mixture of p52 and p53. Her tissue type is A1,68; B37,44; C6,7 DR10, 11. Hence, the patient responded to the highly polymorphic region and in particular to a sequence within the HLA-A2 sequence residues 105-121 covered by p20 & 21, that the inventor demonstrated binds promiscuously to MHC class II. She also responded to peptides from the α3 and transmembrane region of HLA-A2, the properties of which are described above. Indeed in her case, these responses are autoreactive because these sequences are shared with HLA-A68. The positive control response is to purified protein derivative of mycobacterium tuberculosis (PPD) and the negative control to medium alone.

Summary

In summary, the results show that peptides of limited polymorphism from the α3 and transmembrane domains frequently induce an immune response. This is usually allogeneic, but sometimes autoimmune, in specificity. The association of responses to these peptides with sensitisation to HLA-A2 implies that they are relevant to anti-HLA antibody formation. They also constitute indirectly presented epitopes that are likely to drive chronic rejection through T cell mediated mechanisms of damage. As these peptides are so widely expressed, they are ideal targets for therapeutic desensitisation. Furthermore, peptide analogues disclosed herein comprising either one or two amino acid substitutions provide almost complete representation of HLA-A.

Furthermore, each of the preferred peptides in accordance with the invention may be expressed by many other HLA-A molecules, and not just HLA-A2. Hence, the inventor believes that the benefits of using such peptides in methods according to the invention, and in particular for uses in treating or preventing allograft failure or rejection, and for antibody synthesis via this or other means of allosensitisation, may be much wider than to HLA-A2 alone. Accordingly, the inventor believes that the implications of their findings is much broader than solely antibody production, but may also relate to immune mechanisms of graft failure or rejection per se, and are wider than target HLA-A2, extending to responses to transplantation antigens in general.

While the inventor does not wish to be bound by any hypothesis, they believe that a mixture or "cocktail" of peptides, derivatives or analogues in accordance with the invention may be used to down-regulate the response to alloantigen, and therefore improve the outcome of transplantation and/or permit the desensitisation of patients who have made anti-HLA antibody. The novelty of the invention lies not only in defining precise peptide sequences of HLA-A2 (i.e. epitopes), but also in the surprising finding that these sequences are what might be called 'public'; this is a term that has until now only been applied to B cell epitopes, because their existence had not been appreciated for T cells. Hence, this surprising finding allows the use of a mixture or cocktail containing a limited number of peptides that will have potentially broad therapeutic benefit.

Example 2

Materials and Methods

Design of Peptides 60 overlapping peptides, 15 or 16 amino acids long, were designed so as to give optimal coverage of HLA-A*020101 for putative T cell epitopes, using the programme Tepitope (33). Solubility of peptides was predicted using the programme at the online database EXPASY. Peptides were synthesized (NeoMPS, Strasbourg, France) using Fmoc chemistry as previously described, but of those designed, only 53 could be made. Biotinylation of control peptides was achieved by reaction with biotinyl-6-aminocaproic acid (Fluka Chimie, St. Quentin Fallavier, France) at the $NH_2$ terminus of the molecule. All peptides were purified by reverse-phase HPLC on a C18 VYDAC brand HPLC column, and their quality was assessed by electrospray mass spectroscopy and analytical HPLC.

Purification of HLA-DR Molecules

HLA-DR molecules were purified from HLA-homozygous EBV cell lines by affinity chromatography using the monoclonal anti-DR antibody L-243, coupled to protein A-SEPHAROSE (Separation-Pharmacia-Agarose) CL 4B gel (Amersham Pharmacia Biotech, Orsay, France) as previously described (Texier et al., J Immunol 2000; 164(6):3177-84).

HLA-DR Peptide Binding Assays

Binding of peptides to different HLA-DR molecules was performed in a competition assay as previously described (Texier et al., Eur J Immunol 2001; 31(6):1837-46). Biotinylated control peptides that are good binders to the MHC class II molecule under investigation were used (see FIG. 9) and test peptides titrated into the binding assay with purified, immobilised MHC class II. Maximal binding was determined by incubating the biotinylated peptide with the MHC class II molecule in the absence of competitor. Data are expressed as the concentration of peptide that prevented binding of 50% of the labelled peptide (IC50). An IC50 ratio of control peptide to test peptide of <20 was considered high affinity binding and 20-100 as moderate affinity.

Study Population

This study was performed with the approval of the South Birmingham research ethics committee. All subjects were on dialysis at University Hospital Birmingham or St James Hospital, Leeds. Blood samples were obtained into heparin from dialysis patients at the time of routine venepuncture. HLA genotypes were determined using standard molecular techniques at the National Blood Service Laboratory, Birmingham, UK, from which the history of alloantibody formation for each subject was available, screened by standard cytotoxicity, flow cytometry and from 2004, solid phase assay.

Patients were excluded on the basis of anaemia (Hb<10 g/dl) or if they had received immunosuppressive drugs within 3 months of the investigation. Subjects were divided into 5 groups on the basis of tissue type and history of anti-HLA antibody synthesis (see Table 4).

TABLE 4

Patient groups

| | |
|---|---|
| Group 1 | HLA-A2 negative with anti HLA antibodies to HLA-A2 |
| Group 2 | HLA-A2 negative with anti HLA antibodies to none-A2 HLA |
| Group 3 | HLA-A2 negative with no history of anti HLA antibody formation |
| Group 4 | HLA-A2 positive with anti HLA antibodies to none-A2 HLA |
| Group 5 | HLA-A2 positive with no history of anti HLA antibody formation |

Enzyme-Linked Immunosorbent Spot Assay

PBMC's were isolated from peripheral blood by Ficoll density-gradient centrifugation prior to use. Viable cells were enumerated by trypan blue exclusion. A γ-interferon ELISPOT assay was used according to the manufacturer's instructions (Mabtech, Nacka Strand, Sweden). A total of $5 \times 10^5$ PBMC's were added to each well, in a final volume of 100 µl of 'complete medium': 95% RPMI 1640 medium (Sigma, Poole, UK)/5% human AB serum (PAA laboratories, Somerset, UK), with L-glutamine and penicillin/streptomycin (Sigma) along with peptide at a final concentration of 4 µgml$^{-1}$ or 20 µgml$^{-1}$. Peptides were used either singly or for some in pairs if the sequences were offset by 2 amino acids.

Negative control wells contained responder PBMC's plus medium alone. Positive control wells contained PPD (SSI, Copenhagen, Denmark) at a final concentration of 10 .mu.g-ml.sup.-1, tetanus toxoid at (Calbiochem, Merck Biosciences, UK) at 1 µg/ml, or latterly a positive control (anti-CD3 based) supplied by the manufacturer of the ELISPOT assay. PBMC's were cultured at 37° C., 5% $CO_2$ for 48 hours, then discarded and the plate washed 6 times with PBS. Plates were then incubated at room temperature for 2 hours with the one-step detection reagent (alkaline phosphatase-conjugated detection monoclonal antibody 7-B6-1, prepared by diluting to 1:200 in filtered PBS containing 0.5% fetal calf serum (Sigma). This was then discarded and plates washed 5 times with PBS. Filtered ready-to-use chromogenic alkaline phosphatase substrate ((nitroblue tetrazolium/5-bromo-4-chloro-3-indolyl phosphate (BCIP/NBT-plus)) provided by manufacturer was added at a volume of 100 µl/well. The plates were allowed to develop and reaction terminated once spots emerged. Plates were washed extensively under tap water and then air-dried in darkness for at least 12 hours before analysis. The number of spots in each well was then counted using an AID ELISPOT plate reader (Strassberg, Germany). A positive response to test peptide was defined if the number of spots per well was significantly greater than control by ANOVA.

Inhibition of Indirect Alloimmune Responses with Anti-MHC Class II Antibodies

The MHC restriction of responses to peptides was investigated by addition of a mixture of an anti-MHC class II monoclonal antibody (Tu39, Becton Dickinson, Oxford, United Kingdom) and an anti-DR monoclonal antibody (L243, Becton Dickinson) to cell cultures.

Assessment of Proliferation by CFSE

PBMC's were resuspended at $10^6$ cells/ml in warm RPMI at 37° C. to which CFSE (Molecular Probes, Cambridge Biosciences) was added at a final concentration of 10 µM. This was incubated at 37° C., 5% $CO_2$ with intermittent agitation for 10 minutes, when human AB serum (Sigma) was added to terminate labelling, and cells were then washed twice. Cells were resuspended at $2.5 \times 10^5$/well in 96-well round-bottom culture plates in 200 µl of complete medium, in the absence or presence of test peptide at a final concentration of 4 µgml$^{-1}$ or 20 µgml$^{-1}$ or PPD at 10 µgml$^{-1}$, then cultured at 37° C., 5% $CO_2$ for 10 days. Cells were recovered from 3 or more wells, washed twice and stained with antibody to CD4 (SK3-PerCP, Becton Dickinson) or CD8 (SK1-PerCP, Becton Dickinson), or with isotype control (IgG1-PerCP, Becton Dickinson). Samples were analysed using a FACSCalibur flow cytometer (Becton Dickinson) using Winmdi 2.8 software (Scripps Research), acquiring information from a total of 50,000 viable cells.

Results

Peptide Binding Studies Demonstrate Multiple Regions of Promiscuous Binding to HLA-DR A total of 60, 15mer peptides spanning HLA-A2 were designed and 53 could be made. The other 7 peptides, largely derived from the transmembrane region, were insoluble and could not therefore be satisfactorily synthesised. The affinity of peptide binding to HLA-DR is shown in FIG. 9.

The data show that several sequences exhibit promiscuous binding to a range of HLA-DR. These include peptide 20 (105-119), the closely overlapping peptide 21 (107-121) and peptide 7 (31-45) which correspond to sequences previously reported from experiments in which peptide was eluted from MHC class II. It is apparent that large numbers of different epitopes from HLA-A2 bind to MHC class II of different specificities (FIG. 9). This is of particular interest since a composite epitope of self derived MHC peptide presented in the context of self MHC class II, would be a secure means by which to define self.

Peptides 20 and 21 also correspond to the epitope (92-120) recognised by DR15 restricted T cell clones generated from the recipient of a failed HLA-A2 mismatched renal transplant.

On the basis of the relatively common finding of high or moderate affinity binding to MHC class II, 30 peptides were further assessed in functional experiments. A small number of peptides offset by two amino acids were used as a mix of two peptides, in order to optimise the utilisation of PBMCs.

γ-interferon Production in Response to Peptides from HLA-A2

The details of subjects recruited are shown in. FIG. 10. The number of cells producing γ-interferon in response to PPD: 143 (15-422)/$10^6$ PBMCs was significantly lower in patients on dialysis who had made alloantibody than in (unmatched) healthy controls 337 (40-885)/$10^6$ PBMCs (p=0.007). The medium controls in these subjects varied between 0-9/$10^6$ PBMCs and the maximum response to peptide was 122/$10^6$ PBMCs.

The number of patients responding to at least one peptide, assessed by γ-interferon ELISPOT is shown in Table 5. The number of patients responding to at least one HLA-A2 derived peptide is shown for each patient group. Patients who make anti-HLA-A2 antibody are significantly more likely than other patients to make an indirect response to HLA-A2 derived peptide.

TABLE 5

Summary of results in each of the 5 groups

| Antibody | Tissue type | |
|---|---|---|
| | A2+ | A2− |
| Anti-HLA with anti-A2 | | Group 1 14/18 |
| Anti-HLA with no anti-A2 | Group 4 1/9 | Group 2 3/8 |
| No anti HLA | Group 5 1/10 | Group 3 2/10 |

In most patients the number of responding cells was highest with peptide at a concentration of 20 μgml$^{-1}$ but in a small number the optimal concentration was 4 μgml$^{-1}$. In FIG. 1 the response to peptide at 20 μgml$^{-1}$ is shown for each individual.

In subject group 1, 14/18 patients made a response to at least one peptide from HLA-A2, shown in FIG. 1a. The number of patients making a response in group 1 was statistically significantly greater than in the other groups combined (p<0.0001) (although compared to group 2 alone the difference did not reach significance p=0.08 by Fishers exact test). The association of indirect alloimmune responses to HLA-A2 and the formation of specific antibody against HLA-A2, is consistent with animal models of alloantibody formation (Lovegrove et al., J Immunol 2001; 167(8):4338-44).

A less expected finding was the observation that although 12 'group 1' subjects responded to peptides from the α1 and α2 hypervariable region (most commonly p20 or p21), of these subjects, 8 also responded to other peptides from the α3 and early transmembrane region; and two more responded to these alone. Responses to peptides from these regions have to our knowledge, not previously been reported in human or animal studies. These sequences are of very limited polymorphism, they are expressed by a wide range of alleles as illustrated in Table 6.

TABLE 6

Illustration of HLA types sharing sequences with HLA-A2 in the region of peptides p39, 40, 50, 51, 52 and 53

| Peptide | Site | Sequence(s) | SEQ ID NO: | Sequenced shared by | and |
|---|---|---|---|---|---|
| P39 | 192-206 | HAVSDHEATLRCWAL | 42 | A2, 25, 26, 29, 31, 32, 33, 43, 66, 68, 69, 74 | A34 |
| P40 | 202-216 | RCWALSFYPAEITLT | 43 | | A34, 80 |
| P50 | 268-282 | KPLTLRWEPSSQPTI | 53 | | A80 |
| P51 | 270-284 | LTLRWEPSSQPTLPI | 54 | | A80 |
| P52 | 280-294 | PTIPIVGIIAGLVLF | 55 | | A3402 |
| P53 | 282-296 | IPIVGIIAGLVLFGA | 56 | | A3402 |

Furthermore 3 patients from 'group 1' made significant responses to peptides from the α3 domain that were shared between HLA-A2 and self HLA-A68 (subject 1.1 responded to p39 and p52/53), HLA-A2 and self HLA-A33 (subject 1.10 responded to p52/53) or HLA-A2 and self HLA-A32 (subject 1.17 responded to p39 and p52/53).

In subject 'group 2', 3 patients responded to a range of HLA-A2 derived peptides (results not shown). For example subject 2.1 responded to peptide p30, 45/46, 50/51 & 52/53 present in a range of different HLA-A (Table 5), including the hypervariable region peptide p30. A similar pattern of response to both hypervariable and α3 and transmembrane region was observed with subject 2.2 and 2.3. None of these peptides are unique to HLA-A2 so the findings remain consistent with the history of antibody production. In patient 2.2 responses were made to sequences p39 and p52/53 shared with self HLA-A68.

In 'group 3', 3 subjects made significant responses to HLA-A2 derived peptides. Subject 3.3 responded to p39, 3.1 to p1/2 and p39 and 3.7 responded to p19 and p52/53. Although these patients did not make anti-HLA antibody detectable on current or historic sera, all had been multiply transfused and it is therefore possible that all had been primed to these peptides without making a humoral response. In patient 'group 4' one patient 4.9, who had rapidly lost a renal transplant (A3,11) to Banff III rejection 17 months prior to testing, made an autoimmune response to p 39, p 50/51 and p52/53 but also to p20 which is unique to HLA-A2. One patient, 5.1 from 'group 5' also made an autoimmune response to peptides p39, p50/51 and p52/53. A group of 15 normal controls, (designated group 6) with no known prior sensitising events were also tested. One male (6.3) made an immune response to HLA-A2 derived peptides including p39, and p50/51 and p52/53. This individual was HLA-A32 positive and these responses were therefore autoimmune. No other normal controls made any detectable response.

γ-interferon Production in Response to HLA-A2 Peptides are Inhibited by Antibody Against MHC Class II The class II restriction of responses was inferred from inhibition of interferon production by antibodies against MHC class II in 3 individuals. A representative experiment is shown in FIG. 11.

Proliferation of CD4$^+$ T Cells in Response to HLA-A2 Peptides

The correspondence of proliferation with .gamma.-interferon production was studied in the 'normal control': 6.3 who responded to peptides p39 and p52/53 assessed by ELISPOT. As shown in FIG. 12, there was proliferation of CD4+ cells in the presence of these peptides but not in the presence of control peptides that did not stimulate interferon production.

Discussion

The contribution of indirect allorecognition to rejection is well established in various experimental models of transplantation (for example, Benichou et al., J Exp Med 1992; 175 (1):305-8). In clinical studies, indirect allorecognition has been associated with chronic rejection of the kidney, heart and lung. The antigens used in these clinical studies include: freeze-thaw lysed cells, peptides spanning the β1 domain of HLA-DR and peptides from the α1 domain of class I HLA. The indirect alloresponse has been detected by the production of IL2, cellular proliferation (in primary or secondary cultures) or cytokine production by ELISPOT.

In both experimental and clinical studies the presence of a single 'immunodominant' epitope is frequently reported, but these findings may be determined by experimental design, such as the use of secondary cultures to detect responses following preliminary expansion of T lymphocyte numbers in vitro. In fact multiple epitopes may be detected using these methods but at different time points post transplantation. Furthermore in animal models of transplantation it is apparent that there may be recognition of multiple epitopes apart from the 'proliferatively immunodominant' epitope; and these responses may include 'cryptic self'.

Use of the ELISPOT technique allows the detection of antigen specific T lymphocytes present at relatively low frequencies, in primary culture. It has allowed our assessment of indirect allorecognition in patients on the renal transplant waiting list. In particular we analysed the immune responses of patients who make an alloantibody of known specificity against HLA-A2. The frequency of responses we have observed are consistent with those seen in renal transplant recipients stimulated with 20mer peptides derived from donor HLA-DR similarly assessed by γ-interferon ELISPOT. These are of the same order of magnitude to frequencies reported from renal transplant recipients stimulated by donor PBMC lysates assessed by DNA synthesis in limiting dilution analysis and lung transplant recipients with bronchiolitis obliterans stimulated by either one or two .alpha.1 domain peptides (A1, A2, B8 and B44 derived) also assayed by DNA synthesis in limiting dilution (SivaSai et al., Transplantation 1999; 67(8): 1094-8). In this report by Sivasai and colleagues a 25mer peptide: 60-84 from the α1 domain of HLA-A2 was used, but we observed a response to this region in only one patient.

Our results demonstrate that although responses to hypervariable region peptides were relatively common, as expected from the literature, there was the unexpected finding of responses to peptides from the α3 and early transmembrane region. As illustrated in table 6, peptide sequences such as p39, p40, p50/51 and p52/53 are widely represented in HLA-A and in those in which these sequences are not present there is commonly a single or dual amino acid polymorphism that encompasses most other types. These peptides could therefore be described as 'public T cell epitopes', the implication of which is that exposure to one HLA molecule can result in the priming of T lymphocytes that respond to a range of other HLA-A family members or vice versa. Since these epitopes are distinct from those recognised by antibody this is one potential mechanism for the diminished allograft survival in sensitised patients, irrespective of the detection of donor specific antibodies. Similarly it suggests a mechanism whereby blood transfusion could influence anamnestic antibody responses, irrespective of the presence of a recognised B cell epitope.

Since sequences identified as 'public T cell epitopes' in HLA-A2 show only very limited polymorphism, it is possible that a portion of the allogeneic response will cross react with self-peptide, as has been reported by Benichou and colleagues for the immune response to MHC class I peptides in mice (Tam et al., J Immunol 1996; 156(10):3765-71); and this possibility is currently under investigation. Indeed a number of the responses described in FIG. 2 are truly autoimmune, since the sequence of the peptide to which a response is made is shared between HLA-A2 and self. This is illustrated by patients 1.1, 1.10 and 1.17. It is similar to the response seen by Lovegrove and colleagues to cryptic self-epitopes, in a rat model of rejection associated with alloantibody formation (Lovegrove et al., J Immunol 2001; 167(8):4338-44).

The finding of 'public T cell epitopes' is also relevant to the mechanism of the blood transfusion effect: the benefit of prior blood transfusion on renal transplant survival, mostly observed before the widespread use of calcineurin inhibitors. Experimental models of the transfusion effect suggest that there is induction of regulatory T cells specific for indirectly presented alloantigen (Kishimoto et al., J Am Soc Nephrol 2004; 15(9):2423-8). Although these generally report donor antigen specific tolerance there are now models, attempting to mimic the clinical scenario, in which random blood transfusions induce regulatory cells that protect against rejection (Bushell et al., Transplantation 2003; 76(3):449-55) apparently without non-specific depression of the immune response (Bushell et al., J Immunol 2005; 174(6):3290-).

In humans the blood transfusion effect requires blood donor and recipient to share at least one HLA-DR and a relatively small number of transfusions for maximum benefit. This is despite the wide range of alloantigen that recipients may encounter. This could be accounted for by the induction of self restricted regulatory cells, specific for allogeneic epitopes that are though common to a wide range of donors. Whilst these need not necessarily be from the MHC, the 'public T cell epitopes' described above fulfil the properties necessary to account for much of the available evidence.

A second property of many of the peptide epitopes derived from HLA-A2 is that they bind with some promiscuity to MHC class II, and correspondingly induce responses in a relatively high proportion of sensitised patients. This was true both of epitopes unique to HLA-A2 and of 'public T cell epitopes'. This, in part permitted conclusions to be drawn from our study of only 55 subjects unselected for HLA type. The implications are though wider with respect to the potential use of such peptides in desensitisation protocols.

There has been longstanding interest in the modulation of rejection by alloantigen derived peptides. These effects are generally antigen specific which if translated into the clinic would limit the usefulness of such an approach. Those HLA derived peptides that have stimulated greatest interest have therefore impacted upon pathways independent of conventional TCR based antigen recognition. This is distinct from many animal models of peptide induced tolerance in which there is evidence of antigen specificity through the induction of regulatory T cells. The properties exhibited by epitopes from the α3 and trans-membrane domains, that is of being both public and promiscuous, identify ideal candidates with which to explore peptide immunotherapy in transplantation. The induction of regulatory T cell activity has for example been reported in allergic patients treated with peptide desensitisation protocols.

In summary the identification of indirect allo-epitopes from the α3 and trans-membrane regions of MHC class I has important implications for the allogeneic immune response, its regulation and the development of antigen specific therapy.

Example 3

The inventor compared the sequence of some of the 15mer allo-epitopes identified in Examples 1 and 2 with the corresponding sequences in other HLA polypeptides. The inventor thereby identified additional allo-epitopes. The results are shown in FIGS. 13 to 16.

The invention claimed is:

1. An isolated polypeptide which is between 15 and 30 amino acids in length and which comprises an amino acid sequence selected from the group consisting of SEQ ID NOs: 53, 54, 55, 56, 64, and 65.

2. A composition comprising the polypeptide according to claim 1 and a pharmaceutically acceptable vehicle.

3. The composition of claim 2, comprising more than one polypeptide.

4. An isolated polypeptide consisting of an amino acid sequence selected from the group consisting of SEQ ID NOs: 53, 54, 55, 56, 64, and 65.

5. An isolated polypeptide consisting of amino acid residues 275-314 of SEQ ID NO: 2.

* * * * *